(12) United States Patent
Connell et al.

(10) Patent No.: US 10,738,234 B2
(45) Date of Patent: Aug. 11, 2020

(54) METHANOGENESIS

(71) Applicant: COMMONWEALTH SCIENTIFIC AND INDUSTRIAL RESEARCH ORGANISATION, Campbell, Australian Capital Territorry (AU)

(72) Inventors: Luke Connell, Malvern East (AU); Regina Sander, Brunswick (AU); Deasy Heryanto, Bulleen (AU); Nicholas Lupton, Carlton North (AU); Michael Camilleri, Sunbury (AU); Zhejun Pan, Mount Waverly (AU)

(73) Assignee: COMMONWEALTH SCIENTIFIC AND INDUSTRIAL RESEARCH ORGANISATION, Campbell, Australian Capital Territory (AU)

( * ) Notice: Subject to any disclaimer, the term of this patent is extended or adjusted under 35 U.S.C. 154(b) by 0 days.

(21) Appl. No.: 15/751,944

(22) PCT Filed: Aug. 11, 2016

(86) PCT No.: PCT/AU2016/050725
§ 371 (c)(1),
(2) Date: Feb. 12, 2018

(87) PCT Pub. No.: WO2017/024350
PCT Pub. Date: Feb. 16, 2017

(65) Prior Publication Data
US 2018/0237683 A1     Aug. 23, 2018

(30) Foreign Application Priority Data

Aug. 12, 2015 (AU) ................................. 2015903226
Mar. 18, 2016 (AU) ................................. 2016901018

(51) Int. Cl.
*C09K 8/582* (2006.01)
*E21B 43/16* (2006.01)
(Continued)

(52) U.S. Cl.
CPC ................. *C09K 8/582* (2013.01); *C12N 1/20* (2013.01); *C12P 5/023* (2013.01); *E21B 43/16* (2013.01); *Y02E 50/343* (2013.01)

(58) Field of Classification Search
CPC .......... C09K 8/582; C12N 1/20; C12P 5/023; Y02E 50/343
(Continued)

(56) References Cited

U.S. PATENT DOCUMENTS

| 3,469,630 | A | * | 9/1969 | Hurd | ....................... E21B 43/20 |
| | | | | | 166/252.1 |
| 4,610,302 | A | * | 9/1986 | Clark | ..................... C09K 8/905 |
| | | | | | 166/246 |

(Continued)

FOREIGN PATENT DOCUMENTS

| WO | 2014094053 | 6/2014 |
| WO | 2015089566 | 6/2015 |

OTHER PUBLICATIONS

International Search Report and Written Opinion dated Sep. 21, 2016 corresponding to International Patent Application No. PCT/AU2016/050725; 8 pages.

*Primary Examiner* — Angela M DiTrani Leff
(74) *Attorney, Agent, or Firm* — Leason Ellis LLP

(57) ABSTRACT

The phenomena of nutrient adsorption are utilised to enhance nutrient bioavailability and enhance methanogenesis efficiency. Thus methods for avoiding or reversing such adsorption or utilising the phenomena in a way favourable to promotion of methanogenesis in a formation, for example, through desorption of bound nutrients, or adsorption com- (Continued)

peting bacteria nutrients or methanogen toxicants, etc., are provided herein.

11 Claims, 25 Drawing Sheets

(51) Int. Cl.
*C12P 5/02* (2006.01)
*C12N 1/20* (2006.01)

(58) Field of Classification Search
USPC .......................................................... 166/246
See application file for complete search history.

(56) References Cited

U.S. PATENT DOCUMENTS

| | | | |
|---|---|---|---|
| 5,363,913 A * | 11/1994 | Jenneman | C09K 8/58 166/246 |
| 2001/0045279 A1 | 11/2001 | Converse et al. | |
| 2007/0251146 A1 * | 11/2007 | Larter | C09K 8/582 48/127.5 |
| 2010/0081184 A1 | 4/2010 | Downey et al. | |
| 2013/0020073 A1 * | 1/2013 | Head | C09K 8/582 166/246 |
| 2014/0034297 A1 * | 2/2014 | Mahaffey | C09K 8/58 166/246 |

\* cited by examiner

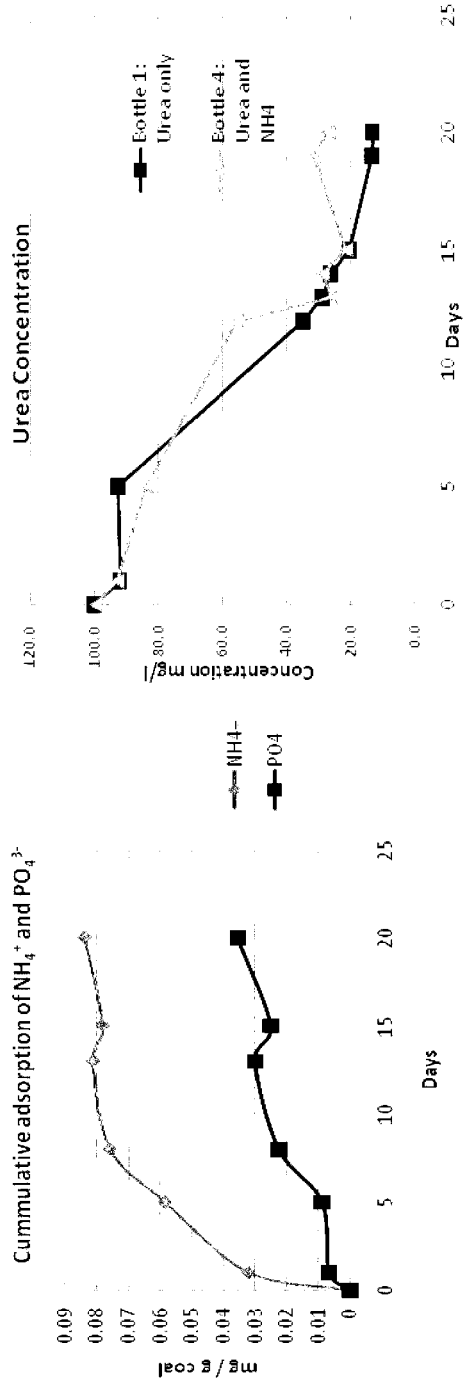
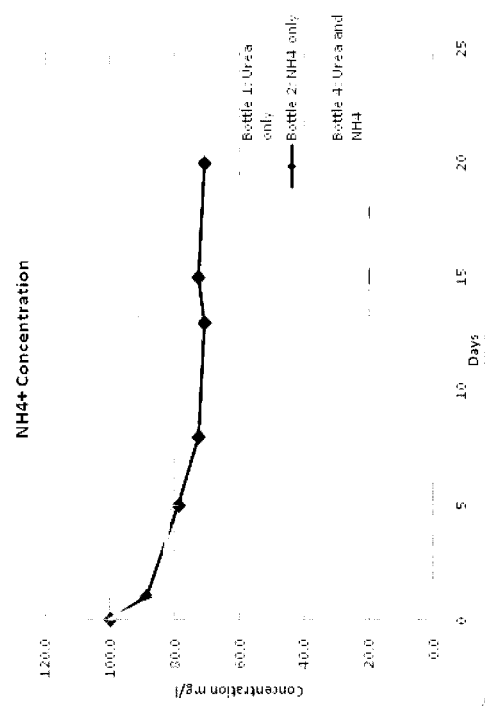
Figure 32
Figure 33

METHANOGENESIS

FIELD OF THE INVENTION

The present invention relates to the microbial production of methane from carbonaceous media, in particular subterranean carbonaceous media, and methods of improving the bioavailability of biostimulating nutrients thereto, to support enhanced methane production from suitable carbonaceous feedstock present in a formation.

BACKGROUND

Methane is formed thermogenically during burial and thermal maturation of coal and/or other hydrocarbons or it may be produced biogenically by the action of microbes on a carbonaceous feedstock. Bacteria are considered to be the primary degraders of compounds in a coal feedstock in, an anoxic and reducing environment, producing a range of intermediates which are successively degraded to small molecule methane precursors, such as, hydrogen gas, carbon dioxide, acetate and various other compounds (e.g., dimethyl sulfide, formate, methanol and methylamines). These precursors are then converted to methane via microbial consortia which comprise methanogenic archaea and include various other bacterial populations. This methanogenic process may occur via a number of mechanisms including $CO_2$ reduction, acetoclastic (from acetate) processes and methylotrophic processes. In this way, carbon from the feedstock enters the carbon cycle to ultimately end up in methane generated in the formation. Due to macronutrient limitations, natural biogenic methane production is slow and occurs over long time-scales. Production from a typical coal seam methane (CSM) well may occur for 5-7 years, after which time, the rate of production generally becomes uneconomic and the well may be abandoned.

Given the potential to recharge reservoirs that are undersaturated in methane, stimulating in-situ biogenic methanogenesis through biostimulating nutrient amendment of formation waters (biostimulation) and/or microbial consortia (bioaugmentation) can have significant economic potential. Laboratory studies have demonstrated that some coal seam formation waters, after biostimulating nutrient amendment, degrade coal feedstock better leading to significant methane generation rates. However the potential for methanogenesis can vary considerably from well to well, even within the same coal basin.

Despite this, when methanogenic consortia in a formation are well supported by a favourable environment such that the methanogenic microbes flourish beyond their natural state, the microbes may become stimulated to convert carbonaceous media feedstock into methane gas at significantly better than natural speeds. In such optimised systems, enhanced methanogenesis rates may result in commercially interesting methane production levels.

Over time however, the rate of methanogenesis gradually lessens until the methane generation rate slows or ceases and the methane recovery process becomes no longer commercially viable. At this point, approaches to re-stimulate or re-invigorate satisfactory rates of methanogenesis become important.

As the rate of gas generation tends to decrease with time, it is believed that this may indicate that only a proportion of the coal feedstock might be available for biological degradation and that plateaus in the gas generation could be attributed to the depletion of "bio-available" coal feedstock. Another hypothesis is that organic intermediates formed during the process and/or the presence of large quantities if biostimulating nutrients added during biostimulation could ultimately be toxic to methanogens and therefore inhibit methanogenesis over time.

U.S. Pat. No. 6,543,535, the relevant contents of which are incorporated herein by reference, provides a process to enhance methane generation from oil deposit feedstocks, such as heavy oils or tar, that are left over after primary and secondary oil recovery processes. The left over oil is typically microtrapped or adsorbed onto mineral surfaces and is unsuitable for typical recovery techniques. The process describes involves methodically analysing the microbial consortia and its subterranean environment to determine the changes in the ecological environment required to promote microbial generation of methane from the oil based feedstock. As the hydrocarbon feedstock in liquid/oil type deposits is materially different to the carbonaceous porous feedstocks described herein, nutrient adsorption and/or desorption processes occurring, if any, are expected to be very different to those observed with a coal feedstock, for example. In short, this document teaches a process for stimulating the activity of pre-existing microbial consortia in a subterranean formation to convert liquid type hydrocarbon feedstock to methane. The process involves analysis of the fluid and rock of the formation, determination of the presence of microbial consortia and characterisation thereof. This information, together with the information obtained from the analysis of the fluid and rock, is used to determine an ecological environment that promotes in-situ microbial degradation of formation hydrocarbons and promotes microbial generation of methane by at least one methanogenic microorganism of the consortia. This information is then used as the basis for modifying the formation environment to produce methane through improved support of microbial consortia particular present by adapting the environment conditions to better suit the consortia present.

U.S. Publication No. 2010/0081184 teaches prophetic methods for optimisation of methane production in a subterranean hydrocarbon formation. Optimisation of methane production is achieved by employing a mathematical model describing the geological, geophysical, hydrodynamic, chemical, biochemical, geochemical, thermodynamic and operational characteristics of systems/processes for the in-situ bioconversion of carbon bearing subterranean feedstocks to methane. Optimisation methods include the introduction of microbial nutrients, methanogenic consortia, chemicals and electrical energy, as required. This document recognises that the amount and rate of bioconversion is a function of several factors, including the specific microbial consortia present, the nature or type of the carbon-bearing formation, the temperature and pressure of the formation, the presence and geochemistry of the water within the formation, the availability and quantity of nutrients required by the microbial consortia to survive and grow, the presence or saturation of methane and other bioconversion products or components, etc. In particular, the document proposes that efficient bioconversion requires optimised delivery and dispersal of nutrients into the formation, the dispersal of microbial consortia across the surface area of the formation, the exposure of as much surface area of the formation to the microbial consortia as possible, and the removal and recovery of the generated methane, carbon dioxide and other hydrocarbons from the formation. To this effect, the methods purposefully increase and maintain the pressure within the subterranean formation well above its initial condition, such that the flow of fluids, nutrients, microbial consortia and generated methane, carbon dioxide and hydrocarbons is optimised. Thus, enhancing nutrient bioavailability focuses on improving the formation's porosity/permeability characteristics, as well as internal and fracture surface area characteristics to improve the bioavailability of ex-situ supplied nutrients by providing better access to microbes by increasing available surface area/penetration as well as ease of removal of gaseous products from the formation.

It should further be noted that a range of factors can inhibit the biogenic conversion of coal to methane. While biostimulating nutrients are important to support and promote biological activity and growth, such amendment can stimulate activity in biostimulating nutrient deficient circumstances, there is an optimal biostimulating nutrient concentration where the beneficial effect is maximised; above this concentration biological activity decreases and eventually the nutrient concentration becomes toxic. Furthermore, since expensive biostimulating nutrients are a key aspect of biostimulation, their consumption relative to the quantity of methane generated will determine the ultimate economic benefit.

It will be appreciated that the subterranean formation environment supporting methanogenesis comprises a number of specific components effecting methanogenesis. These include the particular indigenous microorganism consortia present and their specific biostimulating nutrient and energy consumption requirements, a formation's specific structural components, for example, rock, sand and/or sediment, each having a particular mineralogy, porosity, density, etc., as well as associated chemical and physical properties. Other relevant components may include formation pressure, temperature, etc. Furthermore, associated formation water has a number of relevant chemical and physical properties, for example, pH, conductivity, etc.

It will be appreciated that some aspects of the subterranean formation environment are constrained and cannot be altered, for example, geology, mineralogy, while other variables can be modified relatively easily, for example, formation water biostimulating nutrient concentration, pH, salinity, etc.

Understanding the interplay between the constraints and variables of any formation under investigation with respect to biogenic methanogenesis allows the optimum methanogenesis environment to be determined. Where environmental amendments necessary to promote and/or sustain the activity of the microbial consortia can be identified and applied to a formation via a formation specific environment amendment regime, implementation of such amendments may improve methanogenesis. As discussed in U.S. Pat. No. 6,543,535 and U.S. Publication No. 2010/0081184, By controlled modification of key environmental parameters to support consortia, methanogenesis of carbonaceous media to methane can be initiated, promoted and/or maintained over extended period of time.

It is an object of the present invention to overcome or ameliorate at least one of the disadvantages of the prior art, or to provide a useful alternative.

An object of a preferred embodiment of the invention is to make more efficient use of expensive methanogenesis biostimulating nutrients so that reduced amounts of, and in some embodiments, no ex-situ biostimulating nutrient need to be applied to a formation. In particular it is an object of a particularly preferred embodiment of the invention to provide amendments involving manipulation/utilisation of in-situ nutrients preferably such that no, or at least reduced levels of biostimulating nutrients are required. Furthermore, more efficient use of biostimulating nutrients can be measured, for example, in terms of an increase in methane generated per unit of biostimulating nutrient present.

Any discussion of the prior art throughout the specification should in no way be considered as an admission that such prior art is widely known or forms part of common general knowledge in the field.

Unless the context clearly requires otherwise, throughout the description and the claims, the words "comprise", "comprising", and the like are to be construed in an inclusive sense as opposed to an exclusive or exhaustive sense; that is to say, in the sense of "including, but not limited to".

SUMMARY OF THE INVENTION

A key aspect of the present invention is based on the observation that microbial uptake of biostimulating microbial nutrients that support methanogenesis by adsorption of the nutrients onto formation structures, including feedstock or the feedstock environment, can negatively affect methanogenesis efficiency, particularly with respect to the amount of methane generated per unit of biostimulating nutrient present and/or provided. Where biostimulating the nutrients are adsorbed in this way, their bioavailability is reduced. Therefore, less metabolic support is available to the microbial consortia such that suboptimal levels of methane production result as consortia do not flourish and grow as efficiently in nutrient depleted environments. Additional biostimulating nutrients must be supplied, significantly adding to the cost of methane recovery. Therefore, methods for reducing and/or manipulating biostimulating nutrient adsorption onto carbonaceous feedstock and/or the feedstock environment are desirable, as are methods for the identification of biostimulating nutrients that are less prone to adsorption onto a feedstock and/or feedstock environment. Likewise, desorption of biostimulating nutrients can be advantageously used to support microbes towards more efficient methanogenesis without the need to dose certain nutrients into a formation. In either case, the addition of compensating biostimulating nutrients required to enhance their bioavailability to microbes is reduced, lessening the cost of the methane recovery process and reducing risk of consortia poisoning by nutrient overload. The present invention utilise the phenomena of biostimulating nutrient adsorption, particularly, phosphorus and/or nitrogen adsorption onto carbonaceous feedstock and/or the feedstock environment, to enhance nutrient bioavailability and enhance methanogenesis efficiency with respect to levels of methane generated per unit of nutrient present and/or provided. Thus methods for avoiding and/or reversing such adsorption or utilising the phenomena in a way favourable to promotion of methanogenesis efficiency in a formation per unit of nutrient present and/or provided, for example, through use of non-adsorbable nutrients, through desorption of bound nutrients, controlled release/conversion of adsorbable forms of nutrient, and/or adsorption of competing bacteria nutrients or methanogen toxicants, etc., are provided herein.

The present inventors have found that a formation environment can be modified to make it more favourable to methanogenesis through enhancing biostimulating nutrient bioavailability by one or more amendments involving: (1) adding, removing, adjusting and/or maintaining biostimulating nutrients needed for microbial growth, and/or (2) adjusting, controlling, manipulating and/or maintaining certain formation environmental factors including chemistry, temperature, salinity, and/or pressure, etc., to promote or reduce biostimulating nutrient adsorption and enhance biostimulating nutrient bioavailability. It will be appreciated that desired nutrient bioavailability amendment(s), in the context of controlling the biostimulating adsorption and/or desorption processes described herein, are selected on the basis of various constraints and variables associated with a formation and/or feedstock of interest, as well as consortia energy and nutritional support requirements. It will be appreciated that the consortia nutritional support requirements depend on the type methanogenic microbes present, the nature of the species/relative proportions of species present therein, as well act their activity. It will be understood that wherein the amendment regime requires dosing with a biostimulating nutrient composition or a composition comprising one or more suitable nutrient precursor components, the compositions may comprise any matter or environmental condition which stimulates the production of methane from the native environment, either directly, through stimulation of the microbial consortia, or indirectly, through modification of other components, including nutrient adsorption and/or desorption processes, in the native formation environment which ultimately lead to increased methane levels.

In one broad aspect, the invention provides a process of developing a subterranean formation amendment regime to increase efficiency of stimulated biogenic methanogenesis of a carbonaceous feedstock in a subterranean formation, comprising the steps of:
(a) analysing one or more components of the formation to determine a set of nutrient adsorption/desorption environmental characteristics associated with the formation environment in its native state;
(b) detecting a presence of one or more methanogenic microbes within the formation;
(c) measuring a level of methane gas production occurring within the formation;
(d) using information obtained from steps (a) to (c) to devise an optimised formation environment that promotes optimal in-situ methanogenesis from the feedstock by the methanogenic microbes with respect to enhanced bioavailability of biostimulating nutrients; and
(e) developing a formation environment amendment regime for application to the native formation environment to increase the methanogenesis efficiency by determining one or more adjustments required to the one or more components of the formation to substantially replicate in-situ the optimised formation environment determined in step (d).

In another broad aspect, the invention provides a method of developing a subterranean formation amendment regime to increase efficiency of stimulated biogenic methanogenesis of a carbonaceous feedstock in a subterranean formation, comprising the steps of:
(a) analysing one or more components of the formation to determine a set of nutrient adsorption and/or desorption environmental characteristics associated with the formation environment in its native state, wherein the nutrients are one or more biostimulating nutrients which are adsorbable onto, and/or, desorbable from, the one or more components of the formation;
(b) detecting a presence of one or more methanogenic microbes within the formation;
(c) measuring a level of methane gas production occurring within the formation;
(d) using information obtained from steps (a) to (c) to devise an optimised formation environment with respect to biostimulating nutrient adsorption and/or desorption that promotes optimal in-situ methanogenesis from the feedstock by the methanogenic microbes through modification of the adsorption and/or desorption environmental characteristics of the formation to enhance bioavailability of the one or more biostimulating nutrients; and
(e) developing a formation environment amendment regime for application to the native formation environment to increase the methanogenesis efficiency by determining one or more adjustments required to the one or more components of the formation to substantially replicate in-situ the optimised formation environment with respect to biostimulating nutrient adsorption and/or desorption determined in step (d).

In one alternative of this broad aspect, application of the amendment regime to the formation affects adsorption and/or desorption of the one or more biostimulating nutrients to increase methanogenesis efficiency.

In another alternative of this broad aspect, the amendment regime is developed by comparing the determined nutrient adsorption and/or desorption environmental characteristics associated with the native formation environment of step (a) with those of a theoretical formation environment model of optimal in-situ methanogenesis efficiency by assessing the differences between the native formation environment determined in step (a) and the optimised formation environment devised in step (d) for that native formation environment.

In another alternative of this broad aspect, the amendment regime is developed for that native formation environment, wherein the assessment is executed by an algorithm which determines the optimal one or more adjustment necessary to the native formation environment to replicate the optimised formation environment by calculating the lowest energy methanogenesis model, thereby establishing a preferred formation environment amendment regime.

In another alternative of this broad aspect, the amendment regime comprises adjusting the nutrient adsorption and/or desorption environmental characteristics of the formation by modifying adsorption and/or desorption of at least one nutrient within the formation.

In another alternative of this broad aspect, nutrient adsorption is modified within the formation by altering one or more physicochemical properties of one or more components of the formation to block nutrient adsorption sites or to desorb nutrients within the formation from absorption sites, and wherein the nutrient adsorption sites within the formation are blocked permanently or temporarily blocked for a period ranging from 1 day to 3 years, preferably 1 week to 3 years, or intervals therebetween.

The invention as contemplated is set out in the following numbered clauses:

1. A method of developing a subterranean formation amendment regime to increase efficiency of stimulated biogenic methanogenesis of a carbonaceous feedstock in a subterranean formation, comprising the steps of:
(a) analysing one or more components of the formation to determine a set of nutrient adsorption and/or desorption environmental characteristics associated with the formation environment in its native state, wherein the nutrients are one or more biostimulating nutrients which are adsorbable onto, and/or, desorbable from, the one or more components of the formation;
(b) detecting a presence of one or more methanogenic microbes within the formation;
(c) measuring a level of methane gas production occurring within the formation;
(d) using information obtained from steps (a) to (c) to devise an optimised formation environment with respect to biostimulating nutrient adsorption and/or desorption that promotes optimal in-situ methanogenesis from the feedstock by the methanogenic microbes through modification of the adsorption and/or desorption environmental characteristics of the formation to enhance bioavailability of the one or more biostimulating nutrients; and (e) developing a formation environment amendment regime for application to the native formation environment to increase the methanogenesis efficiency by determining one or more adjustments required to the one or more components of the formation to substantially replicate in-situ the optimised formation environment with respect to biostimulating nutrient adsorption and/or desorption determined in step (d), whereby application of the amendment regime to the formation affects adsorption and/or desorption of the one or more biostimulating nutrients to increase methanogenesis efficiency.

2. A method of developing a subterranean formation amendment regime to increase efficiency of stimulated biogenic methanogenesis of a carbonaceous feedstock in a subterranean formation, comprising the steps of:

(a) analysing one or more components of the formation to determine a set of nutrient adsorption and/or desorption environmental characteristics associated with the formation environment in its native state, wherein the nutrients are one or more biostimulating nutrients which are adsorbable onto, and/or, desorbable from, the one or more components of the formation;

(b) detecting a presence of one or more methanogenic microbes within the formation;

(c) measuring a level of methane gas production occurring within the formation;

(d) using information obtained from steps (a) to (c) to devise an optimised formation environment with respect to biostimulating nutrient adsorption and/or desorption that promotes optimal in-situ methanogenesis from the feedstock by the methanogenic microbes through modification of the adsorption and/or desorption environmental characteristics of the formation to enhance bioavailability of the one or more biostimulating nutrients; and (e) developing a formation environment amendment regime for application to the native formation environment to increase the methanogenesis efficiency by determining one or more adjustments required to the one or more components of the formation to substantially replicate in-situ the optimised formation environment with respect to biostimulating nutrient adsorption and/or desorption determined in step (d) by comparing the determined nutrient adsorption and/or desorption environmental characteristics associated with the native formation environment of step (a) with those of a theoretical formation environment model of optimal in-situ methanogenesis efficiency by assessing the differences between the native formation environment determined in step (a) and the optimised formation environment devised in step (d) for that native formation environment.

3. A method of developing a subterranean formation amendment regime to increase efficiency of stimulated biogenic methanogenesis of a carbonaceous feedstock in a subterranean formation, comprising the steps of:

(a) analysing one or more components of the formation to determine a set of nutrient adsorption and/or desorption environmental characteristics associated with the formation environment in its native state, wherein the nutrients are one or more biostimulating nutrients which are adsorbable onto, and/or, desorbable from, the one or more components of the formation;

(b) detecting a presence of one or more methanogenic microbes within the formation;

(c) measuring a level of methane gas production occurring within the formation;

(d) using information obtained from steps (a) to (c) to devise an optimised formation environment with respect to biostimulating nutrient adsorption and/or desorption that promotes optimal in-situ methanogenesis from the feedstock by the methanogenic microbes through modification of the adsorption and/or desorption environmental characteristics of the formation to enhance bioavailability of the one or more biostimulating nutrients; and (e) developing a formation environment amendment regime for application to the native formation environment to increase the methanogenesis efficiency by determining one or more adjustments required to the one or more components of the formation to substantially replicate in-situ the optimised formation environment with respect to biostimulating nutrient adsorption and/or desorption determined in step (d) for that native formation environment, wherein the assessment is executed by an algorithm which determines the optimal one or more adjustment necessary to the native formation environment to replicate the optimised formation environment by calculating the lowest energy methanogenesis model, thereby establishing a preferred formation environment amendment regime.

4. A method of developing a subterranean formation amendment regime to increase efficiency of stimulated biogenic methanogenesis of a carbonaceous feedstock in a subterranean formation, comprising the steps of:

(a) analysing one or more components of the formation to determine a set of nutrient adsorption and/or desorption environmental characteristics associated with the formation environment in its native state, wherein the nutrients are one or more biostimulating nutrients which are adsorbable onto, and/or, desorbable from, the one or more components of the formation;

(b) detecting a presence of one or more methanogenic microbes within the formation;

(c) measuring a level of methane gas production occurring within the formation;

(d) using information obtained from steps (a) to (c) to devise an optimised formation environment with respect to biostimulating nutrient adsorption and/or desorption that promotes optimal in-situ methanogenesis from the feedstock by the methanogenic microbes through modification of the adsorption and/or desorption environmental characteristics of the formation to enhance bioavailability of the one or more biostimulating nutrients; and (e) developing a formation environment amendment regime for application to the native formation environment to increase the methanogenesis efficiency by determining one or more adjustments required to the one or more components of the formation to substantially replicate in-situ the optimised formation environment with respect to biostimulating nutrient adsorption and/or desorption determined in step (d), wherein the environment amendment regime developed comprises adjusting the nutrient adsorption and/or desorption environmental characteristics of the formation by modifying adsorption and/or desorption of at least one nutrient within the formation.

5. A method of developing a subterranean formation amendment regime to increase efficiency of stimulated biogenic methanogenesis of a carbonaceous feedstock in a subterranean formation, comprising the steps of:
 (a) analysing one or more components of the formation to determine a set of nutrient adsorption and/or desorption environmental characteristics associated with the formation environment in its native state, wherein the nutrients are one or more biostimulating nutrients which are adsorbable onto, and/or, desorbable from, the one or more components of the formation;
 (b) detecting a presence of one or more methanogenic microbes within the formation;
 (c) measuring a level of methane gas production occurring within the formation;
 (d) using information obtained from steps (a) to (c) to devise an optimised formation environment with respect to biostimulating nutrient adsorption and/or desorption that promotes optimal in-situ methanogenesis from the feedstock by the methanogenic microbes through modification of the adsorption and/or desorption environmental characteristics of the formation to enhance bioavailability of the one or more biostimulating nutrients; and
 (e) developing a formation environment amendment regime for application to the native formation environment to increase the methanogenesis efficiency by determining one or more adjustments required to the one or more components of the formation to substantially replicate in-situ the optimised formation environment with respect to biostimulating nutrient adsorption and/or desorption determined in step (d),
 wherein nutrient adsorption is modified within the formation by altering one or more physicochemical properties of one or more components of the formation to block nutrient adsorption sites or to desorb nutrients within the formation from absorption sites, and wherein the nutrient adsorption sites within the formation are blocked permanently or temporarily blocked for a period ranging from 1 day to 3 years, preferably 1 week to 3 years, or intervals therebetween.

6. The method of clause 4, wherein nutrient adsorption within the formation is blocked permanently, or is temporarily blocked for a period ranging from 1 month to 24 months, or intervals therebetween; or the method of clause 5 wherein the nutrient adsorption sites within the formation are blocked permanently, or are temporarily blocked for a period ranging from 1 month to 24 months, or intervals therebetween.

7. The method of any one of the preceding clauses, whereby application of the amendment regime to the formation affects adsorption and/or desorption of the one or more biostimulating nutrients to increase methanogenesis efficiency.

8. The method of any one of the preceding clauses, wherein the method further comprising a pre-treatment step wherein the one or more components of the formation and/or the formation environment are altered to a more optimal environment that results in greater methane production per unit of nutrient input.

9. The method of any one of the preceding clauses, wherein the one or more components of the formation are selected from the feedstock and/or feedstock environment.

10. The method of any one of the preceding clauses, wherein the nutrient adsorption and/or desorption environmental characteristics of the formation are one or more physical and/or chemical properties associated with the one or more components of the formation and/or the formation environment that promote biostimulating nutrient adsorption and/or desorption.

11. The method of any one of the preceding clauses, wherein step (a) further comprises determining an initial level of adsorption and/or desorption of the one or more biostimulating nutrients in the formation environment.

12. The method of clause 11, wherein the step of determining the initial level of adsorption and/or desorption of the one or more biostimulating nutrients in the formation environment involves analysing the formation environment to detect and/or quantify a baseline concentration of the one or more biostimulating nutrients.

13. The method of any one of the preceding clauses, wherein the step of determining the set of nutrient adsorption and/or desorption environmental characteristics of the formation that promote adsorption and/or desorption of the one or more biostimulating nutrients involves:
 (i) establishing a baseline concentration of the adsorbable and/or desorbable biostimulating nutrients;
 (ii) systematically altering one or more physical and/or chemical properties associated with the one or more components of the formation and/or the formation environment that promote biostimulating nutrient adsorption and/or desorption within the formation;
 (iii) identifying one or more nutrient adsorption and/or desorption promoting environmental characteristics of the formation by determining which of the altered properties results in an increase and/or decrease in the baseline concentration of the adsorbable and/or desorbable biostimulating nutrients within the formation.

14. The method of clause 13, wherein (i) determining an increase in the adsorbable and/or desorbable biostimulating nutrients concentration relative to the baseline concentration is indicative of nutrient desorption, occurring within the formation, and (ii) wherein determining a decrease in the adsorbable and/or desorbable biostimulating nutrients level relative to the baseline level is indicative of nutrient absorption, occurring within the formation.

15. The method of any one of the preceding clauses, wherein after application of the amendment regime to the formation, the methanogenesis efficiency is increased compared to the methanogenesis efficiency prior to application of the amendment regime.

16. The method of any one of the preceding clauses, wherein the methanogenesis efficiency is determined with reference to a methanogenesis level per nutrient unit present in, and/or provided to, the formation.

17. The method of any one of the preceding clauses, wherein determining the optimised formation environment with respect to biostimulating nutrient adsorption and/or desorption involves associating the determined nutrient adsorption and/or desorption environmental characteristics of step (a) with the level of methane gas production measured in step (c) and/or with the detection of one or more methanogenic microbes in step (b).

18. The method of any one of the preceding clauses, wherein the step of developing the formation environment amendment regime for application to the native formation environment of step (d) involves determining one or more amendments to be applied to the native formation environment to replicate the optimised formation environment with respect to biostimulating nutrient adsorption and/or desorption devised in step (d).

19. The method of any one of the preceding clauses, wherein the step of developing the optimised formation environment with respect to biostimulating nutrient adsorption and/or desorption of step (e) involves comparing the determined nutrient adsorption and/or desorption environmental characteristics associated with the native formation environment of step (a) with those of a theoretical formation environment model of optimal in-situ methanogenesis efficiency.

20. The method of any one of the preceding clauses, wherein the step of developing the formation environment amendment regime of step (e) involves assessing the differences between the native formation environment determined in step (a) and the optimised formation environment with respect to biostimulating nutrient adsorption and/or desorption devised in step (d) for that native formation environment.

21. The method of clause 20, wherein the assessment is executed by an algorithm which determines the optimal one or more adjustments necessary to the native formation environment to replicate the optimised formation environment with respect to biostimulating nutrient adsorption and/or desorption by calculating the lowest energy methanogenesis model, thereby establishing a preferred formation environment amendment regime.

22. The method of clause 21, wherein the calculation is based on one or more formation components and/or environmental constraint and variables.

23. The method of any one of the preceding clauses, wherein replication of the optimised formation environment with respect to biostimulating nutrient adsorption and/or desorption in the native formation adjusts the nutrient adsorption and/or desorption environmental characteristics of the formation to enhance bioavailability of nutrients favouring methanogenesis within the formation or provided to the formation.

24. The method of any one of the preceding clauses, wherein the formation environment amendment regime developed comprises adjusting the nutrient adsorption and/or desorption environmental characteristics of the formation to enhance nutrient bioavailability by increasing nutrient penetration within the formation.

25. The method of any one of the preceding clauses, wherein the environment amendment regime developed comprises adjusting the nutrient adsorption and/or desorption environmental characteristics of the formation by supplying one or more nutrients having substantially no adsorption affinity within the formation or having a low adsorption affinity within the formation of the order of 10% or less by mass, for example, urea or urea derivatives.

26. The method of clause 25, wherein the environment amendment regime developed comprises adjusting the nutrient adsorption and/or desorption environmental characteristics of the formation to favour desorption of nutrients within the formation.

27. The method of any one of the preceding clauses, wherein the environment amendment regime developed comprises altering one or more physicochemical properties of one or more components of the formation analysed in step (a), wherein one or more of components of the native formation are constrained and one or more of the components are variable.

28. The method of any one of the preceding clauses, wherein the one or more of nutrient adsorption and/or desorption environmental characteristics are selected from the group consisting of: physical and/or chemical properties of the formation fluid, formation geology and/or carbonaceous feedstock or feedstock environment within the formation, formation pressure, formation temperature, formulation microbial ecology, formation water chemical or physical properties, such as pH, salinity, conductivity, viscosity, temperature, ionic strength, indigenous nutrient concentration, dosed nutrient concentration, and microbial ecology composition.

29. The method of any one of the preceding clauses, wherein the environment amendment regime developed comprises adjusting the nutrient adsorption/desorption environmental characteristics of the formation by modifying adsorption/desorption of at least one nutrient within the formation.

30. The method of clause 29, wherein nutrient adsorption/desorption of the at least one nutrient within the formation is modified by altering one or more physicochemical properties of one or more components of the formation to favour desorption of certain nutrients within the formation and/or absorption of other nutrients within the formation, and/or to disfavour desorption of certain nutrients within the formation and/or absorption of other nutrients within the formation, or wherein nutrient adsorption is modified within the formation by altering one or more physicochemical properties of one or more components of the formation to block nutrient adsorption sites and/or to desorb nutrients within the formation from adsorption sites.

31. The method of clause 29 or clause 30, wherein the desorption of nutrients within the formation and/or the absorption of nutrients within the formation is permanent or temporary, wherein preferably the desorption and/or absorption is temporary, occurring for a period ranging from 1 day to 3 years, preferably 1 week to 3 years, or intervals therebetween or wherein the nutrient adsorption sites within the formation are blocked permanently or temporarily blocked for a period ranging from 1 day to 3 years, preferably 1 week to 3 years, or intervals therebetween.

32. The method of clause 30 or clause 31, wherein the desorption of nutrients within the formation and/or the absorption of nutrients within the formation is permanent or temporary and involves use of a no adsorption affinity nutrient or a low adsorption affinity nutrient, preferably, wherein the low adsorption affinity nutrient is provided in a precursor form which is convertible and/or degradable to a more bioavailable nutrient form susceptible to absorption, more preferably wherein the low adsorption affinity nutrient, for example, urea, is provided in combination with a precursor conversion and/or degradation inhibitor, such as, a urease inhibitor; or wherein the nutrient adsorption sites within the formation are temporarily blocked for a period ranging from 1 day to 3 years, preferably 1 week to 3 years, or intervals therebetween by adding one or more binding component to the formation which preferentially adsorb to nutrient adsorption sites, wherein the binding component blocks, or preferentially occupies, one or more of the nutrient adsorption sites within the formation, preferably, the binding component is optionally releasable from the nutrient adsorption sites.

33. The method according to any one of clauses 5 or 6, and 30 to 32 wherein nutrient adsorption sites within the formation are blocked using one or more of an organic acid, such as, acetic acid, oxalic acid, tartaric acid or lactic acid.

34. The method of any one of the preceding clauses, wherein the environment amendment regime developed comprises adjusting the nutrient adsorption and/or desorption environmental characteristics of the formation to increase desorption of nutrients within the formation to increase in-situ bioavailability.

35. The method of clause 34, wherein the nutrient bioavailability is adjusted by dosing a feedstock and/or a surrounding feedstock environment with a component that promotes desorption, or preferential desorption, of one or more nutrients adsorbed on the feedstock and/or surrounding environment, whereby the component is optionally releasable therefrom.

36. The method of clause 35, wherein desorption of nutrients from within the formation is promoted by adding an exchange component to the formation, wherein the exchange component preferentially exchanges with adsorbed nutrients to desorb nutrients favoured for methanogenesis.

37. The method of clause 36, wherein the preferential exchange of the exchange component to the nutrient binding sites is a temporary or permanent exchange (controlled release).

38. The method of clause 37, wherein the exchange component is an ion exchange component.

39. The method of any one of the preceding clauses, wherein the microbial biostimulant bioavailability is adjusted by releasing native nutrients adsorbed within the formation by desorption from within the formation, feedstock or feedstock environment.

40. The method of any one of the preceding clauses, wherein the nutrient adsorption and/or desorption is modified within the formation by effecting a change in form of the nutrient or precursor thereto, for example, by changing pH or by adding a reactant, for example, and enzyme or a chemical, to the formation to produce a bioavailable form of the nutrient, for example, one or more different ionic forms.

41. The method of any one of the preceding clauses, whereby the amendment to the native formation environment is such that the development of the native formation environment into the optimised formation environment with respect to biostimulating nutrient adsorption and/or desorption occurs within a predetermined timeframe.

42. The method of any one of the proceeding clauses, wherein the methane gas production occurring within the formation detected in step (b) is zero.

43. The method of clause 42, wherein the methane gas production level is zero, the environment amendment regime developed includes at least one bioaugmentation step.

44. The method of any one of the preceding clauses, wherein the theoretical optimised methane gas production occurring within the formation is from about 5 to about 100% higher than in the native formation.

45. The method of any one of the preceding clauses, wherein analysing step (a) is carried out two or more times at one or more locations around a native formation, more preferably, a plurality of times at a plurality of locations around the formation.

46. The method of any one of the preceding clauses, whereby the formation environment amendment regime is improved by updating the optimised formation environment with respect to biostimulating nutrient adsorption and/or desorption devised in step (d) after each amendment step of the regime is applied.

47. The method of clause 46, wherein the updating step results from with the continuous or periodical monitored effects of one or more amendments applied to the formation during and/or after amendment.

48. A method for methanogenesis site selection comprising the steps of:
(a) analysing one or more components of the formation to determine a set of nutrient adsorption and/or desorption environmental characteristics associated with the formation environment in its native state, wherein the nutrients are one or more biostimulating nutrients which are adsorbable onto, and/or, desorbable from, the one or more components of the formation;
(b) detecting a presence of one or more methanogenic microbes within each formation;
(c) measuring a level of methane gas production occurring within each formation;
(d) using information obtained from steps (a) to (c) to devise an optimised formation environment with respect to biostimulating nutrient adsorption and/or desorption that promotes optimal in-situ methanogenesis from the feedstock by the methanogenic microbes through modification of the adsorption and/or desorption environmental characteristics of the formation to enhance bioavailability of the one or more biostimulating nutrients; and
(e) selecting a preferred site for methane production on the basis of adjustability of the absorption/desorption characteristics of the one or more nutrients at each formation as determined by a process of developing a subterranean formation amendment regime regimen of any one of clauses 1 to 47.

49. A method of creating a methanogenesis model for determining optimal methanogenesis conditions in subterranean formations, the process including the steps of:
(a) analysing one or more components of a plurality of formation to determine biostimulating nutrient adsorption and/or desorption environmental characteristics associated each of the plurality of the native formation environment;
(b) detecting a presence of one or more methanogenic microbes within each of the plurality of the formations;
(c) detecting a level of methane gas production occurring within each of the plurality of formations;
(d) using information obtained from steps (a) to (c) to determine a theoretical formation environment modelled for optimised methanogenesis biostimulation efficiency with respect to biostimulating nutrient adsorption/absorption.

50. A method of any one of the preceding clauses, wherein the biostimulating nutrients are not a carbonaceous feedstock or a consortia metabolite of a carbonaceous feedstock.

51. A method of any one of the preceding clauses, wherein the biostimulating nutrients are selected from the group consisting of: minerals, vitamins, trace elements, nitrogen and/or phosphorus, sources of nitrogen and/or phosphorus and combinations thereof.

52. The method of clause 51, wherein sources of nitrogen and/or phosphorus include nitrate and/or phosphate, preferably, fertilizer sources of nitrate and/or phosphate such as nitrogenous and/or phosphate fertilizers.

53. Methanogenesis model prepared by the process of clause 49.

54. Use of a methanogenesis model according to clause 53, in the determination of one or more nutrients suitable for biostimulation of methanogenesis wherein the nutrient is not urea, ammonium, phosphorous and/or potassium.

55. Use of a methanogenesis model according to clause 53, in the determination of one or more chemical components suitable for blocking adsorption and/or promoting desorption of one or more methanogenic microbes nutrients in a subterranean formation, carbonaceous feedstock and/or carbonaceous feedstock environment; and/or for identification of one or more nutrient precursors that are convertible and/or degradable to a more bioavailable form of nutrient over a desired period of time.

56. A process of stimulating biogenic methanogenesis of a carbonaceous feedstock in a native subterranean formation, comprising the applying a formation environment amendment regime to the native formation environment to increase methanogenesis efficiency wherein the formation environment amendment regime is developed by the method of any one of clauses 1 to 47, for the native subterranean environment.

57. A process according to clause 56, wherein the process involves modifying a nutrient dosing plan to account for nutrient bioavailability as determined by a model according to clause 53.

58. Use of an amendment compound for adjusting nutrient adsorption/desorption in stimulated biogenic methanogenesis of a carbonaceous feedstock.

59. Use according to clause 58, wherein the amendment compound is either or both of urea and one or more of a $C_1$-$C_{10}$ organic acid.

60. A nutrient amendment formulation for use in a process according to any one of clauses 1 to 46 or in a use according to clause 58 or clause 59, wherein the formulation comprises:
(i) from about 1-150 mM of one or more $C_1$-$C_{10}$ organic acids;
(ii) an effective amount of one or more of nitrogenous fertilisers;
optionally,
(iii) an effective amount of one or more of phosphate fertilisers; and
(v) the remainder of water.

61. A nutrient amendment formulation for use according to clause 59, wherein the nitrogenous fertilisers include ammonium chloride, urea or combinations thereof.

62. A nutrient amendment formulation for use according to clause 60 or 61, wherein the phosphate fertilisers include potassium hydrogen phosphate.

63. A nutrient amendment formulation for modifying and/or controlling the rate of nutrient absorption within a formation, wherein the formulation comprises at least one inhibitor component for inhibiting conversion and/or decomposition of one or more nutrient precursors to one or more bioavailable forms of the one or more nutrients; and optionally one or more nutrient precursors to one or more bioavailable forms of the one or more nutrients.

64. A nutrient amendment formulation according to clause 63, wherein the one or more nutrient precursors have a lower formation environment adsorption affinity than the one or more bioavailable forms of the one or more nutrients derived therefrom, and/or a higher bioavailability than the one or more nutrient precursors.

65. A nutrient amendment formulation according to clause 63 or 64, wherein the nutrient absorption amendment formulation is adapted for use in a method as defined in any one of clauses 1 to 47 or is adapted for use as a pretreatment formulation for application to a formation prior to initiating a method as defined any one of 1 to 47.

66. A nutrient amendment formulation according to any one of clauses 63 to 65, wherein the at least one inhibitor component is present in an amount effective to delay conversion and/or decomposition of the one or more nutrient precursor into the one or more bioavailable forms of the nutrient for a desired duration, such as, for example, at least one week.

67. A nutrient amendment formulation according to any one of clauses 63 to 66, wherein the nutrient precursor is a nitrogen nutrient precursor, such as urea, a urea derivative or ammonia, or a nitrite/nitrate, or wherein the nutrient precursor is a phosphorous nutrient precursor, such as phosphoric acid.

68. A nutrient amendment formulation according to any one of clauses 63 to 67, wherein when the conversion and/or decomposition of the one or more precursors is enzymatically driven, the at least one inhibitor component is an enzyme inhibitor, for example, a urease enzyme inhibitor or modulator in the case where the precursor is urea.

69. A nutrient amendment formulation according to clause 68, wherein the urease inhibitor comprise a blend or one or more of: propylene glycol, N-(n-butyl)-thiophosphoric triamide, N-methyl-2-pyrrolidone, for example, AGROTAIN®, available from Koch Fertilizer.

70. A nutrient amendment formulation according to any one of clauses 63 to 68, wherein the precursor is urea, and the inhibitor is selected from the group consisting of: one or more of a heavy metal, such as lead, a hydroxamic acid (HXA), a phosphorodiamidate (PPD), an imidazole, a phosphazene and related compounds, N-(n-butyl) thiophosphoric triamide, N-(n-butyl) phosphoric triamide, thiophoshoryl triamide, phenyl phosphorodiamidate, cyclohexyl thiophosphoric triamide, cyclohexyl phosphric triamide, phosphoric triamide, hydroquinone, p-benzoquinone, hexaamidocyclotriphosphazene, thiopyridines, thiopyrimidines, thiopyridine-N oxides, N,N-dihalo-2-imidazolidinone, N-halo-2-oxazolidinone and combinations thereof.

71. A nutrient absorption amendment formulation according to any one of clauses 63 to 67, wherein the conversion and/or decomposition is hydrolysis driven, the at least one inhibitor component is a hydrolysis inhibitor.

72. A nutrient absorption amendment formulation according to any one of clauses 63 to 67, wherein the conversion and/or decomposition results from nitrification, the at least one inhibitor component is an inhibitor of nitrification bacteria.

Thus, in a first aspect, the present invention provides a method of developing a subterranean formation amendment regime to increase efficiency of stimulated biogenic methanogenesis of a carbonaceous feedstock in a subterranean formation, comprising the steps of:
(a) analysing one or more components of the formation to determine a set of nutrient adsorption and/or desorption environmental characteristics associated with the formation environment in its native state, wherein the nutrients are one or more biostimulating nutrients which are adsorbable onto, and/or, desorbable from, the one or more components of the formation;
(b) detecting a presence of one or more methanogenic microbes within the formation;
(c) measuring a level of methane gas production occurring within the formation;
(d) using information obtained from steps (a) to (c) to devise an optimised formation environment with respect to biostimulating nutrient adsorption and/or desorption that promotes optimal in-situ methanogenesis from the feedstock by the methanogenic microbes through modification of the adsorption and/or desorption environmental characteristics of the formation to enhance bioavailability of the one or more biostimulating nutrients; and
(e) developing a formation environment amendment regime for application to the native formation environment to increase the methanogenesis efficiency by determining one or more adjustments required to the one or more components of the formation to substantially replicate in-situ the optimised formation environment with respect to biostimulating nutrient adsorption and/or desorption determined in step (d), whereby application of the amendment regime to the formation affects adsorption and/or desorption of the one or more biostimulating nutrients to increase methanogenesis efficiency.

Also described herein is a process of developing a subterranean formation amendment regime to increase efficiency of stimulated biogenic methanogenesis of a carbonaceous feedstock in a subterranean formation, comprising the steps of:

(a) analysing one or more components of the formation to determine a set of nutrient adsorption/desorption environmental characteristics associated with the formation environment in its native state;

(b) detecting a presence of one or more methanogenic microbes within the formation;

(c) measuring a level of methane gas production occurring within the formation;

(d) using information obtained from steps (a) to (c) to devise an optimised formation environment that promotes optimal in-situ methanogenesis from the feedstock by the methanogenic microbes with respect to enhanced bioavailability of biostimulating nutrients; and (d) developing a formation environment amendment regime for application to the native formation environment to increase the methanogenesis efficiency by determining one or more adjustments required to the one or more components of the formation to substantially replicate in-situ the optimised formation environment determined in step (c).

Preferably, the method involves determining adsorption and/or desorption of one or more nutrients in the formation environment. Thus, preferably, the method includes the step of determining a set of nutrient adsorption and/or desorption environmental characteristics includes one or more steps involving analysing the formation environment to detect and/or quantify the presence of an initial amount of one or more nutrients of interest. The initial level of nutrients determined forms a baseline/initial level or concentration of the one or more nutrients that are associated with the formation environment in its native state. It will be understood that preferred nutrients of interest are those that may experience absorption and/or desorption within the formation environment. In some cases, preferred nutrients may be supplied in precursor form, whereby a source of bioavailable nutrient is provided to a formation under conditions where conversion and/or degradation of the precursor to of bioavailable nutrient can occur. Absorption and/or desorption of the nutrients of interest within the formation environment will be understood to occur under certain formation environment conditions (e.g. absorption and/or desorption promoting physiochemical conditions). It will also be understood that such application of, or, reproduction of, such conditions in the formation will result in nutrient absorption and/or desorption processes occurring with the formation. Where such processes occur, it will be understood that, generally speaking, further analysis will reveal a measurable alteration in the detected initial (baseline) levels of the one or more nutrients of interest. Where nutrient desorption occurs, the nutrient level will be observed to increase relative to the initial level. On the other hand, where nutrient absorption occurs, the nutrient level will be observed to reduce relative to the initial nutrient level.

Therefore, the step of identification of one or more components of the formation environment associated with nutrient adsorption and/or desorption environmental characteristics of a formation can be carried out by screening a particular formation environment, and/or modelled version thereof, for changes in the presence of a detected initial amount of one or more nutrients of interest that may occur, on application of nutrient absorption and/or desorption promoting physiochemical conditions. Thus, screening involves measuring an initial baseline level of one or more nutrients of interest and/or suitable precursors thereto, initiating an environmental adjustment, for example, pH, and remeasuring the level of nutrients present to determine if the environmental adjustment resulted in nutrient adsorption and/or desorption. Preferably, the component analysed is pH. Other analysable components include but are not limited to the nature of the formation fluid (for example, liquid and/or gas), carbonaceous material type, formation geology (for example, rock, sediment, shale, etc.), formation geochemical and geophysical conditions (for example, fluid pH, salinity, ionic strength, density, conductivity, nutrient, bacteria toxicant profile, mineral profiles, adsorption and/or desorption potential for various panels of nutrients, etc.), formation pressure and temperature, as well as the indigenous microbial ecology of the formation.

In one exemplary embodiment, the nutrients of interest are biostimulating nutrients such as nitrogen and/or phosphorus. Where nitrogen and/or phosphorus are mentioned herein it will be understood that these terms encompass suitable sources of these elements, which include, for example, suitable precursors thereto, preferably precursors which can be converted and/or decomposed to bioavailable forms of the nutrient within the formation. For example, suitable sources of nitrogen, which can include suitable precursor components, include one or more of urea, ammonium and nitrate, while suitable sources of phosphorus include phosphoric acid, for and other $PO_4^{2-}$ containing compounds. Thus, the formation environment is analysed to determine the initial (native or indigenous) level of nitrogen and/or phosphorus present. It will be understood that the analysis may extend to bioavailable forms and/or precursors to bioavailable forms of a nutrient in question. One component of the formation environment known to affect nitrogen and/or phosphorus adsorption and/or desorption within the environment is pH. Therefore, in this case, analysis of one component of the formation to determine a set of nutrient adsorption and/or desorption environmental characteristics associated with the formation environment in its native state is the initial pH of the formation (in its native state, i.e., associated with the initial detected levels of nitrogen and/or phosphorus.

The step of devising an optimised formation environment with respect to nitrogen and/or phosphorus adsorption and/or desorption may then be determined with respect to the preferred formation environment pH that would result in provision of the most favourable levels of nitrogen and/or phosphorus that are calculated as being associated with maximised methanogenesis, whereby the favourable levels through nitrogen and/or phosphorus adsorption and/or desorption initiated by the change in pH. Thus, where nitrogen and/or phosphorus desorption occurs, the nitrogen and/or phosphorus level will increase relative to the initial level. On the other hand, where nitrogen and/or phosphorus absorption occurs, the nutrient level will be reduced relative to the initial nitrogen and/or phosphorus level.

Thus, in one embodiment, a formation environment amendment regime for application to the native formation environment to increase the methanogenesis efficiency will be one that brings about a change in the native pH to provide a pH corresponding to that of the preferred formation environment pH associated with maximised methanogenesis through provision of the most favourable levels of nitrogen and/or phosphorus.

Likewise in screening for components of the formation to determine a set of nutrient adsorption and/or desorption environmental characteristics, the observation that a certain change in pH results in nitrogen and/or phosphorus adsorption and/or desorption that produces a most methanogenesis favourable formation environment, identifies pH as a modifiable formation component.

In a second aspect, the present invention provides a process of developing a subterranean formation amendment regime to increase efficiency of stimulated biogenic methanogenesis of a carbonaceous feedstock in a subterranean formation, comprising the steps of:
(a) analysing one or more components of the formation to determine a set of nutrient adsorption and/or desorption environmental characteristics associated with the formation environment in its native state;
(b) detecting a presence of one or more methanogenic microbes within the formation;
(c) measuring a level of methane gas production occurring within the formation;
(d) using information obtained from steps (a) to (c) to devise an optimised formation environment that promotes optimal in-situ methanogenesis from the feedstock by the methanogenic microbes with respect to enhanced bioavailability of biostimulating nutrients; and
(e) developing a formation environment amendment regime for application to the native formation environment to increase the methanogenesis efficiency by determining one or more adjustments required to the one or more components of the formation to substantially replicate in-situ the optimised formation environment determined in step (d) by comparing the determined nutrient adsorption and/or desorption environmental characteristics associated with the native formation environment of step (a) with those of a theoretical formation environment model of optimal in-situ methanogenesis efficiency by assessing the differences between the native formation environment determined in step (a) and the optimised formation environment devised in step (d) for that native formation environment.

Also described herein is a process of developing a subterranean formation amendment regime to increase efficiency of stimulated biogenic methanogenesis of a carbonaceous feedstock in a subterranean formation, comprising the steps of:
(a) analysing one or more components of the formation to determine a set of nutrient adsorption and/or desorption environmental characteristics associated with the formation environment in its native state, wherein the nutrients are one or more biostimulating nutrients which are adsorbable onto, and/or, desorbable from, the one or more components of the formation;
(b) detecting a presence of one or more methanogenic microbes within the formation;
(c) measuring a level of methane gas production occurring within the formation;
(d) using information obtained from steps (a) to (c) to devise an optimised formation environment with respect to biostimulating nutrient adsorption and/or desorption that promotes optimal in-situ methanogenesis from the feedstock by the methanogenic microbes through modification of the adsorption and/or desorption environmental characteristics of the formation to enhance bioavailability of the one or more biostimulating nutrients; and
(e) developing a formation environment amendment regime for application to the native formation environment to increase the methanogenesis efficiency by determining one or more adjustments required to the one or more components of the formation to substantially replicate in-situ the optimised formation environment with respect to biostimulating nutrient adsorption and/or desorption determined in step (d) by comparing the determined nutrient adsorption and/or desorption environmental characteristics associated with the native formation environment of step (a) with those of a theoretical formation environment model of optimal in-situ methanogenesis efficiency by assessing the differences between the native formation environment determined in step (a) and the optimised formation environment devised in step (d) for that native formation environment.

In a third aspect, the present invention provides a process of developing a subterranean formation amendment regime to increase efficiency of stimulated biogenic methanogenesis of a carbonaceous feedstock in a subterranean formation, comprising the steps of:
(a) analysing one or more components of the formation to determine a set of nutrient adsorption and/or desorption environmental characteristics associated with the formation environment in its native state;
(b) detecting a presence of one or more methanogenic microbes within the formation;
(c) measuring a level of methane gas production occurring within the formation;
(d) using information obtained from steps (a) to (c) to devise an optimised formation environment that promotes optimal in-situ methanogenesis from the feedstock by the methanogenic microbes with respect to enhanced bioavailability of biostimulating nutrients; and
(e) developing a formation environment amendment regime for application to the native formation environment to increase the methanogenesis efficiency by determining one or more adjustments required to the one or more components of the formation to substantially replicate in-situ the optimised formation environment determined in step (d) by assessing the differences between the native formation environment determined in step (a) and the optimised formation environment devised in step (d) for that native formation environment, wherein the assessment is executed by an algorithm which determines the optimal one or more adjustment necessary to the native formation environment to replicate the optimised formation environment by calculating the lowest energy methanogenesis model, thereby establishing a preferred formation environment amendment regime.

Also described herein is a process of developing a subterranean formation amendment regime to increase efficiency of stimulated biogenic methanogenesis of a carbonaceous feedstock in a subterranean formation, comprising the steps of:
(a) analysing one or more components of the formation to determine a set of nutrient adsorption and/or desorption environmental characteristics associated with the formation environment in its native state, wherein the nutrients are one or more biostimulating nutrients which are adsorbable onto, and/or, desorbable from, the one or more components of the formation;

(b) detecting a presence of one or more methanogenic microbes within the formation;

(c) measuring a level of methane gas production occurring within the formation;

(d) using information obtained from steps (a) to (c) to devise an optimised formation environment with respect to biostimulating nutrient adsorption and/or desorption that promotes optimal in-situ methanogenesis from the feedstock by the methanogenic microbes through modification of the adsorption and/or desorption environmental characteristics of the formation to enhance bioavailability of the one or more biostimulating nutrients; and (e) developing a formation environment amendment regime for application to the native formation environment to increase the methanogenesis efficiency by determining one or more adjustments required to the one or more components of the formation to substantially replicate in-situ the optimised formation environment with respect to biostimulating nutrient adsorption and/or desorption determined in step (d) for that native formation environment, wherein the assessment is executed by an algorithm which determines the optimal one or more adjustment necessary to the native formation environment to replicate the optimised formation environment by calculating the lowest energy methanogenesis model, thereby establishing a preferred formation environment amendment regime.

In a fourth aspect, the present invention provides a process of developing a subterranean formation amendment regime to increase efficiency of stimulated biogenic methanogenesis of a carbonaceous feedstock in a subterranean formation, comprising the steps of:

(a) analysing one or more components of the formation to determine a set of nutrient adsorption and/or desorption environmental characteristics associated with the formation environment in its native state;

(b) detecting a presence of one or more methanogenic microbes within the formation;

(c) measuring a level of methane gas production occurring within the formation;

(d) using information obtained from steps (a) to (c) to devise an optimised formation environment that promotes optimal in-situ methanogenesis from the feedstock by the methanogenic microbes with respect to enhanced bioavailability of biostimulating nutrients; and (e) developing a formation environment amendment regime for application to the native formation environment to increase the methanogenesis efficiency by determining one or more adjustments required to the one or more components of the formation to substantially replicate in-situ the optimised formation environment determined in step (d), wherein the environment amendment regime developed comprises adjusting the nutrient adsorption and/or desorption environmental characteristics of the formation by modifying adsorption and/or desorption of at least one nutrient within the formation.

Also described herein is a process of developing a subterranean formation amendment regime to increase efficiency of stimulated biogenic methanogenesis of a carbonaceous feedstock in a subterranean formation, comprising the steps of:

(a) analysing one or more components of the formation to determine a set of nutrient adsorption and/or desorption environmental characteristics associated with the formation environment in its native state, wherein the nutrients are one or more biostimulating nutrients which are adsorbable onto, and/or, desorbable from, the one or more components of the formation;

(b) detecting a presence of one or more methanogenic microbes within the formation;

(c) measuring a level of methane gas production occurring within the formation;

(d) using information obtained from steps (a) to (c) to devise an optimised formation environment with respect to biostimulating nutrient adsorption and/or desorption that promotes optimal in-situ methanogenesis from the feedstock by the methanogenic microbes through modification of the adsorption and/or desorption environmental characteristics of the formation to enhance bioavailability of the one or more biostimulating nutrients; and (e) developing a formation environment amendment regime for application to the native formation environment to increase the methanogenesis efficiency by determining one or more adjustments required to the one or more components of the formation to substantially replicate in-situ the optimised formation environment with respect to biostimulating nutrient adsorption and/or desorption determined in step (d), wherein the environment amendment regime developed comprises adjusting the nutrient adsorption and/or desorption environmental characteristics of the formation by modifying adsorption and/or desorption of at least one nutrient within the formation.

It will be understood that in the methods of the invention, development of the environment amendment regime comprises adjusting the nutrient adsorption and/or desorption environmental characteristics of the formation by modifying adsorption and/or desorption of at least one nutrient within the formation. For example, nutrient adsorption/desorption of the at least one nutrient within the formation may be modified by altering one or more physicochemical properties of one or more components of the formation to favour desorption of certain nutrients within the formation and/or absorption of other nutrients within the formation. Alternatively, the formation may be modified to disfavour desorption of certain nutrients within the formation and/or absorption of other nutrients within the formation. For example, absorption may be controlled or delayed by providing non-adsorbing forms of a nutrient, preferably which can serve as a nutrient precursor, for example, which can be converted and/or degraded to a bioavailable, but absorbable form of the nutrient in question. In one embodiment, the nutrient adsorption within the formation may be prevented permanently or temporarily for a period ranging from 1 week to 3 years, or intervals therebetween, depending on the nature of any such precursors provided. For example, preferably, the nutrient adsorption within the formation may blocked permanently, or may be temporarily blocked for a period ranging from about 1 month to about 24 months, or intervals therebetween, more preferably, for a period ranging from about 6 months to about 18 months, or intervals therebetween, and most preferably, for a period of about 12 months (wherein "about" in this context signifies ±2 weeks).

It will be further understood that in the methods of the invention development of the environment amendment regime comprises adjusting the nutrient adsorption/desorption environmental characteristics of the formation by modifying adsorption/desorption of at least one nutrient within the formation. In particular, nutrient adsorption/desorption of the at least one nutrient within the formation may be modified by altering one or more physicochemical properties of one or more components of the formation to cause desorption of nutrients within the formation and/or absorption of nutrients within the formation. Suitably, desorption of nutrients within the formation and/or the absorption of nutrients within the formation may be permanent or temporary, wherein preferably the desorption and/or absorption is temporary, occurring for a period ranging from 1 week to 3 years, or intervals therebetween.

Thus, in a fifth aspect, the present invention provides a process of developing a subterranean formation amendment regime to increase efficiency of stimulated biogenic methanogenesis of a carbonaceous feedstock in a subterranean formation, comprising the steps of:
(a) analysing one or more components of the formation to determine a set of nutrient adsorption and/or desorption environmental characteristics associated with the formation environment in its native state;
(b) detecting a presence of one or more methanogenic microbes within the formation;
(c) measuring a level of methane gas production occurring within the formation;
(d) using information obtained from steps (a) to (c) to devise an optimised formation environment that promotes optimal in-situ methanogenesis from the feedstock by the methanogenic microbes with respect to enhanced bioavailability of biostimulating nutrients; and
(e) developing a formation environment amendment regime for application to the native formation environment to increase the methanogenesis efficiency by determining one or more adjustments required to the one or more components of the formation to substantially replicate in-situ the optimised formation environment determined in step (d), wherein nutrient adsorption is modified within the formation by altering one or more physicochemical properties of one or more components of the formation to block nutrient adsorption and/or to desorb nutrients within the formation, and wherein the nutrient adsorption within the formation is blocked permanently or is temporarily blocked for a period ranging from 1 week to 3 years, or intervals therebetween.

Thus a further related aspect pertains to a process of developing a subterranean formation amendment regime to increase efficiency of stimulated biogenic methanogenesis of a carbonaceous feedstock in a subterranean formation, comprising the steps of:
(a) analysing one or more components of the formation to determine a set of nutrient adsorption and/or desorption environmental characteristics associated with the formation environment in its native state, wherein the nutrients are one or more biostimulating nutrients which are adsorbable onto, and/or, desorbable from, the one or more components of the formation;
(b) detecting a presence of one or more methanogenic microbes within the formation;
(c) measuring a level of methane gas production occurring within the formation;
(d) using information obtained from steps (a) to (c) to devise an optimised formation environment with respect to biostimulating nutrient adsorption and/or desorption that promotes optimal in-situ methanogenesis from the feedstock by the methanogenic microbes through modification of the adsorption and/or desorption environmental characteristics of the formation to enhance bioavailability of the one or more biostimulating nutrients; and
(e) developing a formation environment amendment regime for application to the native formation environment to increase the methanogenesis efficiency by determining one or more adjustments required to the one or more components of the formation to substantially replicate in-situ the optimised formation environment with respect to biostimulating nutrient adsorption and/or desorption determined in step (d),
wherein nutrient adsorption is modified within the formation by altering one or more physicochemical properties of one or more components of the formation to block nutrient adsorption sites or to desorb nutrients within the formation, and wherein the nutrient adsorption sites within the formation are blocked permanently or temporarily blocked for a period ranging from 1 week to 3 years, or intervals therebetween.

For example, preferably, the nutrient adsorption sites within the formation are blocked permanently, or they may be temporarily blocked for a period ranging from about 1 month to about 24 months, or intervals therebetween, more preferably, for a period ranging from about 6 months to about 18 months, or intervals therebetween, and most preferably, for a period of about 12 months (wherein "about" in this context signifies ±2 weeks).

Preferably, the method of the invention further comprises a pre-treatment step wherein the one or more components of the formation and/or the formation environment are altered to a more optimal environment that results in greater methane production per unit of nutrient input.

Suitably, the one or more components of the formation are selected from the feedstock and/or feedstock environment.

Desirably, the nutrient adsorption and/or desorption environmental characteristics of the formation are one or more physical and/or chemical properties associated with the one or more components of the formation and/or the formation environment that promote biostimulating nutrient adsorption and/or desorption.

In a preferred embodiment, step (a) further comprises determining an initial level of adsorption and/or desorption of the one or more biostimulating nutrients in the formation environment.

Typically, the step of determining the initial level of adsorption and/or desorption of the one or more biostimulating nutrients in the formation environment involves analysing the formation environment to detect and/or quantify a baseline concentration of the one or more biostimulating nutrients.

Suitably, the step of determining the set of nutrient adsorption and/or desorption environmental characteristics of the formation that promote adsorption and/or desorption of the one or more biostimulating nutrients involves:
(i) establishing a baseline concentration of the adsorbable and/or desorbable biostimulating nutrients;
(ii) systematically altering one or more physical and/or chemical properties associated with the one or more components of the formation and/or the formation environment that promote biostimulating nutrient adsorption and/or desorption within the formation; and (iii) identifying one or more nutrient adsorption and/or desorption promoting environmental characteristics of the formation by determining which of the altered properties results in an increase and/or decrease in the baseline concentration of the adsorbable and/or desorbable biostimulating nutrients within the formation.

It will be understood that (i) determining an increase in the adsorbable and/or desorbable biostimulating nutrients concentration relative to the baseline concentration is indicative of nutrient desorption occurring within the formation, and (ii) wherein determining a decrease in the adsorbable and/or desorbable biostimulating nutrients level relative to the baseline level is indicative of nutrient absorption occurring within the formation.

Furthermore, it is desirable that after application of the amendment regime to the formation, the methanogenesis efficiency is increased compared to the methanogenesis efficiency prior to application of the amendment regime.

In one embodiment, the methanogenesis efficiency is determined with reference to a methanogenesis level per nutrient unit present in, and/or provided to, the formation.

Suitably, the biostimulating nutrient(s) are not a carbonaceous feedstock or a consortia metabolite of a carbonaceous feedstock.

Desirably, the biostimulating nutrients are selected from the group consisting of: minerals, vitamins, trace elements, sources of nitrogen and/or phosphorus and combinations thereof.

Preferably, the sources of nitrogen and/or phosphorus include nitrate and/or phosphate, preferably, fertilizer sources of nitrate and/or phosphate such as nitrogenous and/or phosphate fertilizers. It will be further understood that the sources of nitrogen and/or phosphorus are preferably sources of bioavailable nitrogen and/or phosphorus. These case include suitable precursors thereof that are capable of conversion and/or degradation into bioavailable forms under conditions in a particular formation, and/or when supplied with a suitable conversion and/or degradation activator, for example, one or more enzymes and/or chemicals.

It will be understood that the amendment regime of the invention is designed relative to an environment optimised with respect to biostimulating nutrient, particularly, nitrogen and/or phosphorus nutrient, adsorption and/or desorption onto feedstock in the formation and/or the feedstock environment. The invention ensures that the amended environment is one where biostimulating nutrient bioavailability is enhanced through improved used of in-situ or ex-situ nutrients, or suitable precursors thereto as described herein, such that overall methanogenesis efficiency, for example, measure in terms of the amount of methane generated per unit of nutrient provided and/or present.

The invention makes more efficient use of methanogenesis biostimulating nutrients when used in methanogenesis biostimulation in subterranean formations. The invention allows reduced amounts of, and in some embodiments, no, ex-situ biostimulating nutrient to be applied to a formation, while promoting methanogenesis. Preferably, the method involves making amendments involving manipulation/utilisation of in-situ biostimulating nutrients, which include bioavailable forms thereof, and/or, suitable precursors thereto. Thus, most preferably, the methods provide amendment regimes that do not require dosing of extrinsic biostimulating nutrients into a formation. Advantageously, avoidance of use of extrinsic biostimulating nutrient addition lessens the possibility of problems with population exposure to toxic levels of excess nutrients, for example. In particularly preferred embodiments, the method provides for one or more amendments to the formation to counter any intermediate negative environments that might arise during site replication.

The invention involves the development of a subterranean formation amendment regime based on the phenomenon of nutrient adsorption and/or desorption within a formation environment. The phenomenon can be utilised to enhance the bioavailability of in-situ or ex-situ biostimulating nutrients to methanogens and/or other bacteria present in the formation. Preferred biostimulating nutrients include nitrogen and/or phosphorus nutrients, including suitable sources of same.

Biostimulating nutrient bioavailability is enhanced through execution of a predetermined series of environmental amendments steps (an amendment regime) designed to modify the formation to favour release and/or uptake of available and/or provided biostimulating nutrients through modification of formation conditions and/or processes that result in adsorption and/or desorption of biostimulating nutrients, including controlled or delayed absorption and/or desorption processes. Thus, application of the amendments devised by the method of the invention positively affecting biostimulating nutrients bioavailability to consortia within the formation.

In particular, the subterranean formation amendment regime is developed by comparison of a particular native environment's biostimulating nutrient absorption/desorption characteristics against a theoretical optimised methanogenesis model of biostimulating nutrient absorption/desorption characteristics for that particular formation environment. This information is used to determine one or more sets of amendments for application to that formation environment to replicate in-situ the optimised nutrient absorption/desorption conditions calculated to enhance methanogenesis through nutrient release or uptake within the formation. Determining the amendment regime by reference to a theoretically optimised model ensures methanogenesis is enhanced in a predictable and consistent way that allows use of the minimum amount required of ex-situ biostimulating nutrients, yet results in more efficient methanogenesis, for example, observed in terms of increased levels/amounts of methane per unit of nutrient present and/or provided. In embodiments, where native in-situ biostimulating nutrients can be made available, no ex-situ biostimulating nutrients may be required. The commercial and environmental benefits of the invention are obvious.

Previous methanogenesis enhancing disclosures focus on the broad concept of optimisation of methanogenesis through modelling studies around environmental characteristics generally, but do not specifically contemplate utilisation of in-situ nutrients nor ways of reducing ex-situ nutrient requirements which are determined by an amendment regime developed through analysis and modelling of biostimulating nutrient adsorption and/or desorption characteristics of a formation. Method of improving in-situ or ex-situ nutrient bioavailability to the consortia through analysis, modelling and modification of biostimulating nutrient absorption/desorption processes occurring within the formation have not been previously disclosed. Likewise, to date there are no disclosures involving monitoring a formation from the perspective of biostimulating nutrient adsorption/desorption, where for example, the nutrients are nitrogen and/or phosphorus.

By "devising an optimised formation environment", it is meant, determining which, of a set of formation environmental characteristics, should be adjusted/amended to provide a modified formation environment capable of making the best and/or most effective use of in-situ and/or ex-situ methanogenesis biostimulating nutrients. In other words determining, on the basis of an adjustable set of native formation environmental characteristics, potential formation environmental characteristics that could arise from the available native formation environmental characteristics for a given formation that would provide the best and/or most effective in-situ methanogenesis from the available feedstock. It will be understood that one way of determining more effective methanogenesis may involve observation of increase amounts of methane generation per unit of nutrient present and/or provided to a formation.

By "devising an optimised formation environment with respect to biostimulating nutrient adsorption/desorption", it is meant determining the most methanogenesis favourable potential formation environmental characteristics associated with control, manipulation, augmentation and/or enhancement of the bioavailability of key biostimulating nutrients required for maximum/most efficient methanogenesis per unit of corresponding nutrient, wherein the control, manipulation, augmentation and/or enhancement of the bioavailability of key biostimulating nutrients occurs by induction of enhanced and/or reduced nutrient adsorption and/or desorption in the native environment in question. Therefore, the term "optimised formation environment with respect to biostimulating nutrient adsorption/desorption" is the theoretically derived formation environment arising from the devising process recited in step (d). It will be appreciated that the starting point for devising the optimised environment depends on the initial conditions in the native formation, particularly with respect to biostimulating nutrient levels and their bioavailability, as well as the associated native level of methanogenesis. In this regard, a key step of the method of the invention is analysis step (a) whereby the key components of the formation associated with the nutrient adsorption and/or desorption environmental characteristics of a formation are analysed, and quantified where possible to provide baseline information regarding the nutrients of interest. This investigation then allows the amendable nutrient adsorption and/or desorption environmental characteristics to be indentified so that the possible changes to same can be considered when carrying out step (d) which involves devising an optimised formation environment with respect to biostimulating nutrient adsorption/desorption. For example, the characteristics of a native environment with respect to adsorption and/or desorption of biostimulating nutrients such as nitrogen and/or phosphorus can be studied. In such a case, the formation environment's native levels of nutrient can firstly be determined, as well as known physical and/or chemical factors that affect that nutrient's adsorption and/or desorption onto a feedstock and/or the feedstock environment can be assessed. Exemplary nutrients include nitrogen and/or phosphorus. Thus, in one embodiment, the analysis of the environment with respect to biostimulating nutrient adsorption and/or desorption might involve an assessment of pH as it is an environmental factor know to affect the form of nitrogen and/or phosphorus and hence the nutrients' bioavailability.

By "nutrient adsorption", it is meant the adhesion of biostimulating nutrient molecules and/or ions onto the surface of one or more geological components of a feedstock bearing formation, such as rock, sediment, or the feedstock itself, for example, coal and/or shale, etc. It will be understood that the process results in a layer of bound nutrient adsorbate onto these surfaces. This means that the adsorbed nutrients are effectively fixed at a given location rather than being free to move throughout a formation. It follows that bioavailability of the adsorbed nutrients is restricted to microbes within the formation which are located at the site of adsorption. In some embodiments, adsorbed nutrients are therefore undesirable compared to non-adsorbed or desorbed nutrients which are unbound and free to travel/diffuse throughout a formation. It will be understood that the latter nutrients have a much higher degree of bioavailability to microbes located throughout the formation.

By "nutrient desorption", it is meant the opposite process to adsorption whereby a nutrient is released from or through a surface. It follows that desorbed nutrients become more available to microbes throughout the formation than when in their adsorbed state.

It will be understood that amount of nutrient adsorption and/or desorption can be measured by considering gas adsorption isotherms of a porous sample and associating changes in gas with the amount of nutrient lost or released from that sample, for example, through sample gravimetric, volumetric and/or nutrient concentration changes observed in the absence of microbes.

By "nutrient adsorption and/or desorption environmental characteristics associated with the formation environment", it is meant the properties or combinations of properties of a given formation that result the overall tendency for adsorption or desorption of any given nutrient onto available formation surfaces. The relevant properties or combinations of properties are described elsewhere herein.

It will be understood that applying the regime to the native formation will amend the biostimulating nutrient adsorption and/or desorption environmental characteristics associated with the formation environment to alter the formation's tendency towards undesirable adsorption of one or more nutrients of interest. Such amendment will increase methanogenesis efficiency therein by enhancing nutrient bioavailability to methanogenic archaea and/or bacteria present which catabolise the feedstock into metabolites suitable for methane conversion by the methanogens. In some cases, amending the other environmental conditions will further support methanogenesis of carbonaceous media present by other means of promotion of methanogenic archaea/consortia activity or making other conditions more favourable to methanogenesis generally.

Advantages flowing from the present methods include a reduction in the nutrient concentration/volume of injection fluid/amount of nutrient required for biostimulation/methane generation in a suitable formation by modifying adsorption and/or desorption processes for better bioavailability or use of available or supplied nutrients. Furthermore, the methods described herein reduce nutrient loss/waste in biostimulation processes, whereby less externally supplied nutrients are absorbed by the feedstock or formation structure. This means less concentrated nutrient biostimulation doses and/or reduced volumes for injection are required for biostimulation that would have been the case for the unamended formation, reducing risk of toxicity and cost. In some embodiments, the methods can be used to identify cheaper, less polluting or locally available nutrients.

It will be understood that "biostimulating nutrient" or "nutrient" as used herein includes a reference to any microbial relevant biostimulating nutrients and/or suitable precursors thereto, vitamins, trace elements, $N_2$ gas, etc., which suitable for enhancing biogenic methanogenesis of carbonaceous material to methane. Nitrogen and/or phosphate nutrients, particularly bioavailable forms thereof and precursor sources thereto are particularly preferred.

The terms carbonaceous "material", "media", "medium" and/or "feedstock" are broadly used to refer to any carbon-containing substance capable of supporting, and are preferably present or provided with, one or more methanogenic microbial populations. It will be appreciated that the terms "material", "media", "medium" and/or "feedstock" are used interchangeably within the specification. It will be understood that the carbonaceous material is subject to degradation by said one or more methanogenic microbial archaea/consortia to release carbon bound thereinto into the carbon cycle whereby such carbon is incorporated into methane or methane precursors which are later converted in situ to methane. Indeed, many of these carbonaceous materials contain significant amount of carbon, which on degradation, typically by anaerobic digestion initiated by hydrolysis of the feedstock and a cascade of reactions that ultimately result in methane and carbon dioxide being generated from intermediate small molecule products including carbon dioxide, hydrogen, ammonia and organic acids. These processes releases carbon from the carbonaceous feedstock which ultimately provides the source of carbon for the methane generated by the methanogenic populations in methanogenesis favouring consortia present in a formation. It is clear that methanogenesis feedstock, typically an organic material comprising a large source of carbon, is one which provides carbon for incorporation into methane produced during methanogenesis. Thus a methanogenesis feedstock, also include the intermediate products, particularly the carbon bearing products, described above, will be understood as providing a source of carbon for incorporation into methane. In other words, the carbon feedstock provides the food required for the consortia populations' energy needs (feedstock is converted to, and used for, energy production). Accordingly, a methanogenesis feedstock must be differentiated from a nutrient as defined above, as any microbial relevant nutrients, minerals, vitamins, trace elements, $N_2$ gas, etc., suitable for enhancing biogenic methanogenesis of carbonaceous material to methane which, as micronutrients, do not ultimately provide a source of carbon for incorporation into methane formed during methanogenesis. Instead, nutrient as intended herein, typically an inorganic component, is one that provides a support role enabling favourable growth of the consortia present, for example, by providing substances to the various populations present required for the organisms to survive and grow. For example, necessary micronutrients include cofactors for metabolism, or substances used for building, growth and repair of the organisms as well as organism metabolic regulation. Key nutrients within the context of the present invention include phosphorus and nitrogen in various useable forms. Nitrogen and/or phosphate nutrients, particularly bioavailable forms thereof and precursor sources thereto are particularly preferred.

Therefore, it is to be appreciated that biostimulating nutrients are components which do not function as feedstock nor do they provide a source of feedstock. Preferred biostimulating nutrients do not comprise fixable carbon. For example, metabolic products such as $CO_2$, acetate, organic acids including citric acid, lactic acid, acetic acid, and carbonic acid feedstocks or feedstock metabolites are not intended as biostimulating nutrients as defined herein. Most preferred biostimulating nutrients are selected from minerals, vitamins, trace elements, nitrogen and/or phosphorus or sources thereof, which are considered as non-feedstock nutrients.

Preferably, the carbonaceous feedstock material can be in solid, liquid, or gaseous form such as coal, carbonaceous shale, lignite, peat, drill cuttings, waste coal, coal derivatives, oil shale, tar sands, oil deposits, hydrocarbon-contaminated soil and petroleum sludges, rich gas or the subsurface of abandoned hydrocarbon formations. Carbonaceous feedstock material also includes consorta small molecular metabolic products such as $CO_2$, acetate, organic acids including citric acid, lactic acid, acetic acid, and carbonic acid, etc. Solid or semi-solid feedstocks are preferred due to more consistent adsorption and/or desorption processes. Preferably, the carbonaceous medium in the formations is solid, for example, coal and carbonaceous shale.

Nutrient Adsorption and/or Desorption Environmental Characteristics Analysis

The biostimulating nutrient adsorption and/or desorption environmental characteristics of a formation of interest are first assessed by analysing one or more components of the formation associated with the formation environment of the formation in its native state in accordance with step (a) above. As used herein, the term "native" applies to a formation which has not previously been stimulated or to one under reassessment for fresh biostimulation after previous methane production has reached an unacceptably low level.

Preferably, the analysing step (a) of the present method is carried out two or more times at one or more formation locations. More preferably still, the analysing step is carried out a plurality of times at a plurality of formation locations to obtain a more thorough picture of the particular formation's environmental conditions.

The analysis is initiated by obtaining at least one sample of at least one formation component as described herein for analysis. More preferably, a plurality of samples of a plurality components of the formation are analysed to give a detailed picture of the particular formation environmental characteristics in question. Thus samples may be taken from a localised area around a particular formation or from a wider area of the formation depending on the size of the potential methane producing field in question. It is preferred that rather than being collected from a single small area, samples from as wide a range as possible are collected so as to provide the most accurate understanding of the formation characteristics over an entire area of interest.

Suitably, the components for analysis to determine the environmental conditions of a native formation include one or more of the following: formation fluid (for example, liquid and/or gas), carbonaceous material type, formation geology (for example, rock, sediment, shale, etc.), formation geochemical and geophysical conditions (for example, fluid pH, salinity, conductivity, nutrient, bacteria toxicant profile, mineral profiles, adsorption and/or desorption potential for various panels of nutrients, etc.), formation pressure and temperature, as well as the indigenous microbial ecology of the formation. By "microbial ecology", it is meant the presence, absence or potential for supporting microbial consortia, archaea, populations, etc., in the formation. Preferably, microbial characterisation of the archaea/consortia includes determining if methanogenic, symbiotic microorganisms that support methanogenic microbes, and/or other bacterial populations that assist in feedstock digestion to methane are present.

For example, the formation component analysis of step (a) preferably includes consideration of one or more non-limiting parameters and the effect on biostimulating nutrient adsorption and/or desorption onto a feedstock or feedstock environment with a formation, and which include:
  formation geology including mineralogical and chemical compositional determinations, temperature, pressure and/or gas composition;

rock, media, and/or sediment analysis, as well as an assessment of certain key physical formation properties including porosity, permeability, capillary pressure, wettability and adsorption and/or desorption potential for various panels of suitable nutrients;

formation water composition and properties including native nutrient concentration, microbial metabolite composition, pH, pressure, temperature, ionic strength, conductivity, specific density, turbidity, etc.;

carbonaceous feedstock composition (e.g. N, P, S, O, C, H content) including maceral composition, hardness, porosity, etc.; and microbial consortia analysis, including colony characterisation including strains/proportions of strains present or other relevant characteristics of methanogens, for example, metabolic by-products, competing microbes, toxins, prebiotics, health, etc.;

vitamins, trace elements and other nutrient of interest; and methane generation rate and/or levels of methane precursors, and/or rate consumption of such precursors, etc.

Through monitoring changes to the indigenous environment occurring overtime, in addition to the nutrient adsorption and/or desorption profile, the biostimulating nutrient dosing composition may be adjusted to ensure that microbial consortia in a formation are not adversely affected by a deprivation of one or more nutrients through adsorption processes or exposed to toxic levels of one or more nutrients through desorption processes.

Suitably, the temperature and pressure of the formation can be measured using existing methods known to the person skilled in the art. Similarly, geochemical and physical analysis of the formation fluid (typically formation water), media, rock and other solids of the formation, can be carried out using analyses known to those skilled in the art. As a result of the fluid nature of the formation environment over time and location, it is preferably that as many types analyses as possible are made to assess the various properties described for samples obtained from one or more locations around the formation.

Suitably, analysis of gas present within the formation is carried out using methods known to the person skilled in the art to highlight the presence of hydrogen, methane, $CO_2$, enzymes, carboxylic acids and/or other metabolites which can be indicative of microbial activity and/or the potential for microbial activity or as evidence of enhancement of same. In particular, hydrocarbon analyses of the carbonaceous media and/or gas present will provide information about the quality/type of feedstock substrates present and will assist in identification of the optimum species of microorganisms that should be present to support optimum methanogenesis for any given nutrient adsorption and/or desorption environmental characteristic profile.

Preferably, at least two of the above component parameters are analysed, more preferably, at least three parameters are analysed, and even more preferably, a plurality of parameters are analysed. In a particularly preferred embodiment, all of the above component parameters may be monitored. In a preferred embodiment, monitoring of the native environment to determine if periodical amendment of the biostimulant nutrient composition dosage is required to compensate for temporal or geographical variations in the indigenous environment, including changes in nutrient adsorption/desorption, as well as formation water chemistry and/or microbial consortia, spatial variations in organic matter composition and/or other essential nutrient levels.

In any given formation or discreet area within a formation, the environmental conditions may be unique to that formation or area within the formation, the conditions for optimum growth of a microorganism consortia may vary widely as can the degree of nutrient adsorption and desorption. It will be understood that conditions favourable for microorganism growth and/or methanogenesis in one part of the formation may not be optimum for another part of the formation. Therefore, microbial characterisation analysis should be associated with the above analyses to determine to the nutrient adsorption and/or desorption environmental characteristics of step (a) above.

It will be appreciated that the greater the number of parameters monitored, the better the understanding of the in-situ native environment with respect to methanogenesis and to nutrient adsorption and/or desorption processes within a formation of interest generally. This enables better development of the formation environment amendment regime of the invention, as well as more sustainable production of biogenic methane through better control of applicable nutrient adsorption and/or desorption amendment processes.

Detecting Methanogenic Microbes

Suitably, where detected in step (b), the one or more methanogenic microbes preferably form part of an indigenous microbial consortia which comprises naturally occurring microbial populations within the formation, feedstock and/or feedstock environment. Suitably, the methanogenic microbes are selected from one or more of the group consisting of: Methanobacteria, Methanococci, Methanomicrobia, Methanopyri, relatives thereof, and combinations of one or more thereof.

In some embodiment, methane gas detection signifies the presence of methanogenic microbes. For example, methane dissolved in samples of formation water is indicative of methane production and the presence of methanogenic microbes. Gas detection is easily carried out using known prior art gas detection techniques.

Suitably, microbial detection may occur by qualitatively comparing the detected microbes to known microbes or closely related microbes, using methods known to those skilled in the art. If useful, quantitative methods can be applied to determine the relative amounts of various species of microbes present in the formation. In some embodiments, the presence of completing flora may be determined, so amendments to suppress such flora can be included in the formation environment amendment regime of the invention.

Microorganism characterisation may be based on conventional microbial detection techniques, which are familiar to those skilled in the art, and involve, for example, DNA and/or culture techniques, as well as comparisons of physiological, biochemical and/or morphological characteristics of the detected bacteria with known bacteria, if useful. As multiple microbial species are typically involved, identification of the consortia microorganisms may provide valuable information into the nutritional needs of the consortia. Thus, in one embodiment, enhancing biogenic production of methane may be further achieved by increasing the size of the methanogenic microbial consortia to increase the rate of methanogenesis in said microbial consortia. If required, one or more bioaugmentation amendments can be included in the amendment regime of the invention, whereby one or more competing and/or symbiotic bacteria can be added, together with key nutrients and other additives if useful to assist in optimising the proportions of microorganisms present in the consortia to better favour methanogenesis.

In one embodiment, the methane gas production occurring within the formation detected in step (b) may be zero. It will be understood that when the methane gas production level is greater than zero, the amendment regime will be such to increase methane production to a greater amount. For example, production can be from about 5 to about 1000% higher compared to that of the native formation. Preferably, the production is about 100%, about 200%, about 300%, about 400%, about 500%, about 600%, about 700%, about 800%, about 900%, or about 1000% higher and all intermediate values, Suitably, the increase in methane gas production is about 10%, about 15%, about 20%, about 25%, about 30%, about 35%, about 40%, about 45%, about 50%, about 55%, about 60%, about 65%, about 75%, about 80%, about 85%, about 90%, about 95%, or about 100% higher than in the native formation.

It will be understood that when the methane gas production level is zero, either consortia are not suitable for methane production. Thus, the environment amendment regime developed may further include at least one bioaugmentation step. If the correct consortia are present, yet are inactive, the microorganisms may simply require one or more rounds of biostimulation and/or nutrient adsorption and/or desorption amendment before suitable levels of methanogenesis result.

Suitably, where required for enhanced methanogenesis with respect to enhanced nutrient bioavailability, one or more methanogenic microbes present may be supported by addition or promotion of one or more commensally acceptable bacteria which promote the growth of methanogens. Preferably, one or more symbiotically acceptable bacteria may be added which produce metabolites or waste that provide energy and/or nutritional support for methanogenesis. It will be appreciated that in either case, the one or more of the bacteria may be supported by addition of at least one probiotic, trace element and/or vitamin, as well as biostimulating nutrients, such as nitrogen and/or phosphorus in suitable forms thereof.

One useful biostimulating amendment, depending on the bioavailability of the nutrients present, or their potential availability from desorption for example, involves bioaugmentation of the formation with suitable microbes depending on the types of methane feedstock present or metabolites likely to be produced. Such extraneous microbes can be provided by injection in order to establish an exogenous microbial population into a formation following identification/characterisation of indigenous microbial populations in the carbonaceous media bearing formation and suitable supporting extraneous microbes and suitable nutrients, mineral and trace elements can be provided to encourage colonisation within same.

It will be understood that introduction of methanogens to the formation, the carbonaceous feedstock or feedstock environment, may be made on the basis of the determined biostimulating nutrient absorption/desorption characteristics for the formation. For example, where certain nutrients can be desorbed from within the formation, the preferred microbial species added may be the best to digest certain carbonaceous feedstock based on the desorbed nutrients. Likewise, if too much biostimulating nutrient is present, the formation can be amended to adsorb the excess to avoid potential toxicity issues. Likewise, as an alternative or in addition, the archaea/consortia can be bioaugmented to include microbial populations that will remove the excess nutrient.

Furthermore, if competing flora are present, they may hinder methanogenesis or may prevent the desired methanogens from flourishing. Thus, in one embodiment, undesirable microbes can be amended by addition of components that retard or suppress growth of such flora, or one or more selective toxins can be added to suppress or kill same to the advantage of the desired flora.

In one embodiment, the one or more methanogenic archaea/consortia and/or microbial populations may be derived from, or may be found in certain formation water from, for example, water from coal bearing rock formations.

Furthermore, it will be appreciated that other non-indigenous non-methanogenic microbes and/or prokaryotes can be added to improve the environment to favour methanogenesis. For example hydrocarbon-digesting microorganisms or other types of microbe may be introduced to assist in the conversion of the carbonaceous media to methane. Thus, qualitative and/or quantitative analysis of the composition of the microbial consortia present is useful to assist in the selection of optimum nutrients/additives required to stimulate methane generation.

Suitably, introduced microbial species may be derived from a bioreactor or engineered microbial cultures. Engineered microbial cultures include those produced through classical selection methods or other genetic modification methods.

In some embodiments, utilisation of natural indigenous microbes is preferred over genetically modified bacterial as introduction of same into the environment may be undesirable in certain locations.

Measuring Methane Levels

As described herein, it will be understood that the level of methane gas production of step (c) can be measured by considering, for example, existing gas analysis methods known in the art. In embodiments where the methane gas production levels are monitored, this can be achieved by considering a parameter such as a peak/maximum of methane generation. A peak/maximum of methane generation can be identified by measuring/monitoring a parameter associated with the amount and/or rate of methane generation that occurs periodically over a certain time frame, so that a peak methane generation amount/rate can be observed prior to a preferably steady and consistent reduction in the methane production thereafter. In other embodiments, the parameter can be peak methane concentration, a peak thermal or ionic conductivity measurement, a peak gas pressure or partial pressure, as well as a peak/maximum average daily % contribution to a methane composition that is collected over a given number of sampling periods of varying intervals. Such methods are known in the art. For example, further discussion of such parameters can be ascertained by consulting the relevant discussion in U.S. Patent Publication No. 2016/0319643, the contents of which is herein incorporated by reference.

Thus in one embodiment, for example, where a substantially continuous gas sensor rapidly measures evolved gas composition, the parameter may be as simple as methane concentration, measured for example, with respect to: % composition (relative to a known volume of gas), $mg/dm^3$, molarity ($m/dm^3$), etc. Similarly, the parameter might be an isotopic ratio, a thermal or ionic conductivity measurement or a gas or partial pressure value that is associated with discrete changes in the evolved gas composition.

In addition to the process of the present invention ensuring sustainable methane production through attenuation of nutrient adsorption and/or desorption processes within a formation, on a feedstock or feedstock environment, the process is preferably also used to avoid the excessive dosage of one or more nutrient components into the formation, including nitrogen. This is desirable from the environmental perspective as well as from avoiding polluting and/or toxic levels of nutrients in the formation that could damage/poison the consortia present.

Devising an Optimised Formation Environment

As mentioned previously, the invention enhances the efficacy of stimulated methanogenesis by adjusting the biostimulating nutrient bioavailability for methanogenesis in a formation of interest by preventing, reducing or promoting environmental biostimulating nutrient uptake or release from a formation environment, from a feedstock and/or a feedstock environment, to favour methanogenesis. A particular advantage is that the amount of non-native biostimulating nutrient to be introduced by biostimulant dosing and/or the amount of dosing water for injection may be decreased, thereby reducing the cost of the methane recovery process.

The step of devising the optimised formation environment of step (d) involves associating the determined biostimulating nutrient adsorption and/or desorption environmental characteristics of step (a) with the detection of one or more methanogenic microbes of step (b), and/or with the level of methane gas production measured in step (c), thereby providing an optimised formation environment that theoretically provides optimal in-situ methanogenesis efficiency based on the nutrient adsorption and/or desorption environmental characteristics of the native formation of interest. It will be understood that the optimised formation environment of step (d) is a simulated set of environmental conditions associated with the optimal methanogenesis possible for a given formation in the context of the formation's particular set of constraints and variable parameters.

In a preferred embodiment, the step of devising the optimised formation environment of step (d) involves comparing the analysed biostimulating nutrient adsorption and/or desorption environmental characteristics associated with the native biostimulating nutrient adsorption and/or desorption formation environment of step (a) with those of a theoretical formation environment model of optimal in-situ methanogenesis efficiency. Preferably, the theoretical formation environment model of optimal in-situ methanogenesis efficiency has been mathematically modelled for optimised methanogenesis biostimulation efficiency on the basis of datasets relating to a plurality of various methanogenesis systems and their particular constraints and variable parameters. The development of the theoretical formation environment model of optimal in-situ methanogenesis efficiency is described elsewhere herein.

It will be understood that the step of developing the simulated optimised formation environment of step (d) involves assessing the differences between the native formation environment determined in step (a) and the theoretical formation environment model of optimal in-situ methanogenesis efficiency and simulating the optimised formation environment on that basis but in the context of the environmental constraints and variables associated with the native formation of interest. The theoretical formation environment model may or may not be limited to the nutrient adsorption and/or desorption environmental characteristics of the methanogenesis system.

Desirably, the assessment of said differences is executed by one or more suitable algorithms capable of determining the optimal set of environment formation conditions associated with the native formation environment based on the rules determined and set by the theoretical formation environment model of optimal in-situ methanogenesis efficiency model.

Suitably, the one or more algorithms calculate a plurality of optimised formation environments for the native formation of interest based on the theoretical formation environment model of optimal in-situ methanogenesis efficiency, but applying the determined constraints and variables associated with the native formation of interest.

Preferably, the optimised formation environment is determined by considering the one or more lowest energy methanogenesis models for the native formation under investigation, and ease of implementing amendments to replicate same in the native formation.

Determining a Formation Amendment Regime

It will be understood that the step of developing the formation environment amendment regime of step (d) involves assessing the differences between the biostimulating nutrient adsorption and/or desorption formation environment characteristics associated with the native formation as determined in step (a) and the optimised formation environment with respect to biostimulating nutrient devised in step (c) for that native formation environment. As explained above, it is preferable that the optimised formation environment is a computer simulated optimised formation environment.

By analysing the differences between the environmental characteristics of the native formation of interest with respect to biostimulating nutrient adsorption/desorption, and particularly the nutrient adsorption and/or desorption characteristics thereof, and the optimised formation environment for that formation, allows the formation environment amendment regime of the invention to be developed. It will be understood that the preferred regime will be the one most easily and/or most cost effectively implemented.

When applied to the native formation environment, the formation environment amendment regime brings the native formation environment closer to the simulated optimised formation environment theorised to support enhanced/optimised methanogenesis by substantially replicating the environmental conditions proposed by the simulation. Insofar as the [simulated] optimised formation environment is developed from the theoretical formation environment model of optimal in-situ methanogenesis efficiency in the context of nutrient adsorption/desorption, applying the formation environment amendment regime enhances the bioavailability of key nutrients to support enhanced methanogenesis within the formation under consideration.

Suitably, applying the methods of the invention and formation environment amendment regime determined therefrom, the theoretical optimised methane gas production occurring within the amended formation will be greater than the unamended system. For example, production may be from about 5 to about 1000% higher than in the native formation. For example, production can be from about 5 to about 1000% higher compared to that of the native formation. Preferably, the production is about 100%, about 200%, about 300%, about 400%, about 500%, about 600%, about 700%, about 800%, about 900%, or about 1000% higher and all intermediate values, Suitably, the optimised methane gas production is about 10%, about 15%, about 20%, about 25%, about 30%, about 35%, about 40%, about 45%, about 50%, about 55%, about 60%, about 65%, about 75%, about 80%, about 85%, about 90%, about 95%, or about 100% higher than in the native formation or in a previous round of stimulation.

It will be further understood that the optimised methane gas production will preferably shown enhanced methanogenesis efficiency measured in terms of increased levels of methane production per unit amount of nutrient present and/or provided, for example, per unit of nitrogen and/or phosphorus.

Formation Amendment Regime

As used herein, a formation amendment regime effectively means the plan for effecting biostimulation of methanogenesis in a formation of interest through modification of biostimulant nutrient adsorption and/or desorption processes occurring therein. The term "biostimulation" means changing one or more environmental conditions in a simultaneous or sequential matter so as to support or enhance methanogenesis using one or more suitable carbonaceous feedstocks in a formation.

Since indigenous microorganisms are typically in a nutrient deprived state, one suitable amendment may involve addition of one or more nutrients in a particular concentration. Biostimulation can also be also effected by an amendment involving adjusting one or more formation environmental conditions to favour more efficient methanogenesis with respect to biostimulating nutrients as described herein. The particular biostimulant nutrient, or combination of biostimulant nutrients, suitable for a particular amendment regime, will depend on the microorganism consortia to be stimulated and the formation environmental conditions as described elsewhere herein. Typical examples including nitrogen and/or phosphorus provided in the form of suitable sources thereof.

Suitably, the formation environment amendment regime devised herein can enhance methanogenesis efficiency by improving biostimulating nutrient (as defined herein) bioavailability in a formation by one or more of the following techniques:
  amending the native formation environment by addition of one or more biostimulating microbial nutrients of interest at non-toxic levels;
  adjusting the nutrient adsorption and/or desorption environmental characteristics of the formation to enhance the bioavailability of one or more nutrients by favourable modification of biostimulating nutrient adsorption and/or desorption from feedstock and/or the feedstock environment;
  releasing native (in-situ) biostimulating nutrients adsorbed within the formation by effecting desorption from within the formation, feedstock and/or the feedstock environment;
  adding biostimulating nutrients in the form of no adsorption affinity or low adsorption affinity nutrients;
  attenuation of adsorption of nutrients within a formation, onto feedstock or the feedstock environment by reduction/prevention of nutrient adsorption and/or increasing/promoting nutrient desorption;
  increasing migration/penetration of nutrients within a formation by reduction/prevention of nutrient adsorption and/or increasing/promoting nutrient desorption; and
  utilising difference rates of adsorption and/or desorption of various nutrients to modify the methane generated to nutrient input ratio to provide enhanced methanogenesis.

Suitably, the step of developing the formation environment amendment regime of step (e) for application to the native formation environment involves determining one or more amendments to be applied to the native formation environment to replicate the simulated optimised formation environment devised in step (d) as described above. It will be further understood that applying the one or more amendments to the native formation environment supports substantial development of the native formation environment to substantially replicate the simulated optimised formation environment devised in step (d).

It will be understood that the formation environment amendment regime developed by the present methods comprises adjusting the nutrient adsorption and/or desorption environmental characteristics of the formation by supplying one or more nutrients having no or poor adsorption affinity within the formation or nutrient precursors having such properties, for example, urea or urea derivatives.

By "no adsorption affinity nutrient", it is meant that the nutrient is in a form that substantially does not adsorb or bind to any of the available surfaces within the formation. It follows that a no adsorption affinity nutrient is therefore one that is essentially completely bioavailable to microbes in the formation in the sense that no loss of nutrient to the formation occurs. For example, a preferred no adsorption affinity nutrient one that is 100% bioavailable to microbes in the formation. It follows that such a nutrient is one that is 0% by mass adsorbed onto the formation components. A less preferred no adsorption affinity nutrient one that is from 98-99.9% bioavailable to microbes in the formation (0.1-2% by mass adsorbed). Similarly, a less preferred no adsorption affinity nutrient is one that is 95-97.9% bioavailable to microbes in the formation.

By "low adsorption affinity nutrient", it is meant that the nutrient is in a form that only tends to adsorb or bind to any of the available surfaces within the formation to a small degree. It follows that a low adsorption affinity nutrient is therefore one that is substantially completely bioavailable to microbes in the formation. For example, a preferred low adsorption affinity nutrient is one that is 50-94.9% bioavailable to microbes in the formation. It follows that such a nutrient is one that is between 5.1-50% by mass adsorbed onto the formation components. A more preferred low adsorption affinity nutrient one that is from 75-94.9% bioavailable to microbes in the formation (5.1-25% by mass adsorbed). Similarly, a more preferred still low adsorption affinity nutrient is one that is 90-94.9% bioavailable to microbes in the formation.

No adsorption affinity nutrient or low adsorption affinity nutrients or precursors thereto include urea, polyphosphate, and derivatives thereof.

It will be appreciated that a "no adsorption affinity nutrient" or a "low adsorption affinity nutrient" can be provided in a form that is a precursor to another form. For example, a no adsorption affinity nutrient can be enzymatically converted, degraded, metabolised and/or chemically converted into a low adsorption affinity nutrient or vice versa. In this embodiment, the components/conditions can be selected to give a conversion time of any desired length or duration, or until otherwise are induced or allowed to convert from one form to another. In this case, it follows that the desired bioavailability and % mass adsorption criteria for a given nutrient can be controlled over a given time period determined by the rate of conversion of one form to another. It will be understood that in such embodiments there is provided for an effective controlled release of nutrient in a form that is susceptible to adsorption within a formation environment.

For example, urea, a poorly absorption nutrient, may be used as a controlled release, for example, a slow release form of the nitrogen nutrient. Urea is decomposed by enzymes, such as urease into ammonia and carbamate, whereby carbamate spontaneously decomposes into ammonia. Ammonia is then converted by bacteria to bioavailable nitrate. The ammonia formed is then nitrified by nitrification bacteria present which convert the ammonia to nitrate. Urea is also chemically hydrolysed to ammonia in the presence of water. It is understood that enzymes typically have optimum operating pH and/or temperature conditions, for example, urease enzyme functions optimally at a pH of around 7.4, and a temperature of about 60° C. Thus, by altering one or more of the environmental characteristics that favour urea conversion to ammonia (for example, pH, temperature) and/or disfavour nitrification of ammonia to nitrate, the degree and/or time required for conversion of urea to a bioavailable source of nitrogen can be controlled, and in particular, slowed to a desirable degree. Preferably, such inhibition can be used to provide a controlled release of nitrogen within the formation over a period of greater than 1 week. Likewise, similar inhibitory conditions can applied to the conversion of nitrates into bioavailable forms.

As explained above, a further mechanism to modify nutrient absorption and/or desorption includes providing one or more desired nutrients in a form that is a precursor to the desired form, particularly where combined with application of one or more conversion/decomposition inhibiting substances, and/or inducing inhibiting environmental conditions to control the bioavailability of nutrient. The application of one or more conversion/decomposition inhibiting substances, and/or inducing inhibiting environmental conditions to control the bioavailability of nutrient can be performed as a pretreatment step and/or at the same time as the amendment regime is applied. For example, urea is a poorly absorbed form of nitrogen nutrient but its conversion/decomposition products, for example, ammonia and ultimately the bioavailable nitrate can be absorbed within the formation environment. Therefore, the degree of adsorption of bioavailable nitrogen in the form of nitrate can be controlled by providing urea to the environment in combination with suitable inhibiting components that control the decomposition and/or degradation of urea to the bioavailable nitrate form. Likewise, ammonia conversion to nitrate can be controlled by inhibiting the nitrification bacteria present that are responsible for conversion of ammonia to nitrate. By use of such controlled release systems/sources of bioavailable nutrient, particularly, bioavailable nutrient or their precursors which are susceptible to adsorption can be temporarily delayed.

Desirably, the invention also provides a nutrient amendment formulation or a nutrient amendment pretreatment formulation for modifying nutrient absorption and/or desorption within a formation, wherein the formulation comprises:

at least one inhibitor component for inhibiting conversion and/or decomposition of one or more nutrient precursors to one or more bioavailable forms of the one or more nutrients; and optionally, one or more nutrient precursors to one or more bioavailable forms of the one or more nutrients.

It will be understood that the nutrient amendment formulation or a nutrient amendment pretreatment formulation as described herein is particularly suited for in the methods and uses according to the invention.

Suitably, the inhibitor component is present in an amount that is effective to delay conversion and/or decomposition of the one or more nutrient precursor to the one or more bioavailable forms of the nutrient for a desired duration. For example, where a delayed conversion and/or decomposition to a nutrient is desired, less inhibitor can be used than where a faster conversion and/or decomposition to a nutrient is desired. Likewise, the amount of inhibitor used can be tailored depending on a particular formation's conditions with respect to delay conversion and/or decomposition. For example, for precursors where heat speeds up the conversion and/or decomposition, application to a hotter environment would require more inhibitor than that for a cooler environment to give the same rate of conversion and/or decomposition. In one embodiment, the nutrient precursor may be urea, a urea derivative or a nitrate. In another embodiment, where the conversion and/or decomposition is enzymatically driven, the at least one inhibitor component can be an enzyme inhibitor. For example, where the nutrient precursor is urea, conversion and/or decomposition to ammonia and/or other bioavailable forms may be caused by urease. In this case, a urease enzyme inhibitor or modulator can be used to control the production of bioavailable nitrogen from urea. One example of a suitable urease inhibitor includes a proprietary blend comprising propylene glycol, N-(n-butyl)-thiophos phoric triamide, N-methyl-2-pyrrolidone, available under the brand name AGROTAIN®, and available from Koch Fertilizer.

Likewise, nitrification inhibiting or modulating enzymes may be used to control the production of bioavailable forms of nitrogen from nitrates. It will be further understood that where precursor conversion and/or decomposition is chemically driven, for example, by hydrolysis, suitable hydrolysis inhibitors can be used to control the production of bioavailable forms of nutrient from suitable precursors.

In the case of urea conversion/decomposition to bioavailable forms of nitrogen, the duration for formation of the nutrient takes from about 4 to about 10 days. This duration can be controlled, for example, extended for a period of at least greater than one week by use of an inhibitor and/or inhibiting environmental conditions as described herein to delay the release of bioavailable, and possibly more adsorbable, forms of nitrogen.

In these embodiments, it will be understood that by providing the nutrient in a no adsorption affinity or low adsorption affinity forms reduces the risk of potential problems with nutrient level reduction by adsorption, such that the microbial consortia benefits fully from full bioavailability of any such amendment dose provided. It will be appreciated that use of such components in a biostimulating composition means less overall nutrient may be required than where adsorbable nutrients were used to effect the same amendment.

Preferably, the environment amendment regime developed by the present methods comprises adjusting the nutrient adsorption and/or desorption environmental characteristics of the formation to favour desorption of nutrients within the formation. In this embodiment, it will be understood that by encouraging desorption of nutrients within the formation, bioavailability of nutrients can be enhanced without requiring a nutrient dosing step. This has obvious beneficial cost implications.

Suitably, the formation environment amendment regime developed to modify biostimulating nutrient adsorption and/or desorption may comprise altering one or more of the variable physicochemical properties of one or more components of the formation analysed in step (a). Suitable amendments may include adjusting certain properties of the formation fluid, formation geology, formation pressure and temperature, formulation microbial ecology, etc., carbonaceous feedstock or feedstock environment and/or other variable components as described elsewhere herein. Desirably, the one or more of components of the native formation for amendment/adjustment are selected from the group consisting of: formation temperature, formation pressure, formation water chemical or physical properties, such as pH, salinity, conductivity, viscosity, temperature, ionic strength, indigenous nutrient concentration, nutrient (native and/or dosed) concentration, oxidation potential, nutrient and toxicant concentrations, and microbial ecology composition, as well as adsorption and/or desorption potential for various panels of suitable nutrients. Nutrients and/or precursors thereof include, for example, phosphorous, nitrate, ammonia, sulphate, urea, polyphosphate, and derivatives thereof, as well as trace element/mineral content, including selenium, molybdenum, cobalt, copper, nickel, and other relevant trace metals.

In particular, nutrient adsorption may be modified within the formation by altering one or more physicochemical properties of one or more components of the formation to block nutrient adsorption sites or to desorb nutrients from within the formation.

As explained herein, depending on the formation characteristics and level of methane required, the nutrient adsorption sites within the formation may blocked permanently or temporarily.

By "permanently blocked", it is meant that the nutrient adsorption sites within the formation are irreversibly occupied or rendered ineffective. In essence, this means that the sites are unavailable to adsorb nutrients, particularly added nutrients provided as part of an amended regime.

It follows that where permanent blockers are used, one or more added nutrients are 100% bioavailable to microbes in the formation. Ideally, the permanent blocker is such that an added nutrient is one that is 0% by mass adsorbed onto the formation components. A less preferred permanent blocker is one that makes one or more added nutrients from 98-99.9% bioavailable to microbes in the formation (0.1-2% by mass adsorbed). Similarly, a preferred permanent blocker still is one that makes one or more added nutrients from 95-97.9% bioavailable to microbes in the formation.

By "temporarily blocked", it is meant that the nutrient adsorption sites within the formation are reversibly occupied or rendered ineffective, for a given period of time or until otherwise induced to dissociate from adsorption sites. In this case, the temporary blocker is such that the above desired bioavailability and % mass adsorption criteria are achieved but for a desired period of time only such that on dissociation the bioavailability and % mass adsorption level are adjustable. This embodiment is useful for controlled uptake of nutrients, for example, where they are present at toxic or polluting levels.

Preferably, the nutrient adsorption sites within the formation are blocked by, for example, adding a binding component to the formation which adsorbs to nutrient adsorption sites, wherein the binding component blocks, or preferentially occupies, one or more of the nutrient adsorption sites within the formation. Suitably, a preferred binding component is one that is optionally releasable from the one or more of the nutrient adsorption sites within the formation. It will be understood that use of one or more optionally releasable binding components allows the adsorption sites to be blocked temporarily.

Where the sites are temporarily blocked, this embodiment advantageously gives the opportunity for controlled absorption whereby the rate of nutrient adsorption is modifiable. Where short acting binding components are used, the nutrient adsorption is attenuated for relatively short period of time, while where longer acting binding components are used, the nutrient adsorption experienced is delayed for more significant periods of time.

Suitably, the binding component may be an ion exchange component.

Other preferred binding components that temporarily or permanently block adsorption sites include small organic compounds such as organic $C_1$-$C_{10}$ organic acids, for example, formic acid, malic acid, benzoic acid, carbonic acid, butyric acid, propionic acid, lactic acid, oxalic acid, acetic acid, tartaric acid, citric acid, etc.

In some embodiments, the one or more permanent blockers, temporary blockers, and/or binding compounds can be added to the formation as a pretreatment in a pretreatment step prior to biostimulation. In other embodiment, the one or more permanent blockers, temporary blockers, and/or binding compounds can be added to the formation simultaneously or sequentially with a desired one or more nutrients during one or more rounds of biostimulation. It will be appreciated that such compounds are provided to the formation, and as such are ex-situ compounds/components.

In one embodiment, the feedstock and/or feedstock environment may be treated to improve the access of nutrients and/or microbes to the feedstock. Such treatment may involve physically and/or chemically fracturing the feedstock and/or feedstock environment to improves access and/or to expose large surface areas of feedstock.

Suitably, the microbial biostimulant bioavailability may be adjusted by releasing native nutrients adsorbed within the formation by desorption from within the formation feedstock and/or the feedstock environment.

Suitably, the nutrient bioavailability may be adjusted by dosing a feedstock and/or a surrounding feedstock environment with a component that promotes desorption, or preferential desorption, of one or more nutrients adsorbed on the feedstock and/or surrounding environment, whereby the component is optionally releasable therefrom.

Desirably, in one embodiment, desorption of nutrients from within the formation is promoted by adding an exchange component to the formation, wherein the exchange component preferentially exchanges with adsorbed nutrients to desorb nutrients favoured for methanogenesis.

In one embodiment, the preferential exchange of the exchange component to the nutrient binding sites is a temporary whereas in another embodiment, the exchange may be a permanent exchange.

It will be understood that the above definitions relating to blocking components are equally applicable to exchange components.

Wherein an exchange component results in temporary desorption, the embodiment gives the opportunity for controlled desorption whereby the concentration of bioavailable nutrient is modifiable since remaining nutrients are later taken up again by re-adsorption as the exchange component gradually disengages from the adsorption sites. Where short acting exchange components are used, it will be understood that the nutrient desorption is effected for only relatively short period of time, while where longer acting exchange components are used, the nutrient re-uptake is delayed for more significant periods of time.

In one exemplary embodiment, the exchange component may be an ion exchange component. Suitably, the exchange component may be an ion exchange component.

Desirable ion exchange components for the above embodiments include chlorides, such as potassium chloride, magnesium chloride, calcium chloride, tetrabutylammonium phosphates, sodium alkanesulfonates, or various cationic or anionic exchange resins known to persons skilled in the art.

These later embodiments effectively allow for nutrient recycling within the formation, the feedstock and/or the feedstock environment.

In a preferred embodiment, the nutrient adsorption and/or desorption is modified within the formation by effecting a change in form of the nutrient, for example, by changing pH or by adding a reactant to the formation to produce a bioavailable form of the nutrient, for example, one or more different ionic forms that are preferably more bioavailable than a previous form.

Preferably, the amendment to the native formation environment is such that the development of the native formation environment into the optimised formation environment occurs within a predetermined timeframe, typically over days, weeks, months or even years.

Self Adapting Model

In a particularly preferred embodiment, the formation environment amendment regime devised by the present methods may be improved by updating the optimised formation environment devised in step (d) after each amendment step of the regime of the invention is applied.

In this case, preferably, the updating step results from an assessment of continuous or periodical monitored effects of one or more amendments applied to the formation during and/or after amendment. Likewise, the effect(s) of one or more amendments applied to the formation on methanogenesis is monitored and fed back to improve the theoretical methanogenesis model. In this regard, the effect(s) of the one or more amendments is continuously or periodically monitored before, during and/or after amendment.

Site Selection

The theoretical formation environment model of optimal in-situ methanogenesis efficiency model can also be use a screening tool to allow identification of formation environments that are most suited and/or most easily amended to initiate, promote and/or sustain methanogenesis of carbonaceous media present in a formation under investigation. Site selection in this manner has obvious commercial benefits as the most economical amendment and optimal formations can be readily identified. Site selection can also be based on the adsorption and/or desorption potential for various panels of nutrients at a particular formation.

Thus, in another aspect, the invention provides a method for methanogenesis site selection comprising the steps of:
(a) analysing one or more formations to determine a set of methanogenesis nutrient adsorption/desorption adsorption and/or desorption environmental characteristics associated with the formation environment in its native state;
(b) detecting a presence of one or more methanogenic microbes within each formation;
(c) measuring a level of methane gas production occurring within each formation;
(d) using information obtained from steps (a) to (c) to devise an optimised formation environment for each formation that promotes optimal in-situ methanogenesis from the feedstock by the methanogenic microbes with respect to enhanced bioavailability of biostimulating nutrients; and
(e) selecting a preferred site for methane production on the basis of adjustability of the absorption/desorption characteristics of the one or more nutrients at each formation as determined by a process of developing a subterranean formation amendment regime regimen as defined in the first aspect.

Furthermore, there is provided a method for methanogenesis site selection comprising the steps of:

(a) analysing one or more components of the formation to determine a set of nutrient adsorption and/or desorption environmental characteristics associated with the formation environment in its native state, wherein the nutrients are one or more biostimulating nutrients which are adsorbable onto, and/or, desorbable from, the one or more components of the formation;
(b) detecting a presence of one or more methanogenic microbes within each formation;
(c) measuring a level of methane gas production occurring within each formation;
(d) using information obtained from steps (a) to (c) to devise an optimised formation environment with respect to biostimulating nutrient adsorption and/or desorption that promotes optimal in-situ methanogenesis from the feedstock by the methanogenic microbes through modification of the adsorption and/or desorption environmental characteristics of the formation to enhance bioavailability of the one or more biostimulating nutrients; and
(e) selecting a preferred site for methane production on the basis of adjustability of the absorption/desorption characteristics of the one or more nutrients at each formation as determined by a process of developing a subterranean formation amendment regime regimen of the invention.

Preferably, the biostimulating nutrients are phosphorus and/or nitrogen, preferably provided in the form of bioavailable sources thereof.

Thus, screening of potentially suitable formations can be carried out by sampling one or more areas/locations within a formation of interest to determine the native environmental conditions associated therewith, particularly with respect to nutrient adsorption and/or desorption as discussed herein. When sufficient environmental condition data is collected and a picture of the native environmental conditions becomes available, the native environmental conditions can then be mapped/compared to the ideal environmental conditions determined by the theoretical formation environment model of optimal in-situ methanogenesis efficiency model, allowing an assessment to be made of environmental amendments required to be made to the particular native environmental conditions to favour initiating, promoting and/or sustaining methanogenesis of a particular carbonaceous media, and/or adsorption and/or desorption potential for various panels of nutrients thereof.

Thus, depending the complexity, cost and resources available to initiate such amendment, decisions can taken with regard to optimal site selection, thereby reducing the risk of poor or failed biostimulation and/or bioaugmentation. A suitable algorithm is preferably used to implement the site selection concept.

Methanogenesis Model Development

The model as described herein corresponds to a set of mathematical rules regarding the methanogenesis system that allows theoretically preferred features of any input system to be determined whereby a minimum set of conditions is applied to the model and the output of same is a variation of the input system against a set of constrained and variable parameters associated with the system.

The theoretical model of methanogenesis in a carbonaceous media bearing geological formation is built to provide one or more optimal solutions to the problem of increasing in-situ methanogenesis in any given formation of interest.

In essence, the theoretical model is based on environmental conditions and methane generation levels measured for a plurality of real-life methanogenesis systems. The theoretical model is then optimised to replicate an optimal methanogenesis processes by following a set of computation rules taking into account system constraints and variables associated with the methanogenesis system starting from a basis set of know parameter associated with a native formation. When sufficient data has been collocated and incorporated into the model, the model allows the prediction of the end state of any particular methanogenesis system when subject to particular amendment, as long as the initial state is known, including the constraints and variables associated with the system under investigation.

The theoretical model thus provides an approximation of an idealised set of amendable environmental conditions within a formation system with respect to the goal of maximising methane generation/efficiency. The theoretical model is preferably based on a machine learning program that processes pluralities of data sets providing a given set of variable data parameters including various sampled environmental/geochemical conditions and methane gas production rates whereby the program builds the model on the basis that the system has certain associated fixed constraints.

As additional datasets are provided to the program, the sophistication of the model develops and accuracy is refined. Using an optimisation algorithm which processes combinations of data constraints and variables to find the minimum values of certain mathematical functions and/or to find relevant patterns in a dataset to suggest the best theoretical model for any locally provided set of conditions.

This allows, by way of a solution algorithm, a desired output to be interpreted such that information regarding parameters required to produce that endpoint can be provided. An algorithm takes in an input instance of a problem to be solved, and produces output solution to the problem, whereby the mathematical model is solved for the problem instance by the algorithm. An algorithm of solving complementary to the mathematical model is required to provide a procedure for solving the problem by a series of pre-established steps. The nutrient adsorption and/or desorption environmental characteristics associated with the native formation as determined by the sampling one or more formation sampling locations as discussed above, suitably comprises details of one or more of the chemical, physical, geological and microbial ecological conditions associated with any given formation or area within a formation as discussed above.

A model of formation biogenic methanogenesis can be established by collating environmental characteristics of a plurality of real life methanogenesis sites in accordance with the methods described herein.

The collated information concerning the nutrient adsorption and/or desorption environmental characteristics provides guidance as to the most favourable ecological environments required for optimised methane gas production in any given formation whereby the ecological environments of a formation of interest is compared or screen against the collated information. This allows determination of modifications necessary to stimulate and sustain microbial conversion of formation feedstock to methane.

The collected environmental information and the methane gas formation measurements and/or availability of methane gas precursors and/or methanogenic feedstock(s) at each location is then associated with the one or more of the determined chemical, physical, geological and microbial ecological conditions described herein to build up a detailed picture of each methanogenesis environment. As the various sets of environmental conditions are associated with various levels of methane production, the collated information provides a means of understanding and identifying key environmental condition/requirements associated with methanogenesis in a formation. It will be understood that collation of the available information facilitates mapping and/or modelling of the complex interplays between the various chemical, physical, geological and microbial ecological conditions that make up the most favourable environments for methanogenesis.

By building a theoretical model of a biogenic methanogenesis system, the optimum formation environmental conditions for any simulated or studied starting formation of interest can be developed.

The optimum theoretical methanogenesis environments may be modelled using known applied mathematical techniques. Due to the complexity and variability of integers associated with methanogenesis, it will be understood that the modelling studies are computer implemented. It will be further understood that the development of the formation environment amendment regime is also computer implemented, for example, where various algorithms are employed in the optimisation of a formation environment under study towards the theoretical model of methanogenesis.

The modelled system can be applied to the native environmental conditions in a formation of interest to provide a theoretically optimum methanogenesis environment profile for that formation on the basis of available variable in combination with key environments constraints, for example, geology, media present. Using suitable algorithms the native system can be iteratively modified using complex combinations and permutations of the various formation components and characteristics described herein until the lowest energy systems are identified highlighting the optimum tailorable environmental conditional for the formation of interest. Thus, the model can be used to determine ultimately suitability of any given formation under consideration for a biostimulation project.

The identified optimum modelled environment can then effectively be reverse engineered to identify what modifiable integers require adjustment to stimulate the modelled optimum environment conditions in the formation under consideration.

An analysis of the environment conditions associated with the formation provides useful information for comparison with the modelled environmental data to provide an assessment of the factors required for optimised methanogenesis, including determining suitable microbial growth stimulants or in situ environmental conditions for microbial growth. Where the optimised conditions are determined, the adjustments required to match the environment conditions a formation of interest can then be calculated. Typically, the calculation will be carried out by one or more suitable algorithms.

Due to the complexity and interplay of contributing integers to any given set of environmental conditions, one or more suitable algorithms are preferably used to model the optimum theoretical environments.

One or more suitable algorithms are preferably used to generate the model of the methanogenesis system. One or more suitable algorithms are preferably used to apply the model of the methanogenesis system to the variables and constraints associated with a native formation to product a model of a most favourable optimised methanogenesis system.

Furthermore, one or more suitable algorithms are preferably used in the determination of the optimised formation environment from the native formation by application of the formation environment amendment regime of the invention. The algorithms used herein are preferably computer implemented.

The algorithms used herein are preferably adaptive learning algorithms (i.e. an algorithm which uses data from previous monitoring cycle(s) of the indigenous environment to control the current dosage regimen). The accumulation of historical input (initial indigenous environment, discrete changes to same over time, particularly with respect to dosage of known external nutrient compositions) and output (e.g. actual observed methane production and changes in same which result from induced and natural changes in the indigenous environment) enables the stimulation algorithm to "learn" the most efficient means of maintaining and optimising methane production through controlling the rate and composition of the nutrient mixture being dosed depending on the specific characteristics of a particular indigenous environment.

Preferably, the algorithm calculates the proportion of nutrients available to the microbial consortia in the indigenous environment. Preferably, the algorithm draws upon comparative data from different times, microbial consortia and/or carbonaceous material in determination of the desirable characteristics of the first, second and/or subsequent nutrient compositions. In a preferred embodiment, the carbonaceous material is coal and/or carbonaceous shale and the algorithm considers rock characteristics (including maceral composition) to determine the desirable characteristics of the first, second and/or subsequent nutrient compositions. Monitoring the microbial consortia environment preferably includes monitoring the generation of methane, for example, a reduction in the level/amount/volume of methane generated indicates that adjust to the indigenous microbial environment is required. In the broadest sense, this includes the monitoring of methane extracted from the production well. The monitoring of the methane generation is preferably designed to measure the amount of natural biogenic and enhanced biogenic production of methane. This may be performed through establishing a baseline of methane generation prior to the introduction of an initial nutrient composition. Similarly, observation of an inflection point with regard to a change from a maximum of methane generation to a steady reduction of methane generation is indicative that remedial action, such as further nutrient dosing, might be required to boost or enhance flagging biogenic methane production, although there is no reason why such action might be taken prior to the observation of the inflections point as the beneficial effect described would inherently occur, but the degree of resultant methane generation improvement would be less straightforward to quantify.

In a further aspect, the invention provides a method of creating a methanogenesis model for determining optimal methanogenesis conditions in subterranean formations, the process including the steps of:

(a) analysing one or more components of a plurality of formation to determine nutrient adsorption/desorption adsorption and/or desorption environmental characteristics associated each of the plurality of the native formation environment;

(b) detecting a presence of one or more methanogenic microbes within each of the plurality of the formations;

(c) detecting a level of methane gas production occurring within each of the plurality of formations;

(d) using information obtained from steps (a) to (c) to determine a theoretically formation environment modelled for optimised methanogenesis biostimulation efficiency.

It will be understood that the theoretical formation environment modelled for optimised methanogenesis biostimulation efficiency is optimised with respect to biostimulating nutrient adsorption/absorption.

In a further related embodiment, the invention provides a method of creating a methanogenesis model for determining optimal methanogenesis conditions in subterranean formations, the process including the steps of:

(a) analysing one or more components of a plurality of formation to determine biostimulating nutrient adsorption and/or desorption environmental characteristics associated each of the plurality of the native formation environment;

(b) detecting a presence of one or more methanogenic microbes within each of the plurality of the formations;

(c) detecting a level of methane gas production occurring within each of the plurality of formations;

(d) using information obtained from steps (a) to (c) to determine a theoretical formation environment modelled for optimised methanogenesis biostimulation efficiency with respect to biostimulating nutrient adsorption/absorption.

The invention also pertains to a method of creating a methanogenesis model for determining optimal methanogenesis conditions in subterranean formations, the process including the steps of:

(a) analysing one or more components of the formation to determine a set of nutrient adsorption and/or desorption environmental characteristics associated with the formation environment in its native state, wherein the nutrients are one or more biostimulating nutrients which are adsorbable onto, and/or, desorbable from, the one or more components of the formation;

(b) detecting a presence of one or more methanogenic microbes within each of the plurality of the formations;

(c) detecting a level of methane gas production occurring within each of the plurality of formations;

(d) using information obtained from steps (a) to (c) to determine with respect to biostimulating nutrient adsorption and/or desorption that promotes optimal in-situ methanogenesis from the feedstock by the methanogenic microbes a theoretical formation environment modelled for optimised methanogenesis biostimulation efficiency.

In order to build the necessary datasets required for determining the optimum conditions for methanogenesis, the results from sampling over a plurality of formations, and more preferably, over a plurality of diverse formation locations may be collated and continuously build up over extended periods of time. Ideally, sampling will include data from geologically and/or geographically diverse methane generating formations. Historically available data regarding formation conditions and methane generation levels may also be included, if desired, in order to build up the necessary datasets required for modelling and computer implemented analysis described later herein.

The stimulation model preferably will take inputs from multiple samples from a plurality of locations within the methane catchment area. Through taking multiple samples within the catchment area the stimulating model will be more reflective of the indigenous environment, with the stimulation model being based upon multiple input data relating to variations in maceral composition, formation water composition and microbial consortia composition at various locations over different time intervals, thereby providing a dynamic stimulation model in which detected variations in the indigenous environment location may be responded to by using the data (i.e. learning) from a different indigenous environment location and/or time.

Preferably, the above-mentioned samples are taken from both poor and rich methane generating formations so that the characteristics of both types of formation can be included in the modelling studies described herein.

Through better understanding the interaction of the formation water, the carbonaceous medium, the microbial consortia, including their inputs and outputs, the formation environment amendment regime will become optimised relative to the specific requirements of a given methane producing catchment area. In addition to changes in the nutrient composition, the analysis of the indigenous environment may lead to a dosage regimen that varies the amount and frequency of the external nutrient composition to heighten microbial activity.

In a further still aspect, the invention provides a methanogenesis model prepared by the process of the previous aspect.

Determining Optimal Methanogenesis with Respect to Nutrient Dose Present and/or Provided In a further aspect, the invention provides a method for using the methanogenesis model described herein to determine optimal methanogenesis conditions in a subterranean formation, the process including the steps of:

(a) analysing one or more components of the formation to determine nutrient adsorption and/or desorption environmental characteristics associated with the native formation environment;

(b) detecting a presence of one or more methanogenic microbes within the formation;

(c) detecting a level of methane gas production occurring within the formation;

(d) using information obtained from steps (a) to (c) to determine an optimised formation environment that promotes in situ methanogenesis from the feedstock by the methanogenic microbes.

Nutrient Identification

In a further aspect still, the invention provides a use of a methanogenesis model as described here in the determination of one or more nutrients suitable for biostimulation of methanogenesis wherein the nutrient is not urea, ammonia, phosphorous and/or potassium. For example, the model can be used to identify as to date unknown methanogenesis biostimulating nutrients and/or precursors thereof. In a preferred embodiment, the model can be used to identify and/or predict unknown or unexpected alternative nutrients to those traditionally used in methane recovery. Preferably such new or alternative nutrients will be cheaper, and/or more effective and/or less toxic/polluting than existing nutrients. In some embodiments the organic acids are believed to block adsorption sites, while in others they are believed to form acid-base complexes that are less adsorbable that the non-complexed form. Such complexes may favourable modify nutrient mobility to enhance methanogenesis. Similarly, in a related aspect the invention provides a use of a methanogenesis model as described herein in the determination of one or more chemical components suitable for blocking adsorption of one or more methanogenic microbes nutrients onto a subterranean formation component and/or carbonaceous feedstock.

In an embodiment, the invention provides for a use of an amendment compound for adjusting nutrient adsorption and/or desorption in a stimulated biogenic methanogenesis of a carbonaceous feedstock.

Preferably, the amendment compound is either, or both of, urea and one or more of a $C_1$-$C_{10}$ organic acid, and/or precursors thereof.

Desirably, the invention also provides a nutrient amendment formulation for use in a process according to the invention or in a use according to the invention, wherein the formulation comprises:

(i) from about 1-150 mM of one or more $C_1$-$C_{10}$ organic acids;

(ii) an effective amount of one or more of nitrogenous fertilisers; and optionally, (iii) an effective amount of one or more of phosphate fertilisers; and (v) the remainder of water.

The nitrogenous and phosphate fertilisers as defined herein are intended to include all commercially available nitrogenous and/or phosphate fertilisers, particularly those available in bulk qualities for broad acre farming applications and the like.

The nitrogenous fertilisers may include ammonium chloride, urea or combinations thereof.

The phosphate fertilisers may include potassium hydrogen phosphate.

In a preferred embodiment, an exemplary nutrient formulation comprises:

(i) from about 1-150 mM of one or more $C_1$-$C_{10}$ organic acids;

(ii) an effective amount of one or more of ammonium chloride and urea; and optionally, (iii) an effective amount of potassium hydrogen phosphate; and (iv) the remainder of water.

In another preferred embodiment, the organic acids comprises: 10 mM acetic acid, 1 mM tartaric acid. 100 mM acetic acid, and/or 5 mM oxalic acid.

In another preferred embodiment, the organic acids comprises: 10 mM acetic acid and/or 1 mM tartartic acid acid.

Biostimulating Biogenic Methanogenesis

In further aspect the invention provides a process of biostimulating biogenic methanogenesis of a carbonaceous feedstock in a native subterranean formation, comprising the applying a formation environment amendment regime to the native formation environment to increase methanogenesis efficiency with respect to nutrient dose present and/or provided wherein the formation environment amendment regime is developed by the method as described herein for the native subterranean formation.

In one embodiment, the process involves modifying a nutrient dosing plan to account for nutrient bioavailability as determined by a model as described herein.

In a further aspect, the invention provides a method of experimentally modelling nutrient adsorption in subterranean formation bearing a carbonaceous media comprising the step of analysing nutrient adsorption and/or desorption processes in soil under a range of environmental conditions.

This paragraph has been deleted

Figure 10:
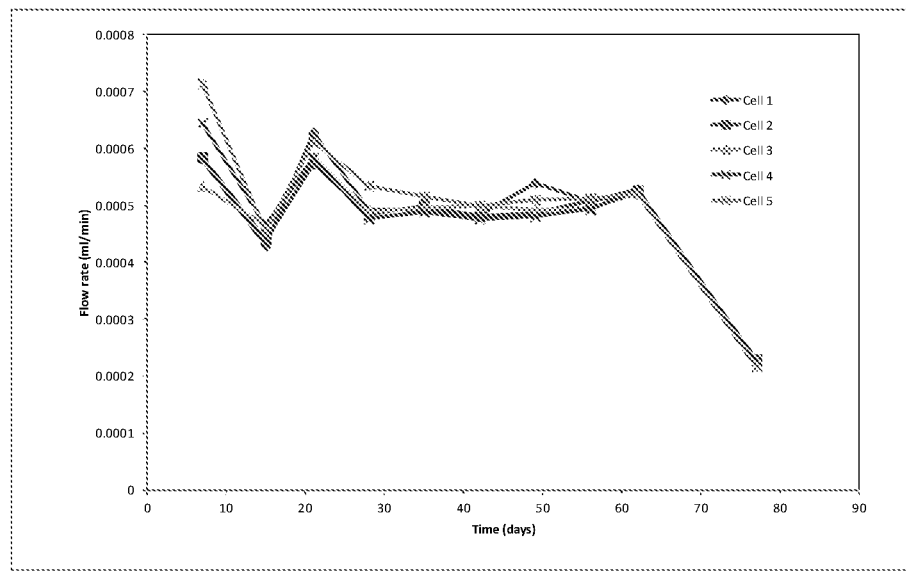

FIG. 10 illustrates the flow rates for the cells in the batch experiment.

Figure 11:
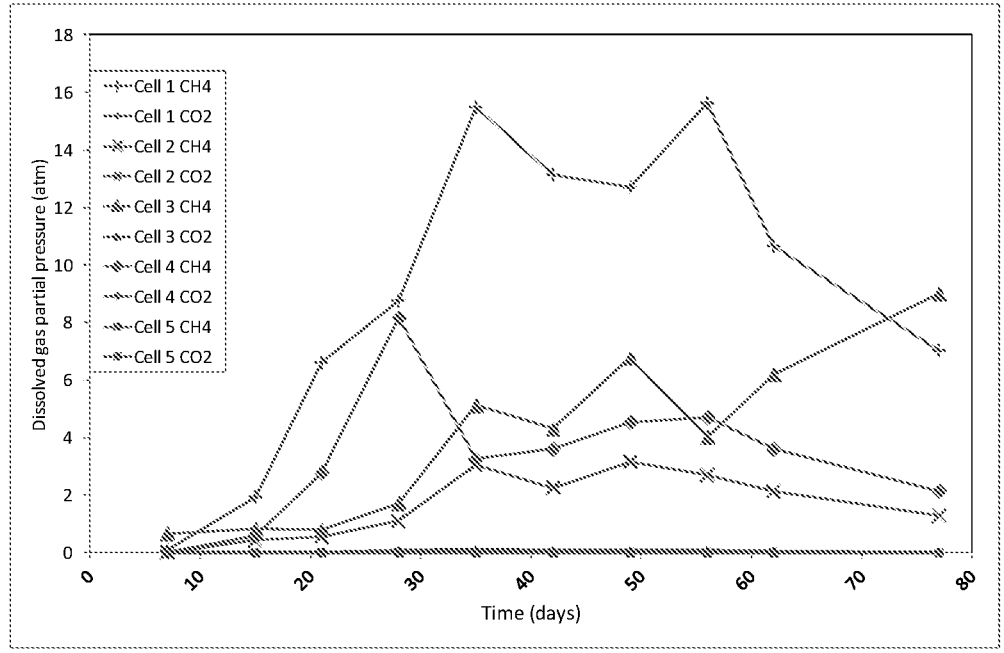

FIG. 11 illustrates the dissolved gas partial pressures during Coal #4 batch experiment.

Figure 12:
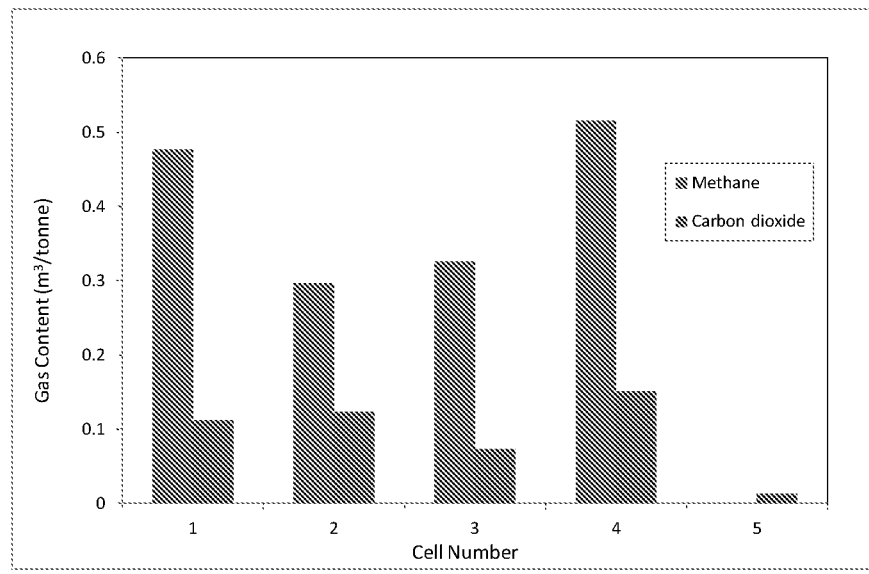

FIG. 12 illustrates the measured gas contents from the Coal #4 batch experiment.

Figure 13:
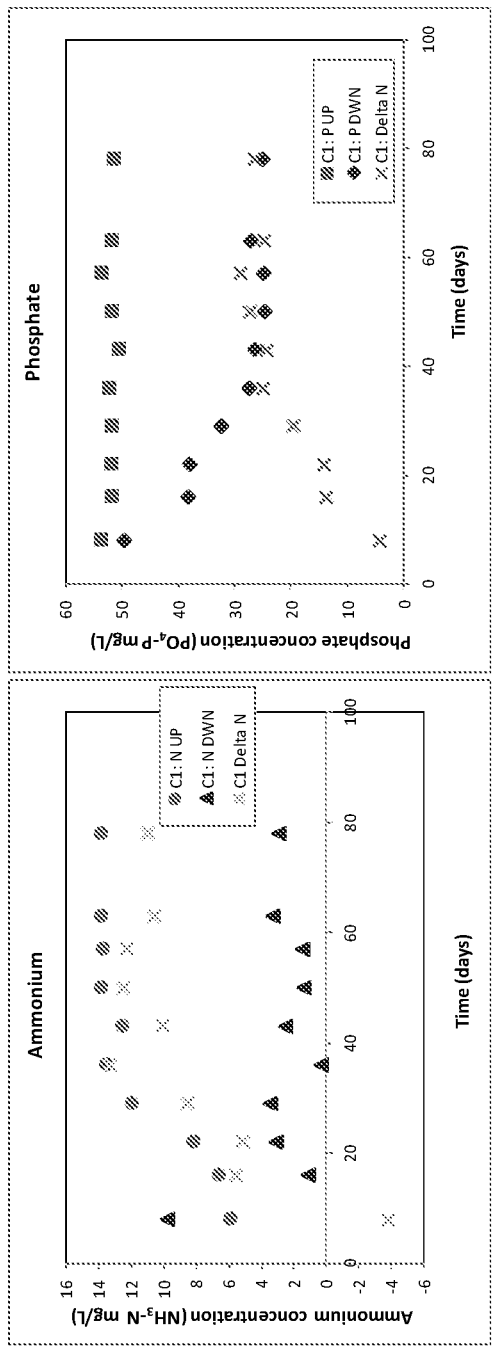

FIG. 13 illustrates the upstream and downstream ammonium (left) and phosphate (right) concentrations over time for Cell 1 from the Coal #4 batch experiments. The figure also presents the difference between upstream and downstream concentration (Delta N and Delta P).

Figure 14:
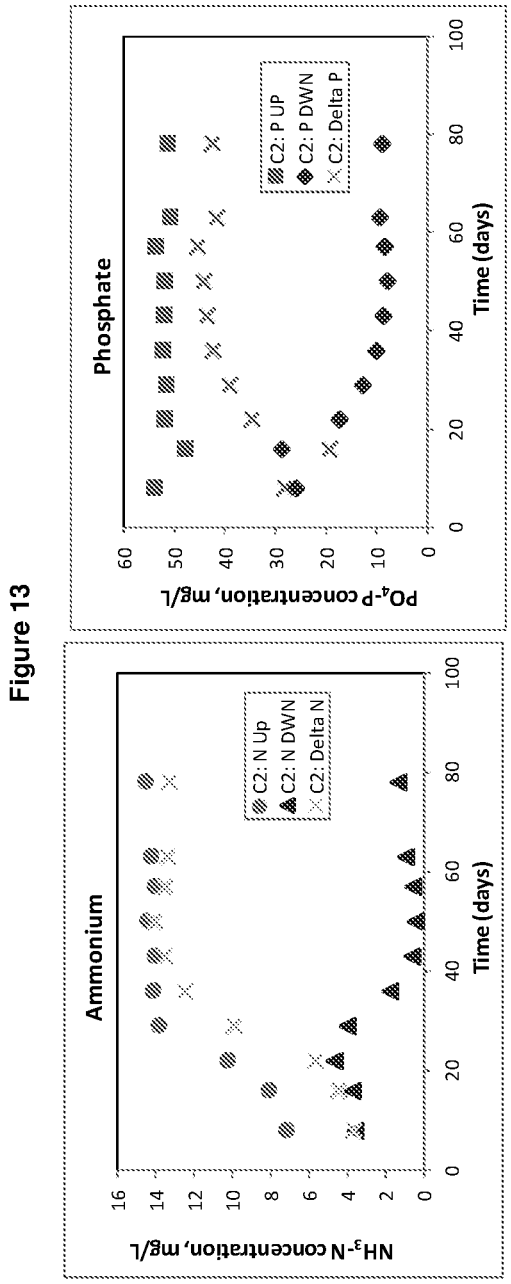

FIG. 14 illustrates the upstream and downstream ammonium (as $NH_3$—N) (left) and phosphate (as $PO_4$—P) (right) concentrations over time for Cell 2 from the Coal #4 batch experiments. The figure also presents the difference in upstream and downstream concentration (Delta N and Delta P).

Figure 15:
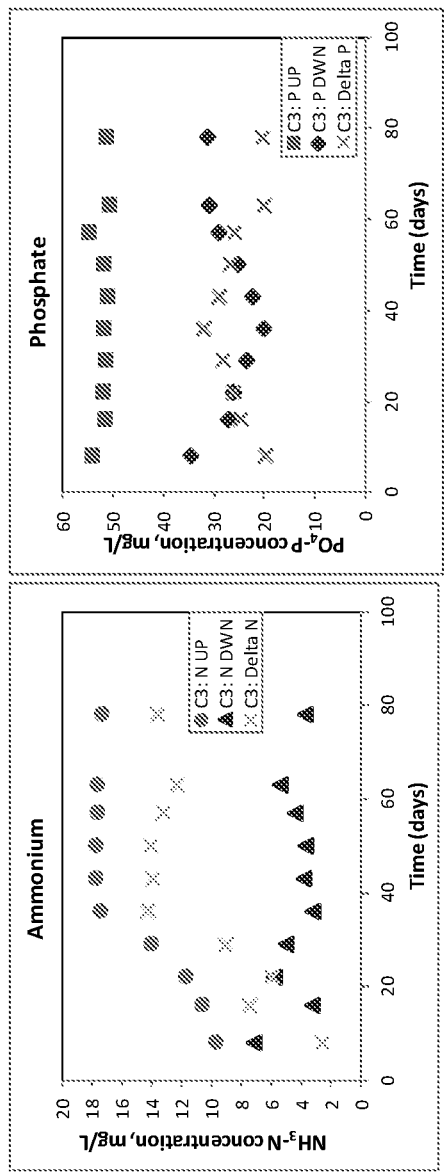

FIG. 15 illustrates the upstream and downstream ammonium (as $NH_3$—N) (left) and phosphate (as $PO_4$—P) (right) concentrations over time for Cell 3 from the Coal #4 batch experiments. The figure also presents the difference in upstream and downstream concentration (Delta N and Delta P).

Figure 16:
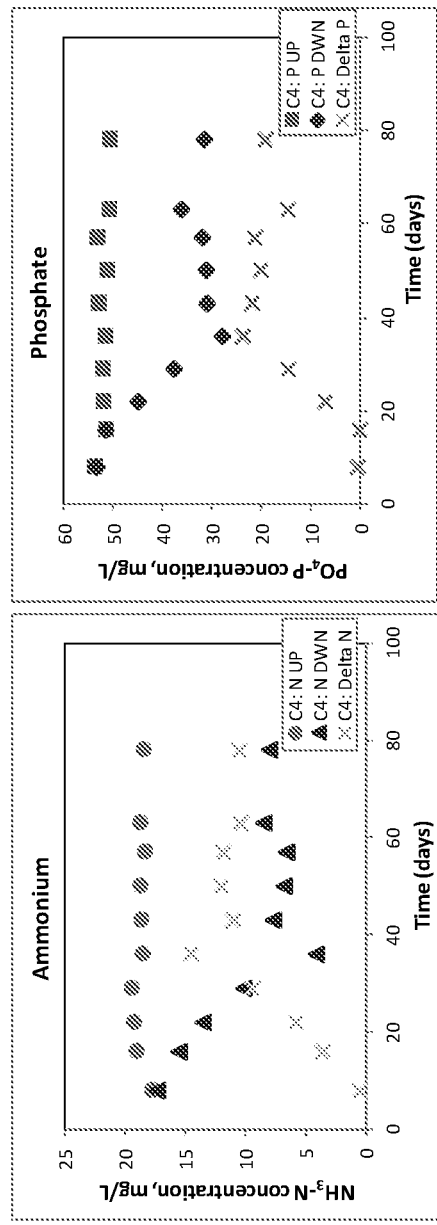

FIG. 16 illustrates the upstream and downstream ammonium (as $NH_3$—N) (left) and phosphate (as $PO_4$—P) (right) concentrations over time for Cell 4 from the Coal #4 batch experiments. The figure also presents the difference in upstream and downstream concentration (Delta N and Delta P).

Figure 17:
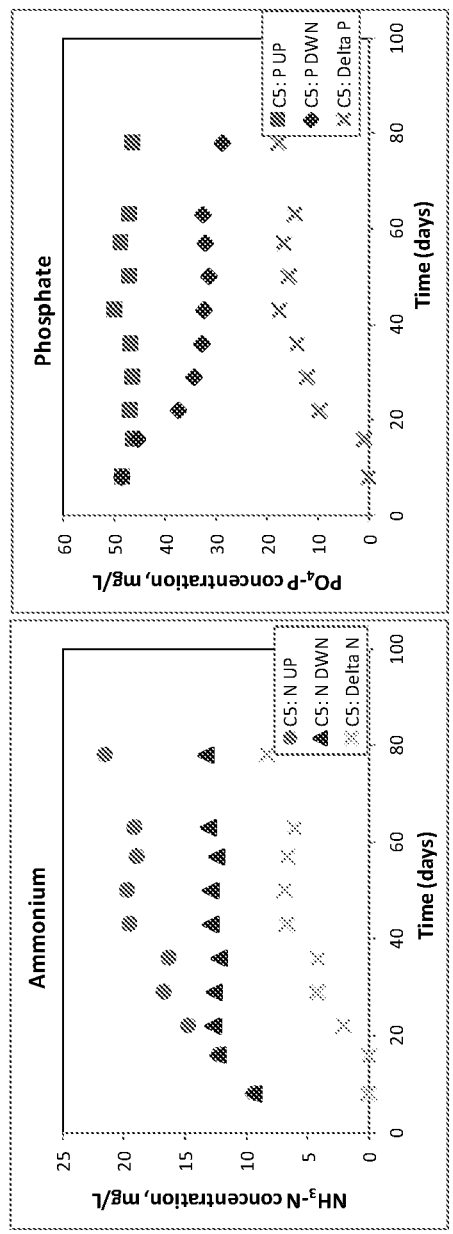

FIG. 17 illustrates the upstream and downstream ammonium (as $NH_3$—N) (left) and phosphate (as $PO_4$—P) (right) concentrations over time for Cell 5 from the Coal #4 batch experiments. The figure also presents the difference in upstream and downstream $NH_3$—N concentration (Delta N and Delta P).

Figure 18:
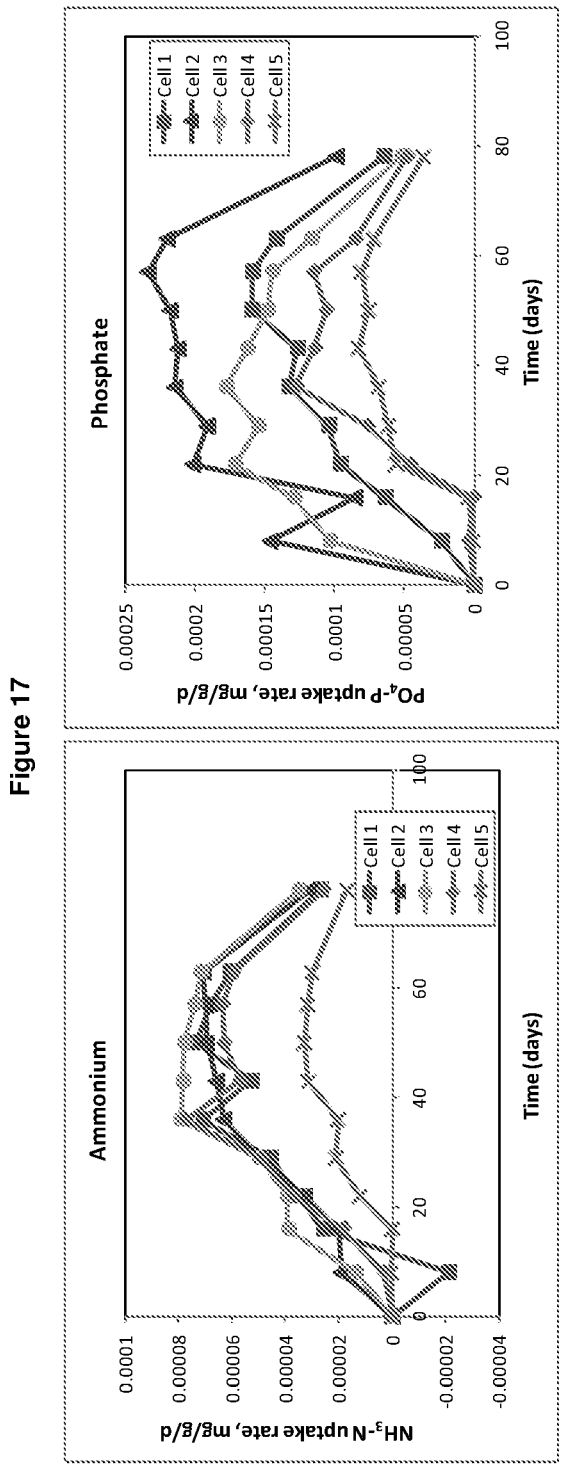

FIG. 18 illustrates the uptake rate of ammonia (as $NH_3$—N) (left) and phosphate (as $PO_4$—P) (right) consumption over time for Coal #4 batch experiments.

Figure 19:
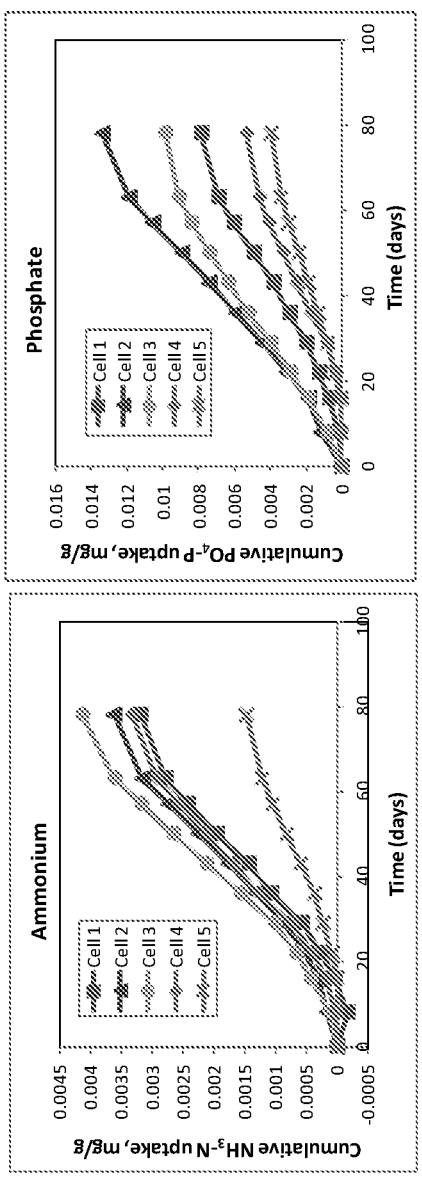

FIG. 19 illustrates the cumulative ammonia (as $NH_3$—N) (left) and phosphate (as $PO_4$—P) (right) consumption over time normalised by the coal mass for Coal #4 batch experiments.

Figure 20:
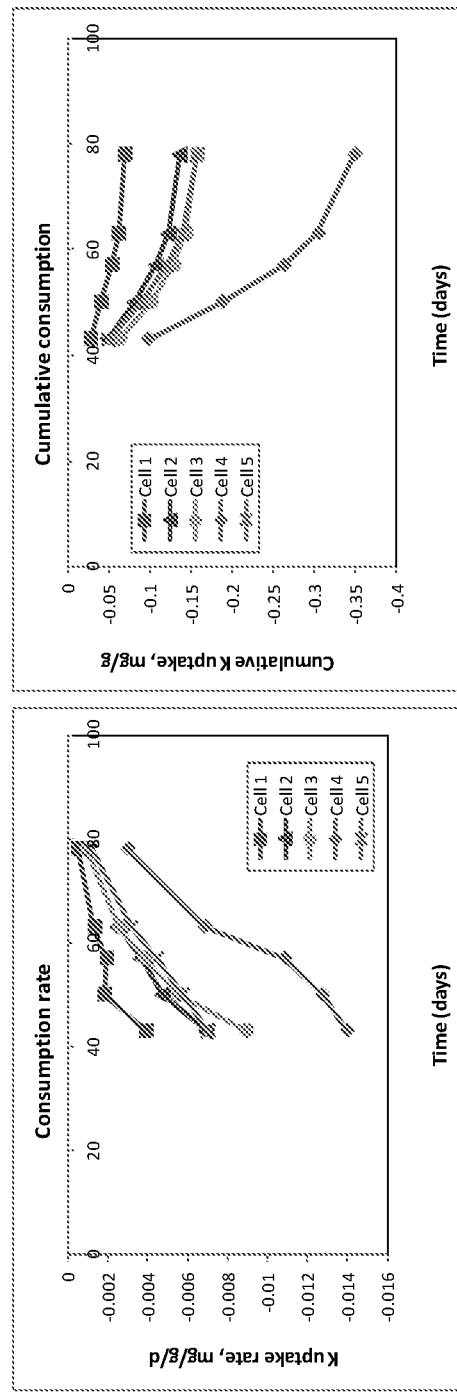

FIG. 20 illustrates the rate (left) and cumulative (right) potassium consumption over time normalised by the coal mass for Coal #4 batch experiments.

Figure 21:
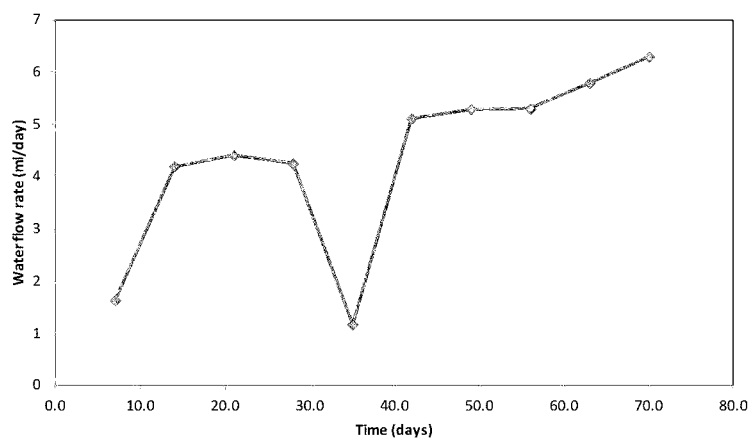

FIG. 21 illustrates the water flow rates for the Coal #5 core flood.

Figure 22:
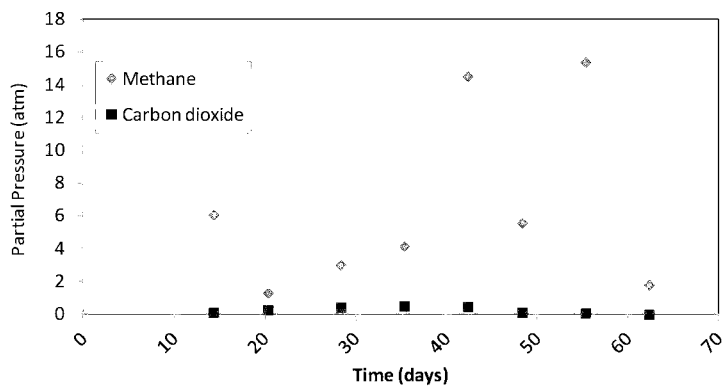

FIG. 22 illustrates the partial pressure of dissolved gases within the outflow water samples during the core flood with Coal #5.

Figure 23:
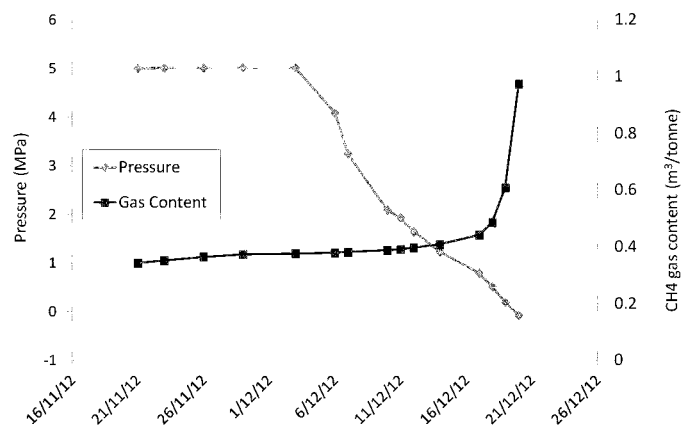
Figure 24:
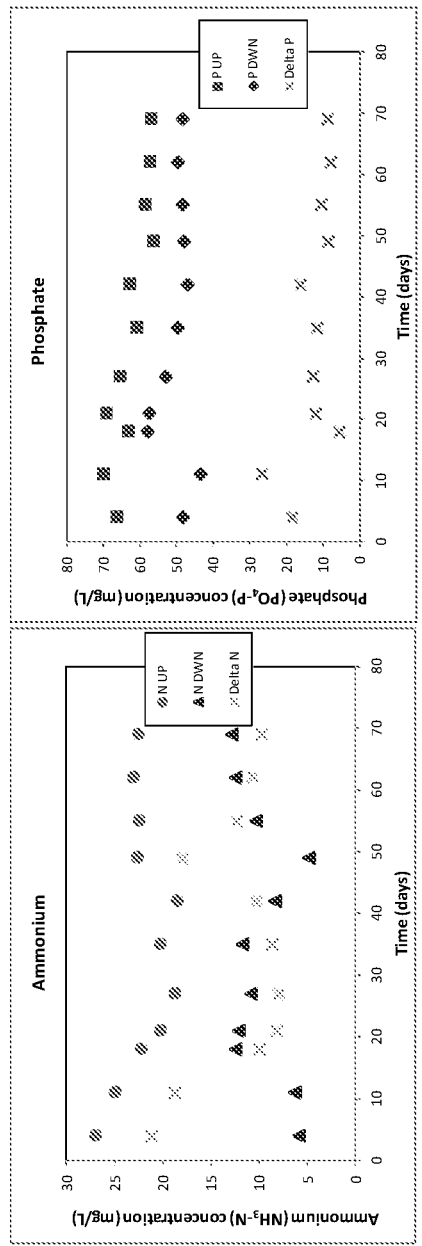

FIG. 23 illustrates the cumulative methane recovered from Coal #5 after the nutrient amended formation water flood as the pore pressure (presented on a gauge basis) is drawn-down FIG. 24 illustrates the upstream (labelled UP) and downstream (DWN) ammonium (left) and phosphate (right) concentration over time for the Coal #5 core flood. The figure also presents the difference in upstream and downstream concentrations (labelled Delta N and Delta P).

Figure 25:
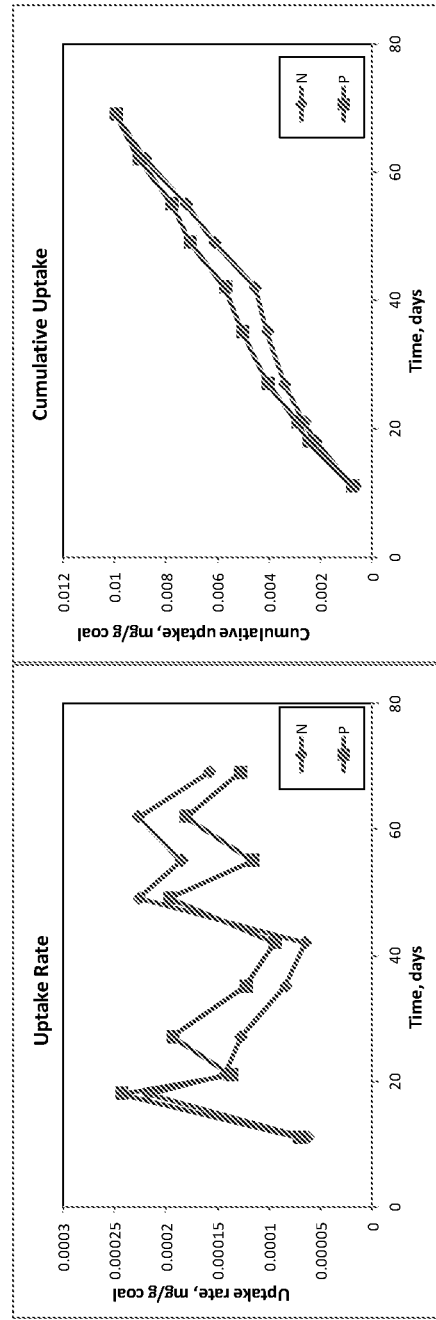

FIG. 25 illustrates the nutrient uptake rate (left) and cumulative nutrient uptake (right) normalised by the coal mass with time for the Coal #5 core flooding experiment (blue: $NH_3$—N, red: $PO_4$—P).

Figure 26:
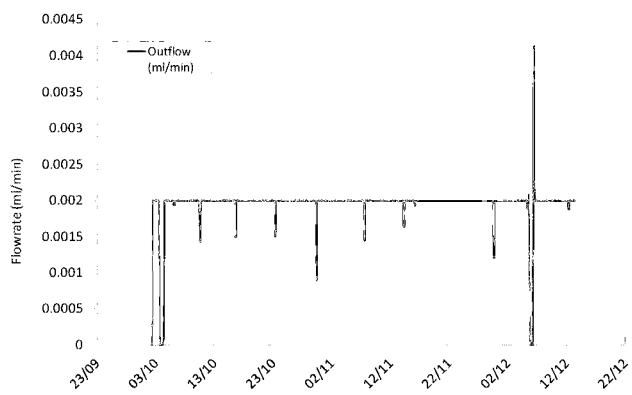

FIG. 26 illustrates the flow rates during Coal #4 core flood; the periodic sharp changes in the rate were due to water sampling.

Figure 27:
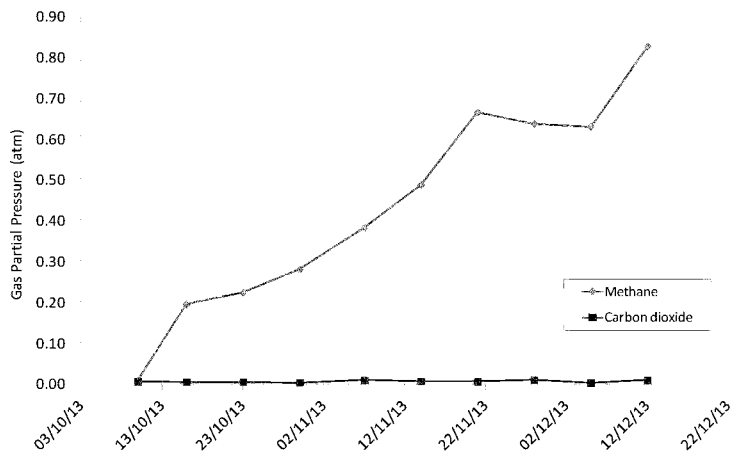

FIG. 27 illustrates the dissolved gas concentration from water samples expressed as partial pressures during Coal #4 core flood.

Figure 28:
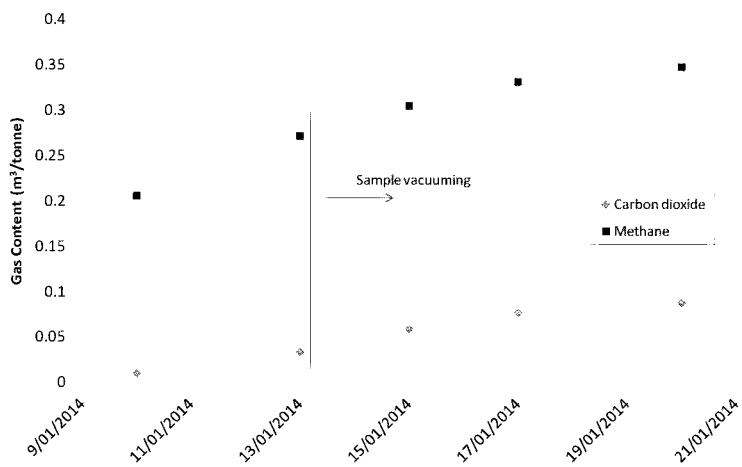

FIG. 28 illustrates the $CH_4$ and $CO_2$ gas content from gas generation during the Coal #4 core flood derived from degassing of the coal at the end of the experiment.

Figure 29:
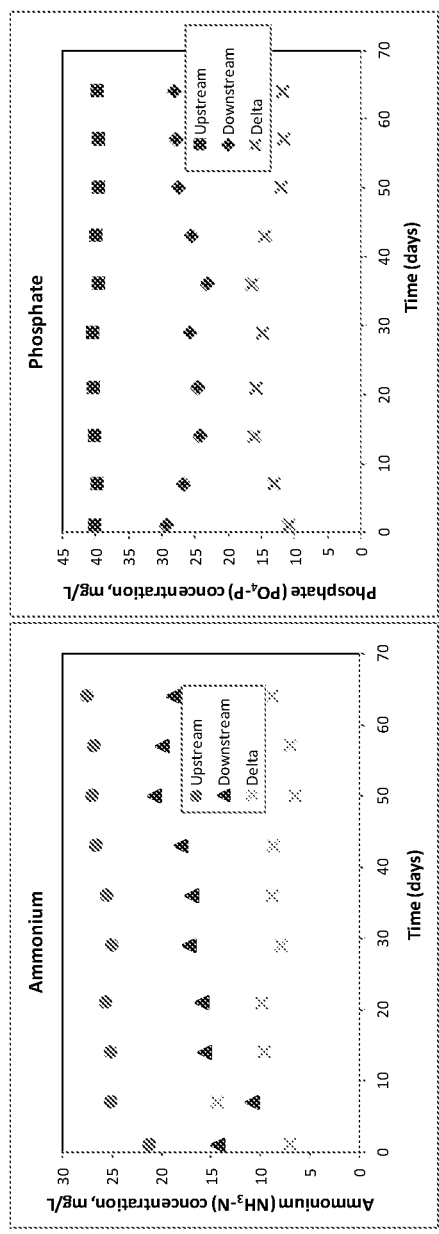

FIG. 29 illustrates the upstream and downstream ammonium (left) and phosphate (right) concentration over time for the Coal #4 core flooding experiment. The figure also shows the difference in upstream and downstream concentration (labelled Delta in the figures).

Figure 30:
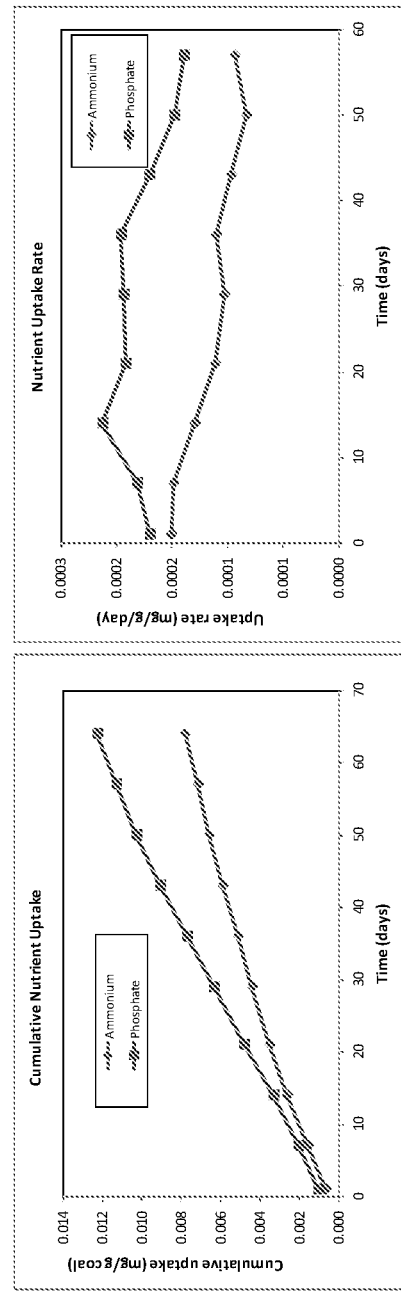

FIG. 30 illustrates the nutrient uptake rate (right) and cumulative nutrient uptake (left) normalised by the coal mass over time for the Coal #4 core flooding experiment.

Figure 31:
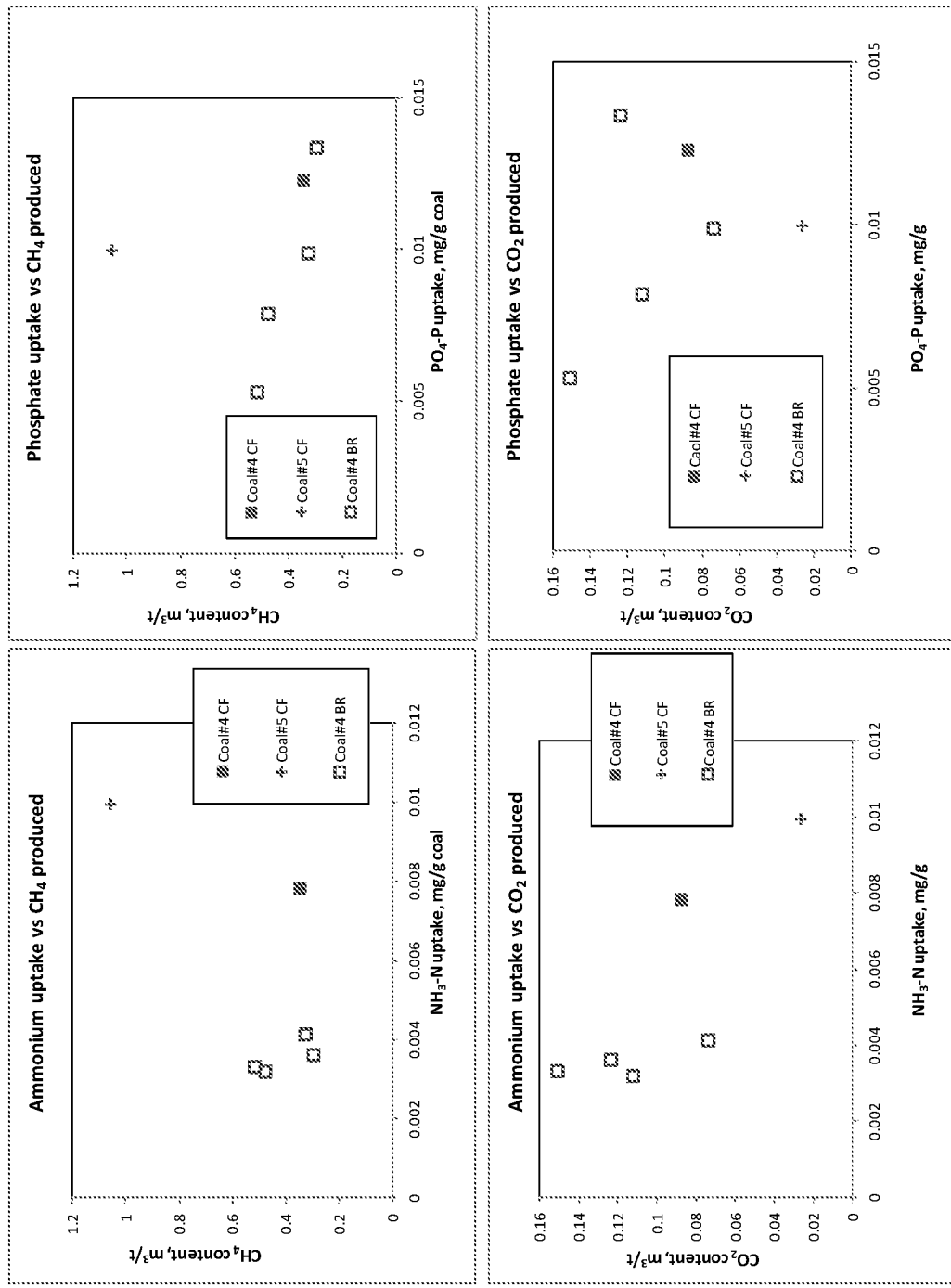
Figure 34A:
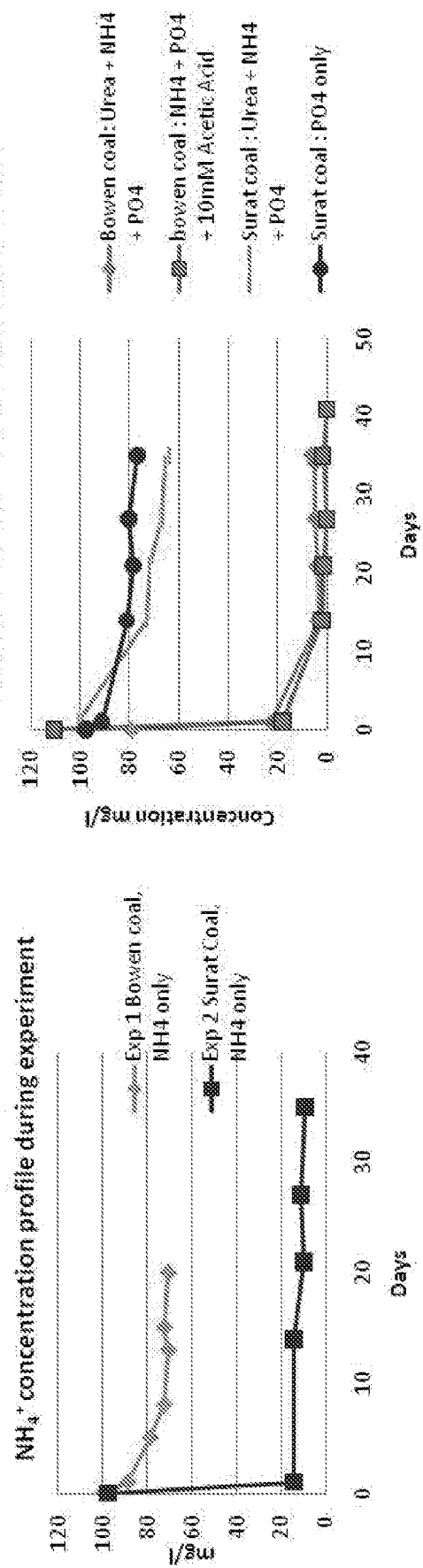
Figure 34B:
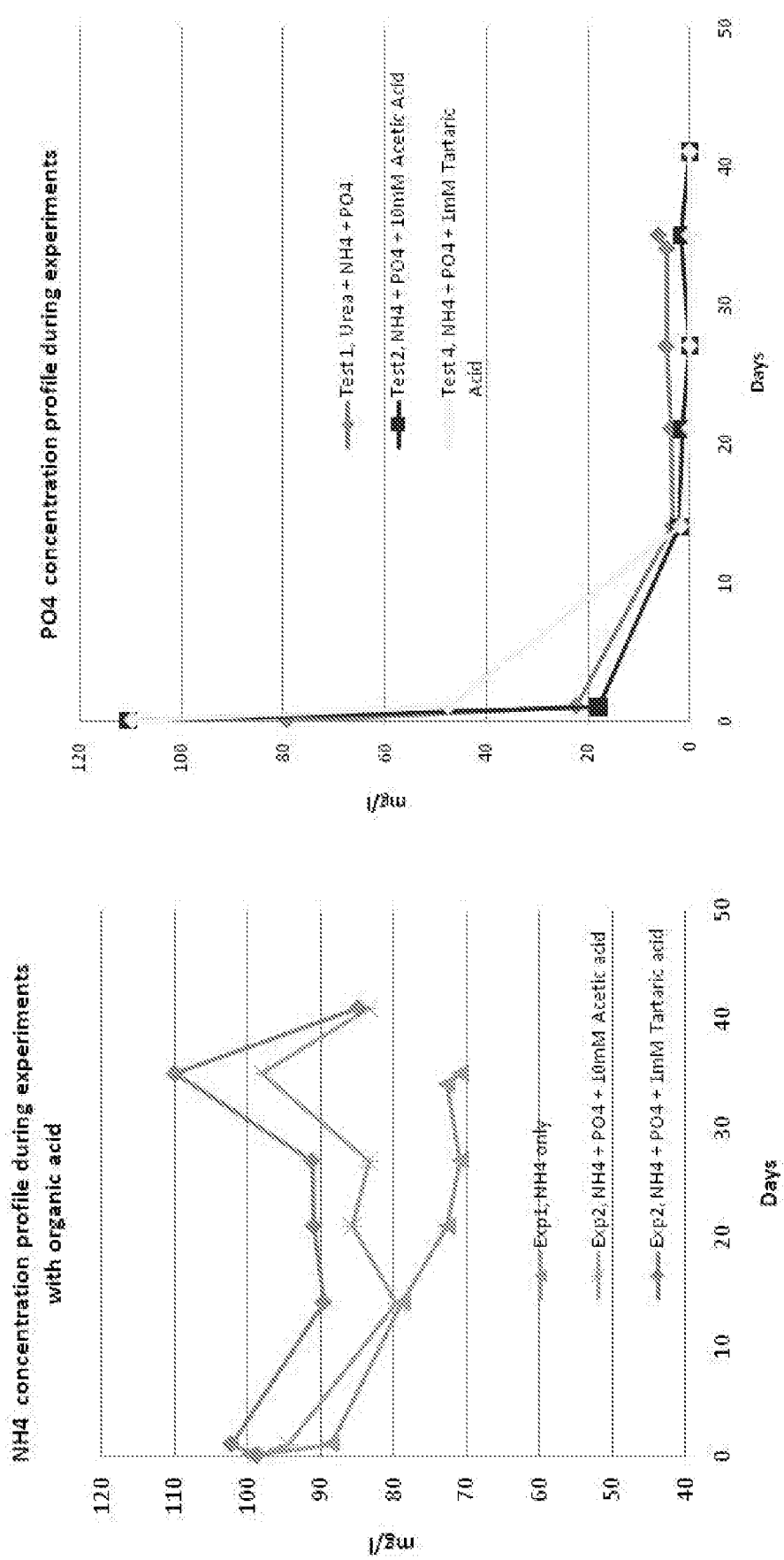
Figure 34C:
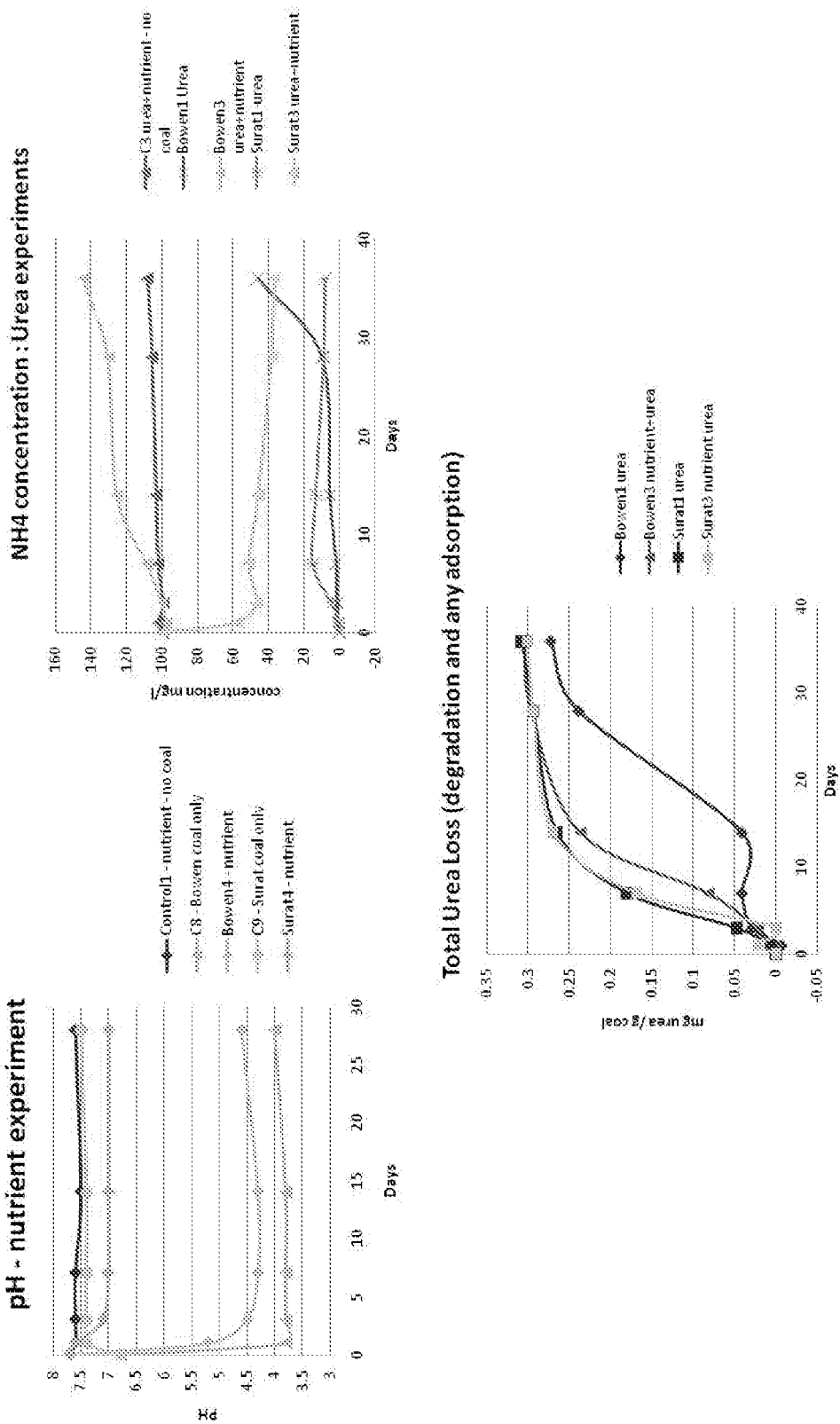
Figure 34D:
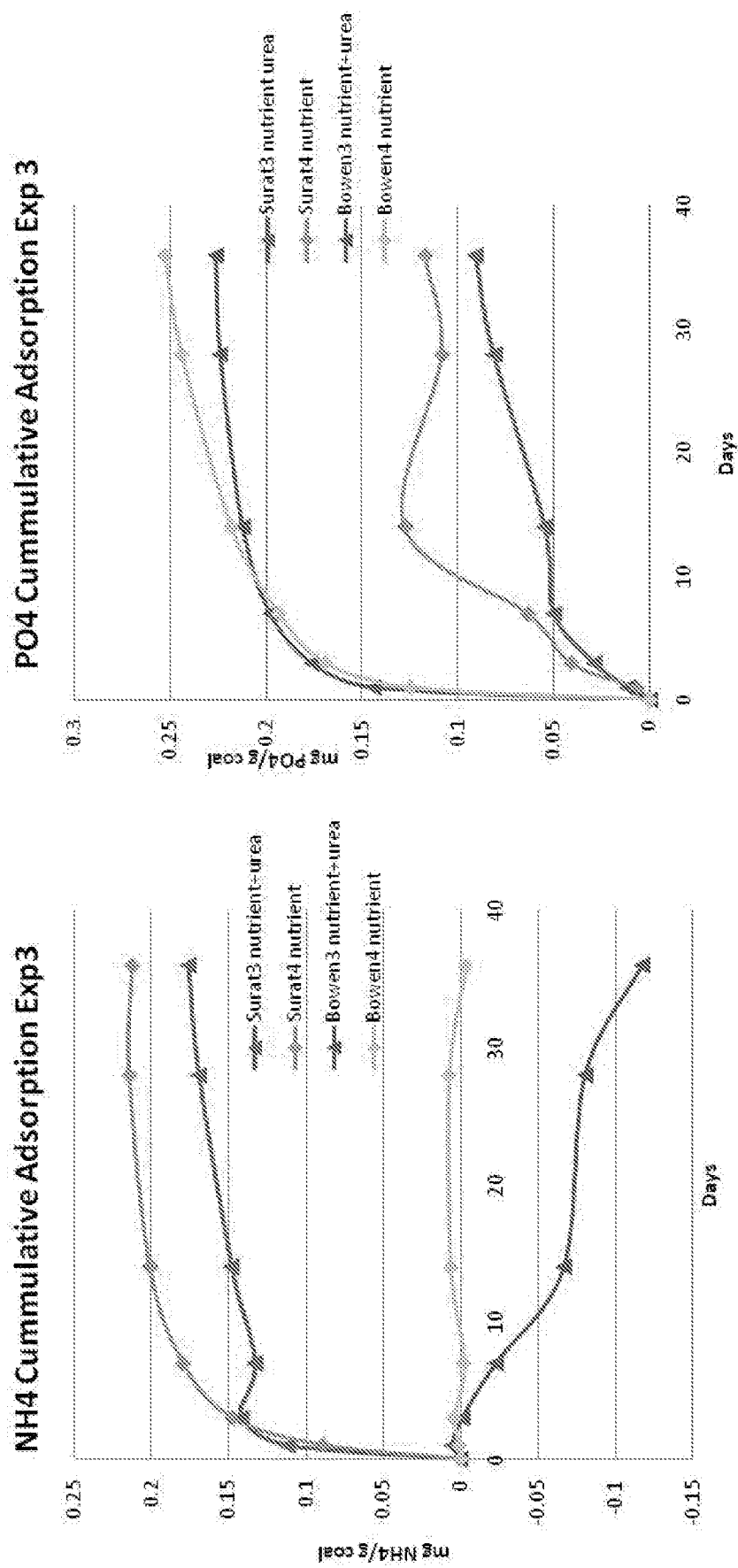
Figure 34E:
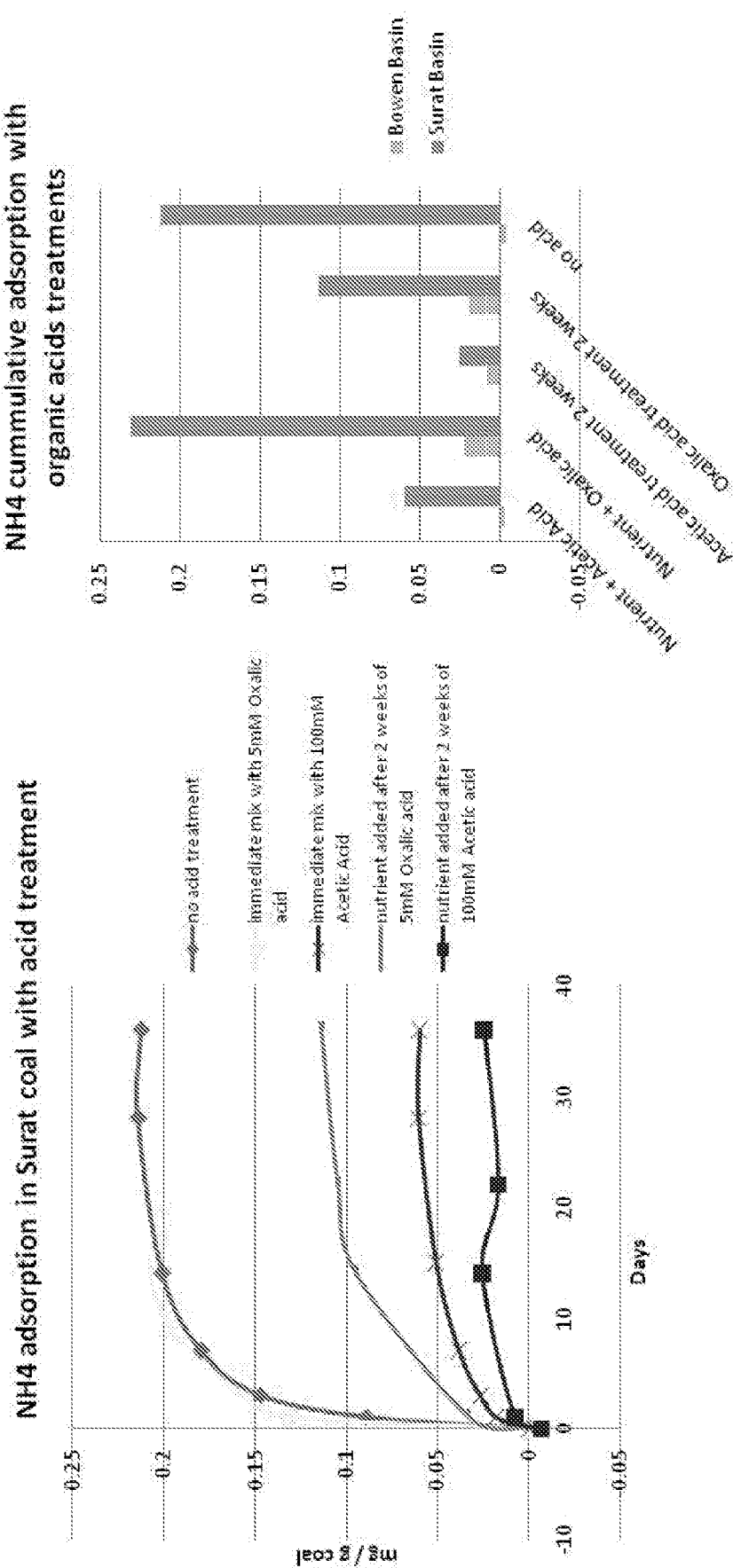
Figure 34F:
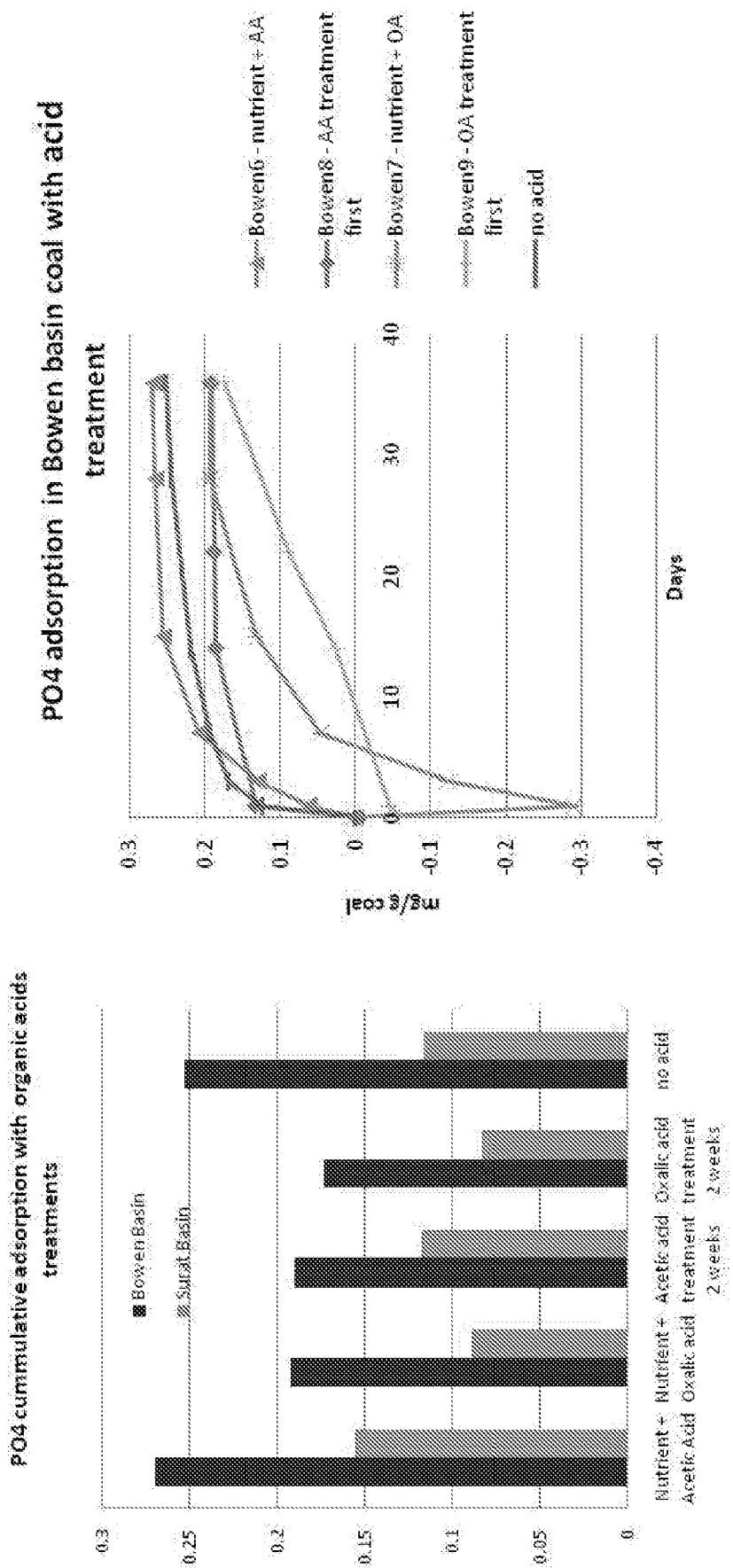

FIG. 31 illustrates the volumes of $CH_4$ (top) and $CO_2$ (left) generated as a function of ammonium (left) and phosphate (right) consumption for the Coal #4 core flooding and batch experiment and the Coal #5 core flooding experiment (the legend labels are BR for the batch experiments and CF for the core flooding experimental.

FIGS. 32, 33, 34a-f illustrate the results of the effect of urea on adsorption.

This paragraph has been deleted.

Figure 35:
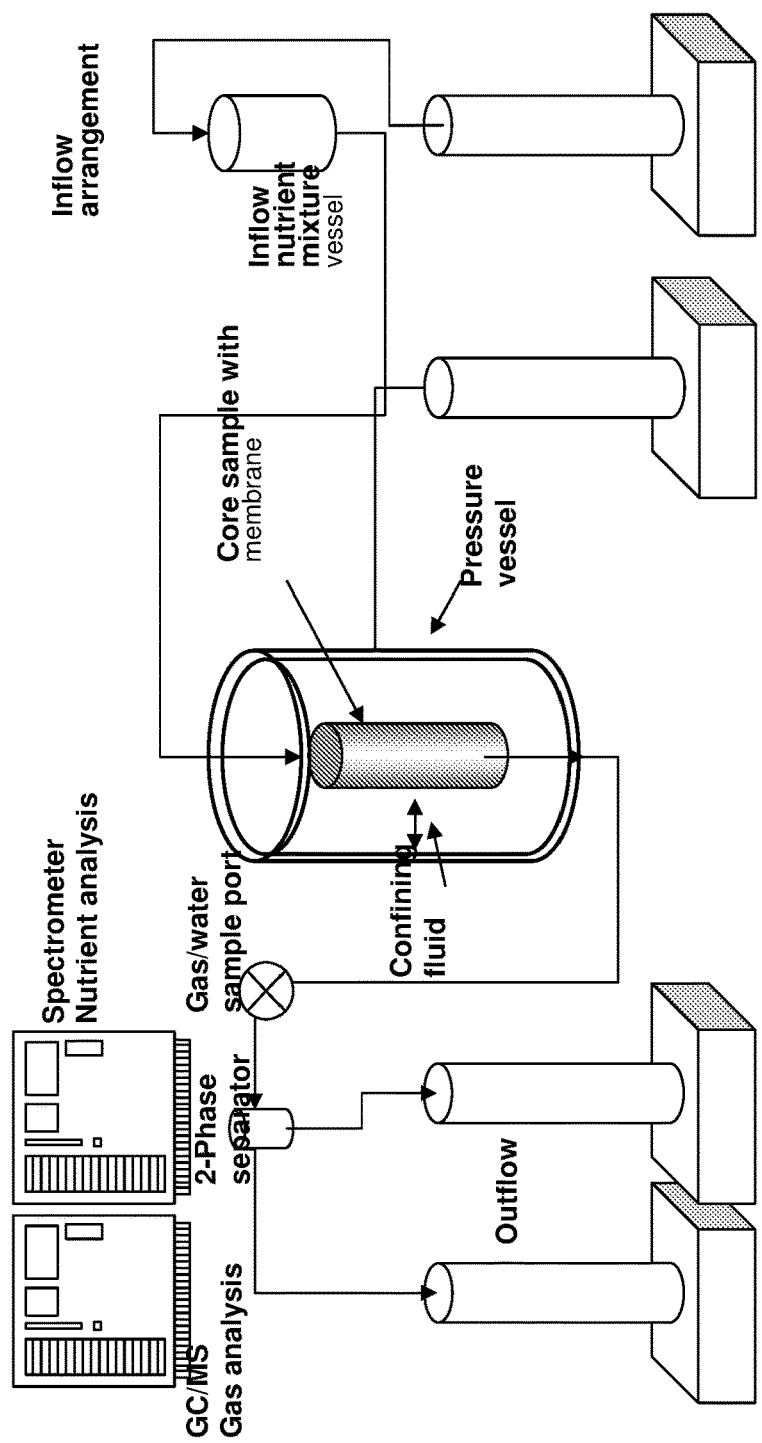

FIG. 35 is a schematic of the rig used in the core flooding experiments.

DETAILED DESCRIPTION OF THE INVENTION

Formation Water Analysis

The formation water may be collected, and analysed in accordance the methodology described in U.S. Pat. No. 6,543,535, the relative parts of which are incorporated herein by reference, and in particular concerning the sections headed Step 1 describing 'Collecting Samples', Environmental Analysis, Microbial Analysis, etc. The teachings in this document provide the skilled person with sufficient information to allow formulation of suitable nutrient compositions for the specific microbes used/described herein.

Sampling

Details of a number of means for sampling are described in U.S. Pat. No. 6,543,535 whereby samples can be obtained from the formation through one or more wells in communication with the formation, such that the concentration and type of microorganisms in the fluid as well as the concentration of stimulants and microbial products in the fluid can be assessed.

Suitably, sampling typically involves removing a fluid, media, rock, sediment and/or gas samples from perforations in a well casing or from open-hole tests provided in the formation. The materials can be sampled either downhole with a wireline formation fluid tester or fluid sampler or at the surface wellhead from a subsurface test, such as drill stem tests, production tests, or normal production. Both formation water and hydrocarbon samples are useful for evaluation of the formation environment. Rock samples can be retrieved from drill cores, cuttings, produced sediments (including bailed samples) and/or outcrop sites or rock data can be secured by interpretation of well logs. Sampling methods are well known in the art.

Sampling frequency may also be determined in accordance in a way that is most economical sensible for a particular sensing method used, however, in general it would be desirable to sample as frequently as possible.

Sensors may be used to monitor the native environment with automated sensors, for example, sensors capable of monitoring the environmental or gas production parameters described herein, will be used to monitor the indigenous environment. The ability to provide data on the indigenous environment at small time intervals, for example, achievable via use of inline, substantially continuous monitoring, will increase the robustness and/or adaptability of the stimulation model described elsewhere herein. In some preferred embodiments, sampling is preferably effectively substantially continuous to the limit of any analytical instrumentation used in the sampling/analysis determination. In any case, the period of time for incubation and/or monitoring/sampling will be dependent upon the initial native environment including the state of any native microbial consortia suitable for methane formation. As such, the elapsed times will be dictated by the results of the monitoring/sampling, and in particular, observation of a decrease in the amount/rate methane being produced over a given time interval for any particular system.

Sampling intervals will typically vary from substantially continuously, to sampling over a set second, minute, hourly, daily, weekly, fortnightly, monthly or yearly interval. In one embodiment, for example, involving laboratory simulation or modelling, the sampling interval can be based shortly scale, for example, over a set second, minute, hourly, daily, weekly, fortnightly, monthly interval. However, in the field, longer sampling periods may be sufficient for example, weekly to 6 monthly, with sampling at least every 1 to 3 months preferred. The optimum sampling period within a given incubation period will depend on the dynamics of a given formation/field. More rapidly changing environments will benefit from more frequent sampling, while conversely, slower changing environments can be sampled less frequently.

Alternatively and/or in addition to, regular sampling of the catchment area may be employed to provide additional data and to calibrate sensors, where required.

It will be understood that data regarding methane production levels should be simultaneously collected, preferably, with reference to each sampling point.

As described in U.S. Pat. No. 6,543,535, other geochemical analyses may also be performed to assess the effectiveness of the stimulants on the formation environment.

Suitable analytical techniques for the analysis of feedstock, such as coal, include: ASTM D2799-13: Standard test method for microscopical determination of the maceral composition of coal; ASTM 2798: Test method for microscopical determination of the vitrinite reflectance of coal; ASTM: Test Methods for Total Sulfur in the Analysis Sample of Coal and Coke; Standards Association of Australia (1998). In AS 2856.2-1998 (R2013) Coal petrography—Maceral analysis, 35 pp; Standards Association of Australia. (2000a). In AS 2856.3-2000 Coal Petrography Method for Microscopical Determination of the Reflectance of Coal Macerals 22 pp and also for proximate and elemental analyses; Australian Standards AS 1038.1, AS 1038.3, AS 1038.6.1, AS 1038.6.2, AS 1038.6.3.3 and AS 1038.11. Microbial analysis and/or characterisation can be carried out using known DNA techniques. U.S. Pat. No. 6,543,535 provides a description of a number of suitable identification/characterisation methods.

Nutrients

For example, the nutrient composition used herein as part of a formation environment amendment regime may further comprise at least one trace element selected from the group comprising iron, manganese, cobalt, zinc, molybdenum, nickel, aluminium, boron, copper, tungsten and selenium. The trace element may be present in the nutrient composition as an aqueous soluble salt thereof. The concentration of each trace element in the nutrient composition may be less than 200 ppm.

In other embodiments the nutrient composition may further comprise at least one vitamin selected from the group comprising pyridoxine, aminobenzoic acid, pantothenate, nicotinic acid, riboflavin, thiamine, thioctic acid, biotin, folic acid, pyruvate, and $B_{12}$. The concentration of each vitamin in the nutrient composition may be less than 100 ppm.

In further embodiments the nutrient composition may further comprise at least one stimulant. Stimulants may be any factors that can be used to increase or stimulate the biogenic production of methane in the carbonaceous material. Examples of stimulants include, but are not limited to, yeast extract, Coenzyme M, lactic acid, mineral amendments (such as chloride, sodium, potassium, magnesium and calcium), alkyl alcohols, methanol, ethanol, 2-propanol, 2,3 butanediol, vanillate, glycine, cysteine, 3,4,5-trimethoxybezoate, cellulose, cinnamic acid, benzoic acid, chitin, chitosan, chlorate, perchlorate, and any combinations thereof.

Other additives may also be included in the nutrient composition for various purposes, for example, to stabilise the nutrient composition against deterioration over time and prolong shelf life, maintain constant pH, and so forth. Such additives may include, but are not limited to, acids, bases, buffering agents, oxidants, anti-oxidants, surfactants, emulsifying agents, gelling agents, any combination thereof and the like.

The source of phosphorus in the nutrient composition may be any substance containing phosphorus in a form that is bioavailable to the one or more methanogenic microbial populations and has the effect of stimulating the biogenic production of methane. The method of determining whether a particular source of phosphorus has a stimulatory effect is well known to those skilled in the art.

In various embodiments, the source of phosphorus may be phosphorus containing compounds such as salts of phosphorus oxoacids, phospholipids or derivatives thereof, organophosphate esters, pyrophosphates and any combination thereof and the like. Preferred pyrophosphates include for example, hydrogen pyrophosphate, calcium pyrophosphates, thiame pyrophosphates, zinc pyrophosphate, sodium pyrophosphate, ammonium pyrophosphate or combinations thereof. In some embodiments, ammonium pyrophosphate is preferred as it also functions as a source of ammonium nutrient.

Examples of suitable salts of phosphorus oxoacids including, but not limited to, salts of hypophosphorus acid ($H_3PO_2$), phosphorus acid ($H_3PO_3$), metaphosphorus acid ($HPO_2$), orthophosphorus acid ($H_3PO_3$), metaphosphoric acids (($HPO_3)_n$), polyphosphoric acids (($HPO_3)_{n+2}$), tripolyphosphoric acid ($H_5P_3O_{10}$), pyrophosphoric acid ($H_4P_2O_7$), orthophosphoric acid ($H_3PO_4$), and the like.

Examples of suitable phospholipids include, but are not limited to, lecithin wet gum, lecithin, cephalin, phosphatidate, phosphatidylserine, phosphatidylinositol, phosphatidylinositol phosphate, phosphatidylinositol bisphosphate, phosphatidylinositol triphosphate, ceramide phosphorylcholine, ceramide phosphorylethanolamine, ceramide phosphorylglycerol, and the like.

Examples of suitable phospholipid derivatives include, but are not limited to, natural phospholipid derivatives found in eggs, soy, hydrogenated soy, or synthetic phospholipid derivatives of phosphatidic acid, phosphatidylcholine, phosphatidylglycerol, phosphatidylethanolamine, phosphatidylserine, PEG phospholipids, and the like.

Examples of suitable organophosphate esters include, but are not limited to, trixylenyl phosphate ester, butylated phenol phosphate ester, isopropyl phenol phosphate ester, and the like.

The source of nitrogen in the nutrient composition may be any substance containing nitrogen in a form that is bioavailable to the one or more methanogenic microbial populations.

In various embodiments, the source of nitrogen may be an inorganic nitrogen compound such as nitrogen hydrides and salts thereof, nitrogen oxoacids and salts thereof, urea, carbamide, hydroxylamine, ammonium chloride, sulfamide, thiocyanate salts, any combination thereof and the like. Examples of suitable nitrogen hydrides include, but are not limited to, ammonia, azanes such as hydrazine, triazane and so forth, diazene, trizene, and the like. Examples of suitable salts of nitrogen oxoacids include, but are not limited to, salts of hyponitrous acid ($H_2N_2O_2$), nitrous acid ($HNO_2$), nitroxyl (HNO), nitric acid ($HNO_3$), peroxynitrous acid ($HONO_2$), any combination thereof and the like.

In other embodiments, the source of nitrogen may be an organic nitrogen compound such as amines and ammonium salts thereof, amides, amino acids, peptides, oligopeptides, proteins, any combination thereof and the like.

In alternative embodiments, the source of nitrogen may be a nitrogen compound which is a gas phase at ambient temperature and pressure. Said gaseous nitrogen compounds may also be soluble in aqueous solutions at ambient temperature and pressure. Illustrative examples of such gaseous nitrogen compounds include ammonia, nitrogen, and nitrogen oxides. In particular when the nutrient composition may be employed to enhance methanogenic production of methane in subterranean formations bearing carbonaceous material, it is anticipated that the solubility of said gaseous nitrogen compounds in the nutrient composition is likely to increase in response to increased temperature and pressure in said subterranean formation. For example, further discussion of such gaseous nutrients and other nutrients can be ascertained by consulting the relevant discussion in U.S. Pat. Nos. 9,783,829 and 9,796,908, the contents of both of which are herein incorporated by reference.

It will be understood by the person skilled in the art that suitable sources of phosphorus or nitrogen may vary dependent upon the methanogenic microbial population and the carbonaceous material. The selection of suitable sources of phosphorous and nitrogen may be readily performed through a screening process in which the effectiveness of various nutrient compositions is tested upon specific carbonaceous material and methanogenic microbial populations.

Adjusting Biostimulant Adsorption/Desorption

Laboratory scale simulations can also be prepared to test a theoretical formation environment amendment regime to establish likely effectiveness at promoting methanogenesis. For example, samples of the indigenous microbial consortia can be grown in various nutrients using a range of nutrient media, with varying pH, salinity, trace metals, and electron acceptors to find those conditions which support high rates of degradation and methanogenesis. These culture studies may involve several cycles of stimulant additives and stimulant combinations as well as environmental conditions (e.g. salinity, temperature, pH, etc.). In these studies, the degree nutrient adsorption onto carbonaceous feedstock can be assessed and the best methods for compensating for reduced bioavailability can be determined.

Formation Conditions

Where methane productions levels are zero or less than required for commercial viability, it is generally because the required consortia are not present, are not in an optimised state and/or the environmental conditions in the formations are not conducive to support and flourishing of the required microorganism consortia.

As explained above, where the model/algorithm based comparative analysis indicates that a particular species of flora are required, the amendment can be a bioaugmentation amendment whereby desirable extraneous bacteria can be introduced with supporting nutrition and/or trace elements/minerals where useful to support the added bacteria colonisation.

Typically formation fluids have a temperature less than about 130° C., a pressure less than about 10,000 psig, pH of from about 3-10, and a salt concentration in the order of about 300,000 ppm.

Adjusting conditions can be effected by amending one or more of the formation temperature, pH, mineralogy, and salinity and gas content of, for example, $CO_2$, $O_2$, and $H_2$ in the formation.

Injection Process

Environment condition amendments can be implemented by injection of one or more adjusting components into the formation, for example, in the form of a fluid (solution or gas), polymer, particulate or combinations thereof.

Adjusting components can be added to water and injected into the formation through one or more injection wells that are subjected to pressure to drive the components into the formation.

Various concentrations of adjusting components can be used. Those skilled in the art can determine the amount needed to provide a desired level of methane production based on the teachings of the present description.

Methane Recovery

After an amendment is effected, the formation may be shut in for a sufficient period of time to allow the microorganisms to produce methane or alternatively production may be ongoing throughout the amendment.

It will also be understood that the subterranean carbonaceous medium can be endogenous material or an exogenous material that is taken from its place of origin, to a laboratory for testing, and characterisation, etc.

The generated methane is preferably recovered after the completion of the dosing of each of the nutrient compositions, although methane collection and the dosing of the nutrient composition may also occur concurrently.

In a preferred embodiment, each of the nutrient composition doses or dosages is delivered to produce an amended indigenous environment (i.e. nutrient composition plus indigenous environment of the microbial consortia) which is allowed to incubate, thereby stimulating the microbial consortia to grow, and/or produce methane. The stimulation may also be to an existing methane generating consortia, whereby the stimulation encourages the consortia to grow better and to generate higher levels of methane in gases produced.

The nutrient composition of the invention preferably comprises at least nitrogen and/or phosphorus.

The duration of monitoring/incubation period starting after the completion of the first dosing of the nutrient composition, will depend upon the microbial consortia, its amended environment and the desired commercial methane production rate. However, it would be typically expected that the incubation period would be between seven days and three years, more preferably between two months and two years and even more preferably between six months and 18 months. In the case of the shorter time frames, less than 2 months, for example, it will be understood that these period are particular to the methods of the invention when applied to laboratory or small scale stimulations/models, rather than field studies where the longer intervals of >2 months/years are more appropriate.

Preferably, the monitoring of the microbial consortia environment is undertaken during the dosing phase; the incubation phase and/or the methane recovery phase. More preferably, monitoring is conducted over all of the stages of the process. It should be noted that the more extensive the monitoring of the microbial consortia environment that occurs, the better the knowledge of how the microbial consortia is expected to respond to nutritional and/or environment stimuli. This enables tailored second and/or subsequent nutrient compositions for better control and more sustainable production of biogenic methane on a commercial basis.

In certain embodiments, for example, where sampling for monitoring methane generation occurs periodically, the incubation period could be weekly, fortnightly, or even annually. Indeed, and preferably in same embodiments, for sample where the environment is particularly dynamic or reactive, sampling/monitoring could be substantially continuous where intervals between consecutive samples are very short, for example, second, minutes, hours or even daily.

Again, in the case of the shorter sampling/analysis time frames it will be understood that these period are particular to the methods of the invention when applied to laboratory or small scale stimulations/models, rather than field studies where the longer intervals of >2 months/years are more appropriate, although with substantially continuous monitoring sensors, a essentially continuous monitoring can be undertaken, even in the field.

The recovery of methane preferably occurs as part of a cyclic process comprising a dosing phase (i.e. dosing of the nutrient composition), an incubation phase and a methane recovery phase. Suitably, the recovery of methane may occur over at least two process cycles, preferably over at least three cycles or more preferably still, until the catchment area is no longer commercially sustainable.

Suitably, the parameter associated with the maximum amount or quantity of methane generation produced and/or a peak rate of methane generation preferably is measured at least once per incubation/dosing cycle or a series of parameters can be averaged to indicate a general trend associated with a cycle/incubation period. If the parameter is below a predetermined level, this indicates that remedial action is required. If singe parameter is not below a predetermined level, this indicates that no remedial action is required. The predetermined values can be selected based on previous studies around the formation and consortia environment, or can be based on a % change in the corresponding parameter for the previous cycle.

While a single sample point is be utilised in this manner, it is preferable that two or more, and indeed a plurality of sample points, such as substantially continuous sampling monitoring, is carried out during each incubation period/dosing cycle. This is because the more methane generation data available for a particular incubation allows subtle and/or dramatic increases/decreases in methane generation to be observed. In this manner, peak parameters can be easily and accurately identified and remdial actions can be initiated swiftly.

Thus in one embodiment, for example, where a substantially continuous gas sensor rapidly measures evolved gas composition, the parameter may be as simple as methane concentration, measured for example, with respect to: % composition (relative to a know volume of gas), $mg/dm^3$, molarity ($m/dm^3$), etc. Similarly, the parameter might be an isotopic ratio, a thermal or ionic conductivity measurement or a gas or partial pressure value that is associated with discrete changes in the evolved gas composition.

Recovery of methane produced by the microbial activity may involve gas production technology known in the art, for example, through gas production wells or the like.

Collecting Methane

It will be appreciated by persons skilled in the art that the manner for collecting the methane will depend on whether the carbonaceous material may be an in situ carbonaceous material or an ex situ carbonaceous material.

In respect of in situ carbonaceous material, the techniques for collecting methane are well understood by those skilled in the art of recovering coal seam methane and associated gas from various recovery wells of oil and gas bearing subterranean formations. For example, to extract the gas, a steel-encased hole may be drilled into the coal seam (100-1500 meters below ground). As the pressure within the coal seam declines due to natural production or the pumping of water from the coalbed, both gas and 'produced water' come to the surface through tubing. Then the gas is sent to a compressor station and into natural gas pipelines. Similarly, in respect of ex situ carbonaceous material, the techniques for collecting methane are well understood by those skilled in the art of recovering biogas from reactors, bioreactors, heaped piles, and so forth. For example, the ex situ carbonaceous material may be confined in a closed space to retain the biogenic methane in a headspace thereof. The closed space may be defined by a shell disposed over the ex situ carbonaceous material, or any suitable covering such as a tarpaulin. The methane may be withdrawn from the headspace under positive or negative pressure.

Collector for Collecting Methane

It will be appreciated by persons skilled in the art that the collector for collecting the methane will depend on whether the carbonaceous material may be an in situ carbonaceous material or an ex situ carbonaceous material.

In respect of in situ carbonaceous material, the collector for collecting methane are well understood by those skilled in the art of recovering coal seam methane (CSM) and other carbonaceous material bearing subterranean formations. For example, recovery wells may be drilled to recover methane from the in situ carbonaceous material. The recovery well may be in fluid communication with a compressor to compress the recovered methane, and a storage reservoir or transport conduit for natural gas distribution.

It will be appreciated that the geometry of injection sites, laterals and recovery wells can be variable, but must be based on local geologic, structural, and hydrologic conditions in order to maximise the injection volumes of nutrient combination (concentrate) and to attain maximum recovery of methane. Additionally, at some point in time, the carbonaceous material between the injection sites or laterals and the recovery wells may become methanogenically unproductive. Subsequently, the recovery wells may be converted into injection sites and a new series of recovery wells may be drilled.

Sampling and gas compositional analysis can be performed easily by measuring a volume of gas evolved and sampling same for gas component presence using a suitable analytical technique, for example, GC analysis. However, the number of sampling points available can be limited to the evolution of a certain minimum level of evolved gas. Therefore, in preferred embodiments, sensitive inline gas compositional sensors can be used to continuously monitor the gas composition of any evolved gases. For example, infrared, semiconductor based, ultrasonic based, or electrochemical based gas sensors can be used. Electrochemical based gas sensors that measure concentrations of a target gas by oxidising or reducing the gas at an electrode and measuring the resulting current are particular preferred. Use of the latter is particularly desirable since rapid changes in methane generation rates can quickly be detected, allowing better remedial reaction times and more controlled over the system.

Monitoring the Amendment Process

During the amendment process, changes in the formation conditions and changes in the microbial consortia made up and performance are preferably monitored via the monitoring methods described herein.

Normally fluid samples will be obtained from the formation through one or more wells in communication with the formation.

The samples are analysed to determine the concentration and type of microorganisms in the fluid as well as the concentration of stimulants and microbial products in the fluid. Other geochemical analyses may also be performed to assess the effectiveness of the stimulants on the formation environment and to confirm the chemical compatibility of the desired injectant and the subsurface fluids and solids. Where a requirement for further amended is indicated by the sampling results, the concentration of stimulants in the waterflood may be adjusted accordingly to bring the stimulant effect back within acceptable range.

Thus, changes in the rate of methane generation per unit volume of evolved gas generated for a given nutrient concentration for any incubation period can be calculated. This information can be used to make a determination as to the effect of variation nutrient dosages into a particular consortia environment over a given interval. Thus, the average daily rate of methane generation prior to initial dosing can be used as a baseline, and compared with a peak rate of methane generation per unit of nitrogen for first/initial, second and/or subsequent nutrient doses where required. This facilitates the initiation of remedial action, where necessary in accordance with the present invention, such that flagging methane production can be reinvigorated and/or optimised and/or prolonged compared to where no nutrient dosing regimen is followed. The method of the invention thereby improves the efficiency and sustainability of coal seam methane recovery.

Once selected, if required, the parameter and/or peak parameter can be normalised for a given nutrient concentration in a particular cycle and/or for a given volume of gas generated. In some embodiments, these parameters can be averaged over an entire incubation period, other otherwise manipulated, so that a convenient comparison can be made to the parameter when normalised to a different nutrient concentration in a different cycle.

Suitably, the parameter associated with the maximum amount or quantity of methane generation produced and/or a peak rate of methane generation preferably is measured at least once per incubation/dosing cycle, or a series of parameters can be averaged to indicate a general trend associated with a cycle/incubation period. If the parameter is below a predetermined level, this indicates that remedial action is required. If singe parameter is not below a predetermined level, this indicates that no remedial action is required. The predetermined values can be selected based on previous studies around the formation and consortia environment, or can be based on a % change in the corresponding parameter for the previous cycle.

While a single sample point is be utilised in this manner, it is preferable that two or more, and indeed a plurality of sample points, such as substantially continuous sampling monitoring, is carried out during each incubation period/dosing cycle. This is because the more methane generation data available for a particular incubation allows subtle and/or dramatic increases/decreases in methane generation to be observed. In this manner, peak parameters can be easily and accurately identified and remdial actions can be initiated swiftly.

Thus in one embodiment, for example, where a substantially continuous gas sensor rapidly measures evolved gas composition, the parameter may be as simple as methane concentration, measured for example, with respect to: % composition (relative to a know volume of gas), $mg/dm^3$, molarity ($m/dm^3$), etc. Similarly, the parameter might be an isotopic ratio, a thermal or ionic conductivity measurement or a gas or partial pressure value that is associated with discrete changes in the evolved gas composition.

In another embodiment, the parameter may correspond to the rate of methane generation over any given time/sampling interval. In this case, observation of a reduction in a maximum/peak rate of methane generation will signal that the system is likely to benefit from commencement of a second dosing cycle according to the invention.

In one embodiment, the maximum/peak rate of methane generation may be determined starting by calculating the average daily rate of methane generation over a given incubation period. It will be understood that the average daily rate of methane generation can be determined by considering the volume of methane gas recovered from a gas samples collected over a set time/incubation period.

Thus, changes in the rate of methane generation per unit volume of evolved gas generated for a given nutrient concentration for any incubation period can be calculated. This information can be used to make a determination as to the effect of variation nutrient dosages into a particular consortia environment over a given interval. Thus, the average daily rate of methane generation prior to initial dosing can be used as a baseline, and compared with a peak rate of methane generation per unit of nitrogen for first/initial, second and/or subsequent nutrient doses where required. This facilitates the initiation of remedial action, where necessary in accordance with the present invention, such that flagging methane production can be reinvigorated and/or optimised and/or prolonged compared to where no nutrient dosing regimen is followed. The method of the invention thereby improves the efficiency and sustainability of coal seam methane recovery.

In another embodiment still, the parameter may correspond to an average daily % contribution to a sample methane composition that is collected over a given sampling period. For example, for a system generating methane and tending towards increased efficiency, in a sampling/sample collecting interval of 10 days, a methane gas composition of 5% can be determined (by GC for example). In this case, the average daily % contribution to the methane composition would be 0.2%. If this level of methane production is for an incubation cycle involving 100 mg/L nitrogen component, then the average daily % contribution to the methane composition per unit nitrogen parameter would be 0.002. Thus, for an increasingly efficient system, this parameter will increase, whereas after maximum efficiency has been surpassed, this parameter will start to decrease, thereby indicating that the system is beginning to become less efficient, signalling remedial action is suitable/desirable.

Advantageously, considering increases and decreases in evolved gases and methane compositional changes will allow the skilled person to better under the methane generation processes in the formation to better allow approximations to be made as to the sustainability/potential lifetime of a particular system.

Soil as a Model for Nutrient Absorption/Desorption

Nitrogen, phosphorus and potassium are key nutrients for microbial biological activity and have been the focus for nutrient based biostimulant amendments to stimulate microbial methanogenesis. These nutrients are consumed by microbial activity; in the natural environment they go through a biological cycle of various chemical forms.

In agriculture, the nutrients applied as fertiliser are consumed through plant uptake but in addition can be adsorbed to soils, mainly to the clay fraction. In addition, phosphate ions may react with soil minerals also reducing bioavailability. The high adsorption capacities of many soils act to limit nutrient mobility and can mean that much of the applied fertiliser is not available for biological activity.

An important question not considered in relation to coal methanogenesis experiments relates to the nutrient behaviour during gas generation. Nutrient consumption during these experiments has not been described and may be an important factor in the observed behaviour of gas generation. While coal has a well described capacity to adsorb gases, the behaviour of nutrients in coal has not been considered.

The biostimulation of coal seam gas generation is the nature of nutrient adsorption for coal and is considered to follow the adsorption process observed in soils. Accordingly, as demonstrated the soil system is considered a suitable model for adsorption studies on coal.

Described herein are core flooding experiments where nutrient amended formation water is flowed through intact coal core samples at reservoir pressures and temperatures. In addition to quantifying the gas generated, the nutrient concentrations are measured during the experiments and used to estimate the nutrient mass balance. The nutrient adsorption behaviour for several coal samples is characterised.

Nutrient Adsoption on Coal—Comparision with Soil

The process of nutrient adsorption in soils has been the subject of considerable research. Soils can have a high adsorption capacity for nutrients with the adsorption process determined by the ionic form of the nutrients in aqueous solution and the electrostatic charge of soil constituents.

Figure 1:
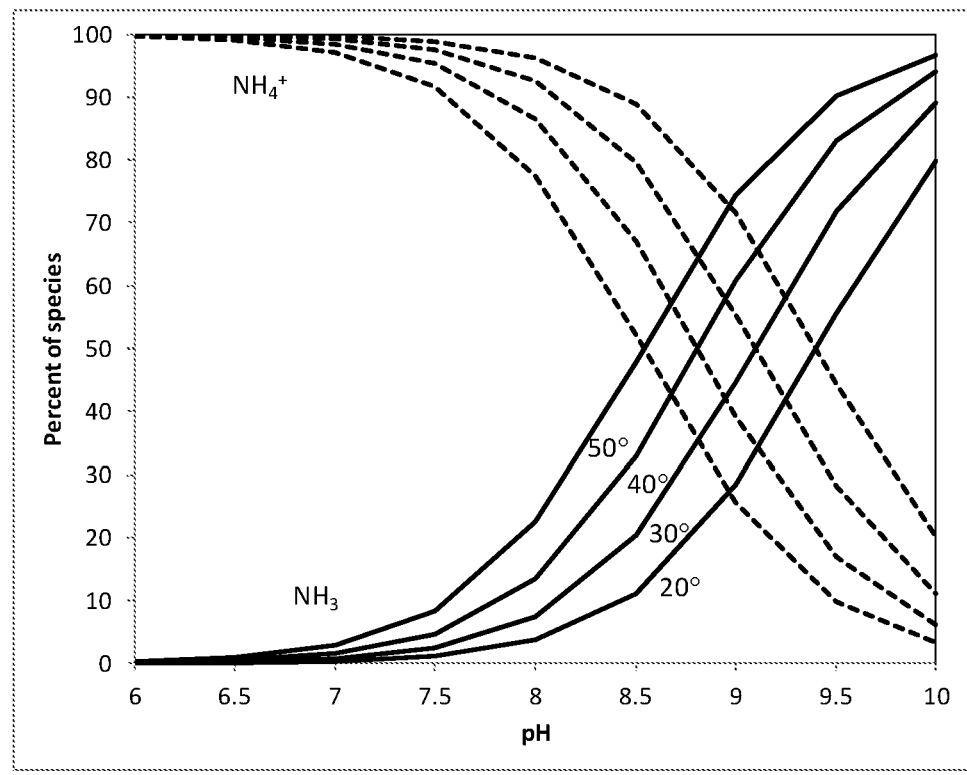
FIG. 1 illustrates the speciation of ammonia with respect to pH.
Figure 2:
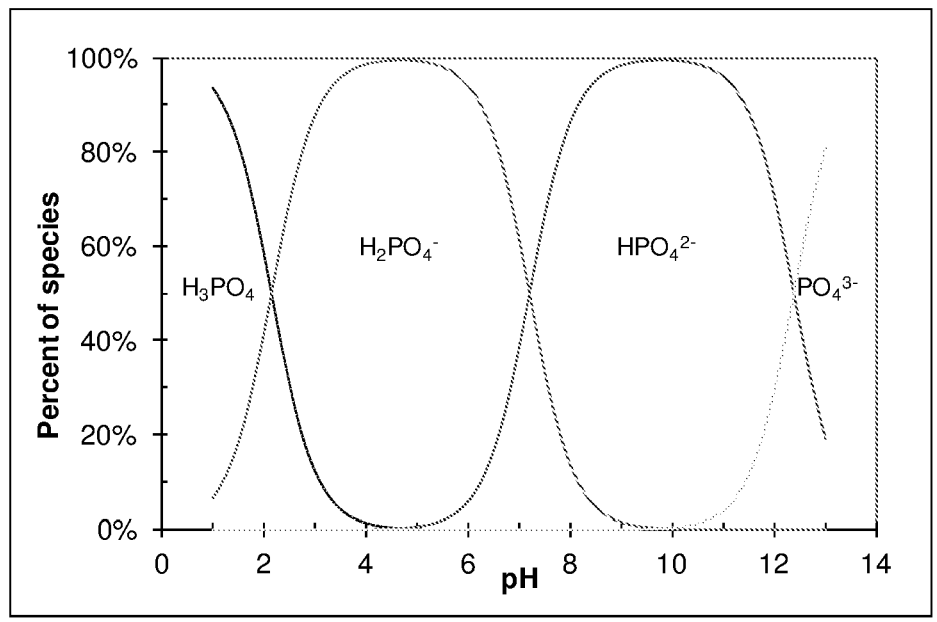
FIG. 2 illustrates the speciation of phosphates with respect to pH.

In aqueous solution, ammonia, phosphate and potassium form ionic species; for phosphate and ammonia the speciation is a function of the pH. FIG. 1 presents the ionic species of ammonia with respect to pH and FIG. 2 for the forms of phosphate in aqueous solution.

Notably, for formation waters with a pH less than 8.5, the ammonium cation is the dominant form. For phosphate, the speciation is more complex with two forms likely to be present; $H_2PO_4^-$ and $HPO_4^{2-}$. At low pH, phosphate is present in solution in an un-ionised form and therefore would be expected to have a low adsorption capacity.

Important characteristics for adsorption in soils are the cation exchange capacity (CEC) and the anion exchange capacity (AEC). These properties, as the names suggest, define the capacity of the soil to store cations and anions.

There is an order in the strength of adsorption for various cations known as the lyotropic series:

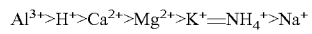

$Al^{3+} > H^+ > Ca^{2+} > Mg^{2+} > K^+ = NH_4^+ > Na^+$

Following the above series, as the pH decreases the concentration of $H^+$ increases, with more being adsorbed and displacing/releasing other weaker adsorbing cations into solution. At high pH the converse happens with more cations being adsorbed/removed from the environment. For ammonium and potassium nutrients, this means the adsorption capacity should increase as the pH increases and conversely, desorption capacity should increase as the pH is reduced. Since cations compete for adsorption sites, the presence of potassium and ammonium in solution will act to lower the adsorption capacity of each of the cations in the series. Overall the cation exchange capacity (CEC) increases as pH increases.

The anion lyotropic series follows:

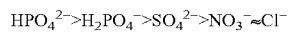

$HPO_4^{2-} > H_2PO_4^- > SO_4^{2-} > NO_3^- \approx Cl^-$

The phosphate ions are strongly adsorbing in this sequence. In contrast to the cation exchange capacity (CEC), the anion exchange capacity (AEC) increases with decreasing pH.

Another mechanism that could affect phosphate availability is precipitation with metal cations such as calcium, iron and aluminium, through the formation of insoluble metal salts.

Adsorption Experiments Coal #1

Coal from an Australian coal seam gas basin was used in these experiments and is referred to as Coal #1; see Table 1.

The adsorption experiments were performed in 250 mL screw top glass jars using 30 g of crushed coal and 150 mL of nutrient solution. The jars, coal and water were sterilised prior to the experiments to eliminate microbial nutrient consumption.

The nutrient adsorption isotherms were determined using four solutions with different concentrations of ammonium and phosphate (Samples 1 to 4). In addition, a control experiment was performed to verify that the nutrient concentration would remain stable over time if no coal was present (Sample 5). The nutrient concentrations in this work are expressed on a mass of nitrogen or phosphorus basis although these are in the form of ammonium ($NH_4^+$) and phosphate ($PO_4^{3-}$) and this is denoted by $NH_3$—N and $PO_4$—P.

The phosphorus and ammonia concentrations were determined by colorimetric methods using a spectrophotometer (DR3900, HACH). For phosphate, the water sample to be analysed was added to a prepacked test tube (TNTplus845, HACH) containing ascorbic acid and ammonium molybdate. A blue product is formed from reaction with the phosphate in the sample and the intensity of the blue colour is directly proportional to the amount of phosphate present.

Ammonia was measured using the salicylate method which involves a three-step reaction sequence. The first reaction step involves the conversion of ammonia to monochloroamine by the addition of chlorine. The monochloroamine then reacts with salicylate to form 5-aminosalicylate. Finally, the 5-aminosalicylate is oxidized in the presence of sodium nitroferricyanide to form a blue-green colored dye that absorbs light at 650 nm. The reagent comes prepared and prepacked in test tubes (TNTplus832, HACH). A standard curve was prepared by plotting the absorbance reading against known concentrations of ammonia ($NH_3$—N NIST 150 mg/L standard solution, HACH) and phosphate standards ($PO_4$ NIST 500 mg/L, HACH). The sample concentration is then computed by comparing sample absorbance to the standard curve.

Figure 3:
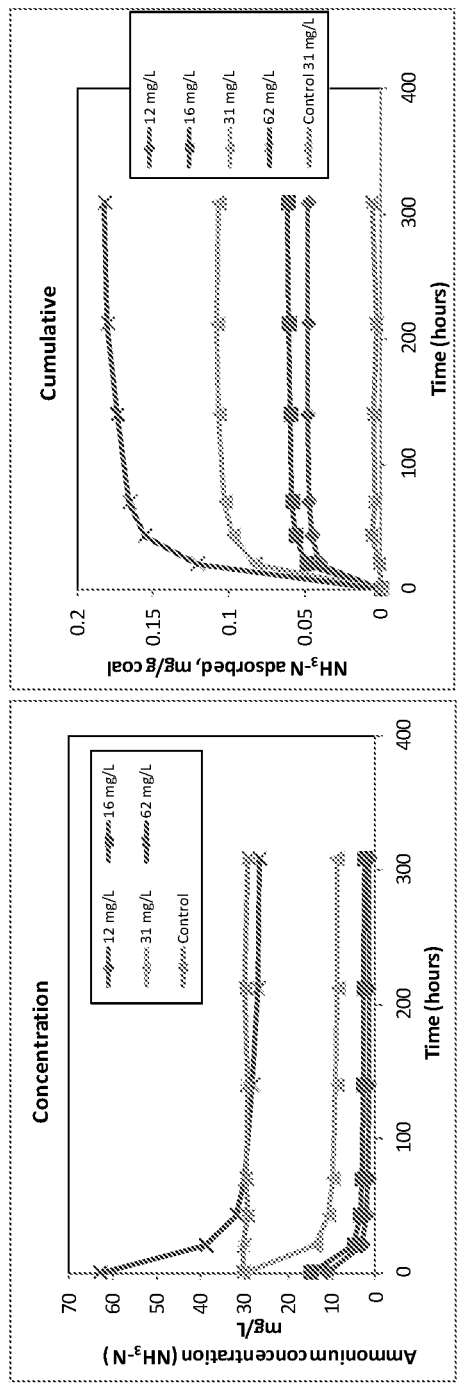
FIG. 3 illustrates the ammonium concentration (left) and the cumulative ammonium adsorbed (right) over time for Coal #1.

The left figure in FIG. 3 presents the change in the ammonia concentration ($NH_3$—N basis) with time. The results demonstrate that the ammonia concentration in the solution decreases significantly over the first 50 hours but then starts to plateau. Also presented in this figure is the control sample without coal where the concentration of ammonia remained constant; supporting evidence that the change in ammonia concentration is due to uptake by coal adsorption. The right figure in FIG. 3 presents the calculated cumulative change in the ammonia concentration with time highlighting the relationship that the quantity adsorbed has to the initial ammonia solution concentration.

Coal absorbs ammonia but the absorption plateaus after about 50 hours.

Figure 4:
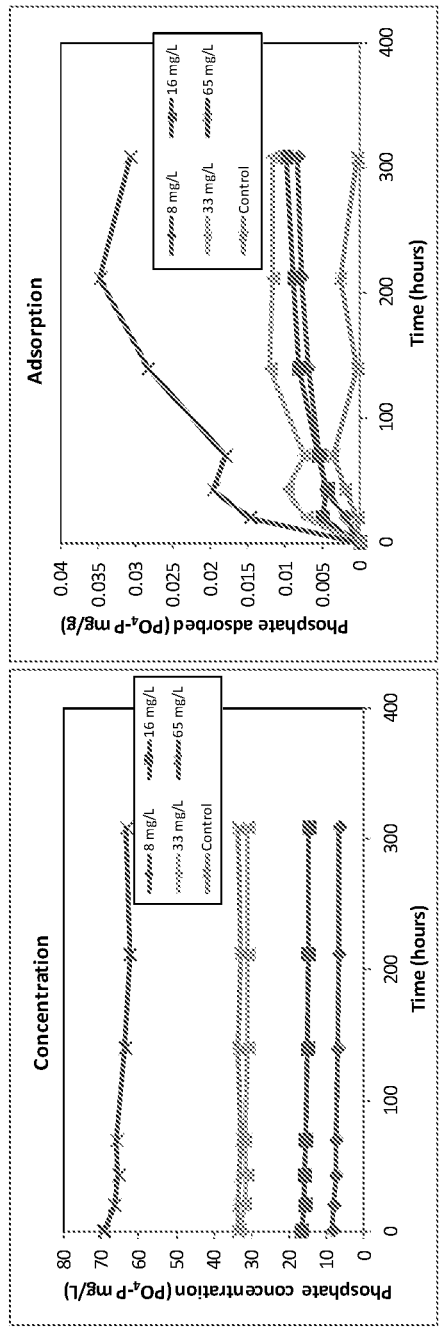
FIG. 4 illustrates the phosphate concentration (left) and the cumulative adsorbed (right) (on a $PO_4$—P basis normalised by the coal mass) over time for Coal #1.

The equivalent results for phosphate are presented in FIG. 4 and shows that the reduction in the solution concentration of phosphate over time is much less significant but phosphate adsorption onto coal appears to be a function of the initial phosphate solution concentration. Furthermore, as the changes in the solution concentration are much less significant, it is understood that the measurement error has a greater effect on the calculated cumulative uptake results shown in the figure on the right.

Figure 5:
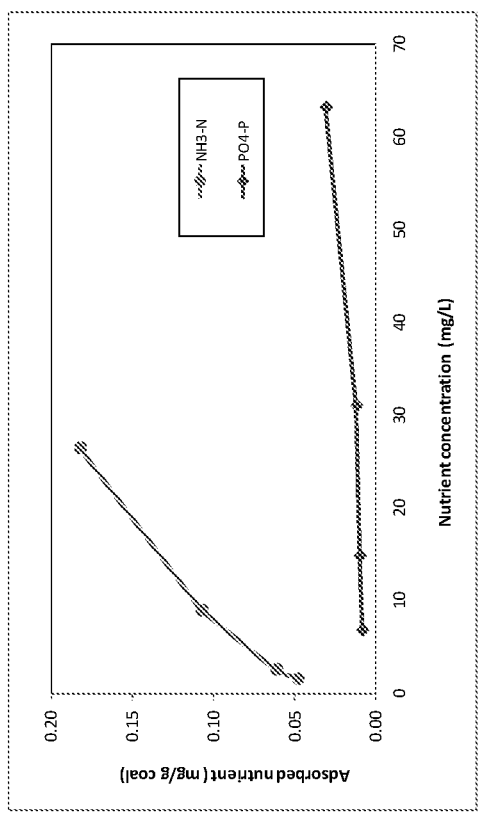
FIG. 5 illustrates the quantity adsorbed (normalised by the coal mass) for ammonia ($NH_3$—N basis (blue line)) and phosphate ($PO_4$—P basis (red line)) for Coal #1 with respect to the equilibrium concentration.

The nutrient adsorption isotherms for Coal #1 are presented in FIG. 5 highlights that phosphate is significantly less adsorbing than ammonia.

This means that a greater proportion of ammonia than phosphate provided in the form an aqueous solution is absorbed such that the amounts of ammonia potentially available to microbes can be much different than anticipated by the starting amounts provided in a bio-stimulating composition.

Desorption Experiments Coal #1

Desorption experiments were performed using the adsorption equilibrated coals from the previous adsorption experiments (Samples 1 to 4). The coal was drained of water using a syringe which left approximately 25 mL of water in the container calculated from the initial coal mass, the mass of the jar and the amount of water removed. 50 mL of Milli-Q water was added to each sample container so that the nutrient concentration would be lowered from what the sample had equilibrated to in the adsorption experiments. If adsorption was reversible the lower concentrations present in the surrounding water would lead to desorption of the previously adsorbed nutrients.

Figure 6:
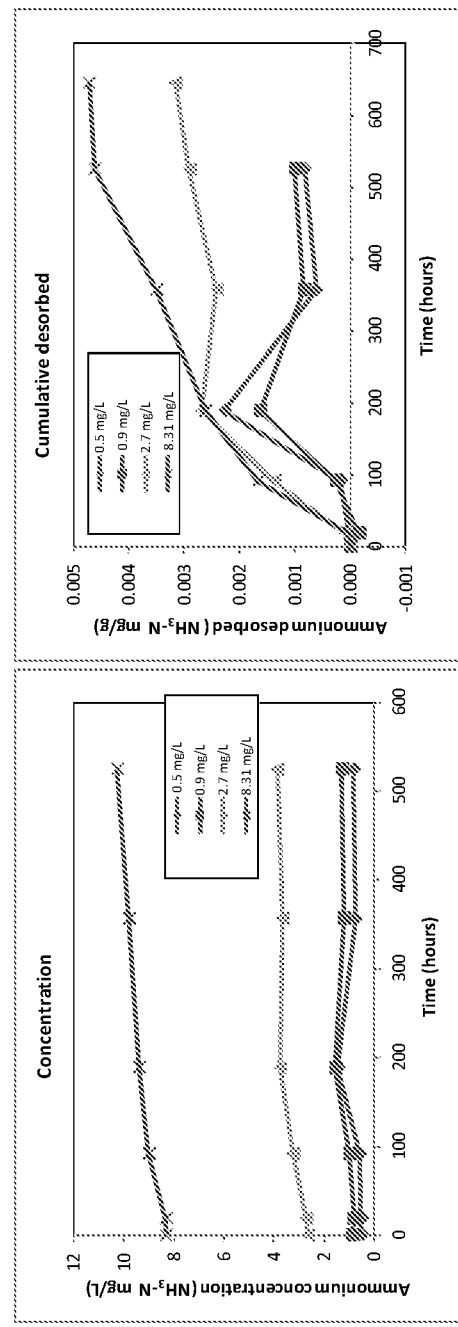
FIG. 6 illustrates the change in ammonium concentration during the desorption experiment and cumulative ammonium (on $NH_3$—N basis) normalised by the coal mass desorbed over time for Coal #1.
Figure 7:
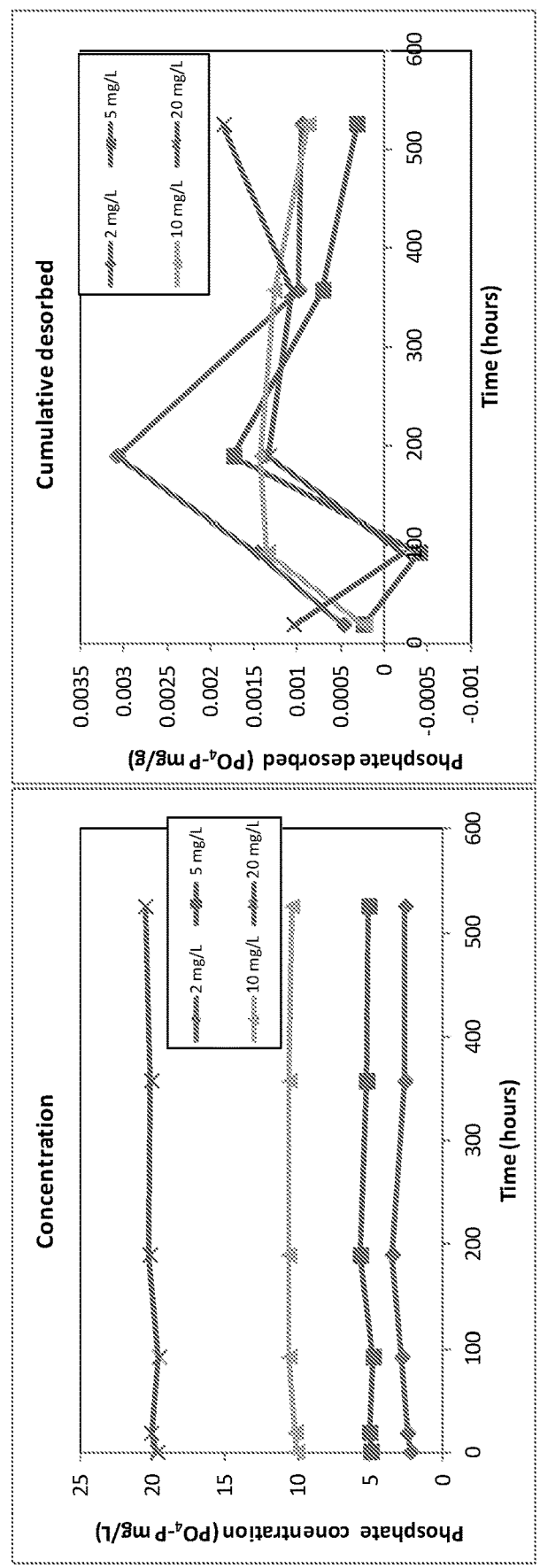
FIG. 7 illustrates the change in phosphate concentration ($PO_4$—P basis) (left) during the desorption experiment and cumulative phosphate desorbed per g coal (right) over time for Coal #1.

FIG. 6 and FIG. 7 present the change in nutrient concentration and the cumulative nutrient desorbed during the desorption experiment. The results demonstrate that coal nutrient adsorption is not readily reversible in response to lowering the nutrient solution concentration as only comparatively small quantities of the nutrient could be desorbed during the experiment.

This means that once adsorbed it may be difficult to desorb ammonia and/or phosphate from coal, at least by providing a reduced concentration gradient, for example, in the form of a biostimulating composition.

pH Effects in Coal Nutrient Adsorption

Figure 8:
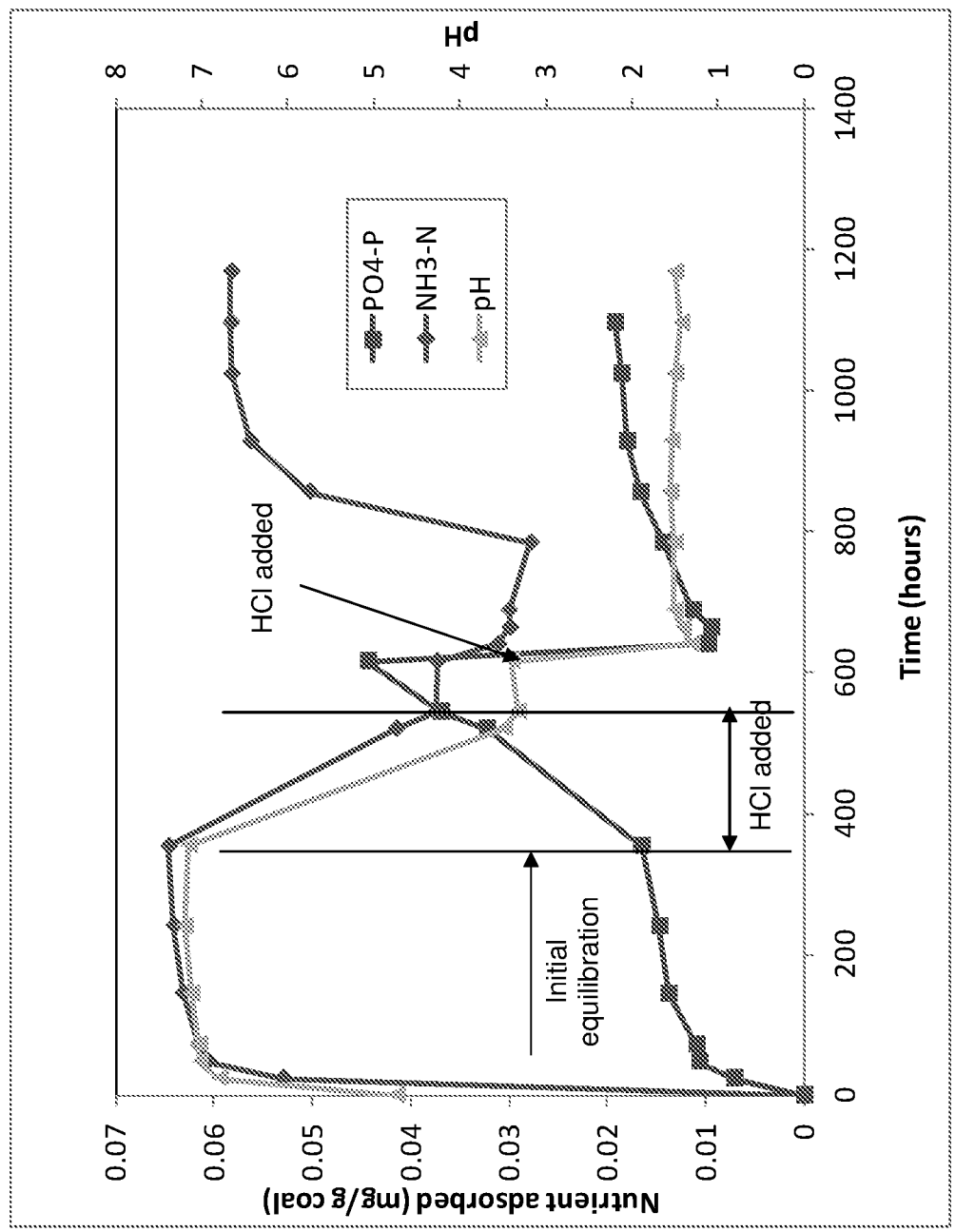
FIG. 8 illustrates the quantity of nutrient adsorbed (ammonia ($NH_3$—N basis) (blue) and phosphate ($PO_4$—P basis) (red)) with time and manipulation of the pH for Coal #1.

To establish if the adsorption behaviour in coal followed that known to occur for soils with respect to pH, an experiment was conducted which measured the quantity adsorbed with respect to pH. Here the nutrient concentration was monitored in a solution with an initial concentration of 31 mg/L $NH_3$—N and 33 mg/L $PO_4$—P in contact with 30 g of crushed Coal #1. Initially adsorption is allowed to equilibrate. As shown in FIG. 8, during this initial period the pH increases, as phosphate ($PO_4^{3-}$) is taken out of solution by absorption onto the coal. After adsorption had equilibrated, the pH was lowered in a series of steps by adding HCl at the time points illustrated in FIG. 8. As with the previous coal adsorption experiments, the coal, water and container were sterilised and thus microbial activity eliminated so that it is clear the changes in nutrient concentration did not result from microbial activity.

The solution concentration results were used to calculate the quantity adsorbed and the behaviour of this in time is also presented in FIG. 8. The phosphate uptake by absorption increases when the pH decreases from 7 to about 3.5. This observation is in line with the following the expected behaviour of the anion exchange capacity for soils which increases as pH decreases. Over this pH range phosphate species changes from a mixture of $H_2PO_4^-$ and $HPO_4^{2-}$ to being almost entirely $H_2PO_4^-$. However, when the pH is lowered further to a pH of about 1.5, the absorption uptake is reversed and phosphate desorbs from the coal so that the overall total adsorbed is significantly reduced. This corresponds to the speciation behaviour with pH presented in FIG. 2, where at pH=1, the phosphate is almost entirely in the non-ionised, low adsorbing form of $H_3PO_4$.

Thus, it is apparent that on going from acidic to a low pH of about 3.5 phosphate adsorption increases as the ion exchange capacity is greater at low pH.

Notably, lowering the environmental pH even further to a pH of about 1.5 releases and/or reverses nutrient adsorption onto coal.

This indicates that nutrient absorption can be attenuated through varying the local environmental pH.

Ammonium adsorption is also affected by the pH, as it remains in the ionic ammonium form ($NH_4^+$) over the entire pH range of the experiment. As the pH drops to 3.5, the ammonium nutrient desorbs from the coal in a manner that would be expected for the cation exchange capacity (CEC) of a soil which decreases with decreasing pH. Lowering the pH further to 1, results in an additional quantity of ammonium desorbing. However, over time when the pH stabilises around 1.5, $NH_3$—N starts to re-adsorb onto the coal again, though the equilibrium adsorbed quantity is slightly less than that observed for a pH of 7 (2 mg compared to 1.8 mg). It is possible that the solution concentration of other ions, such as calcium, is changing and contributing to this behaviour.

This experiment demonstrated that phosphate and ammonium adsorption behaviour in coal is consistent with the known behaviour in soils. However, the pH of these experiments (pH of 3.4 and 1) are likely to be too acidic for optimal microbial growth in certain formulations. The experiment provide useful models for biostimulation attenuation via nutrient absorption/desorption processes.

Nutrient Adsorption Isotherms for Other Coal Samples

To evaluate the variability of nutrient adsorption behaviour based on coal type, adsorption isotherms were measured for several other coal samples; Coal #2, Coal #3, and Coal #4. In addition to ammonium and phosphate, potassium was also characterised.

Figure 9:
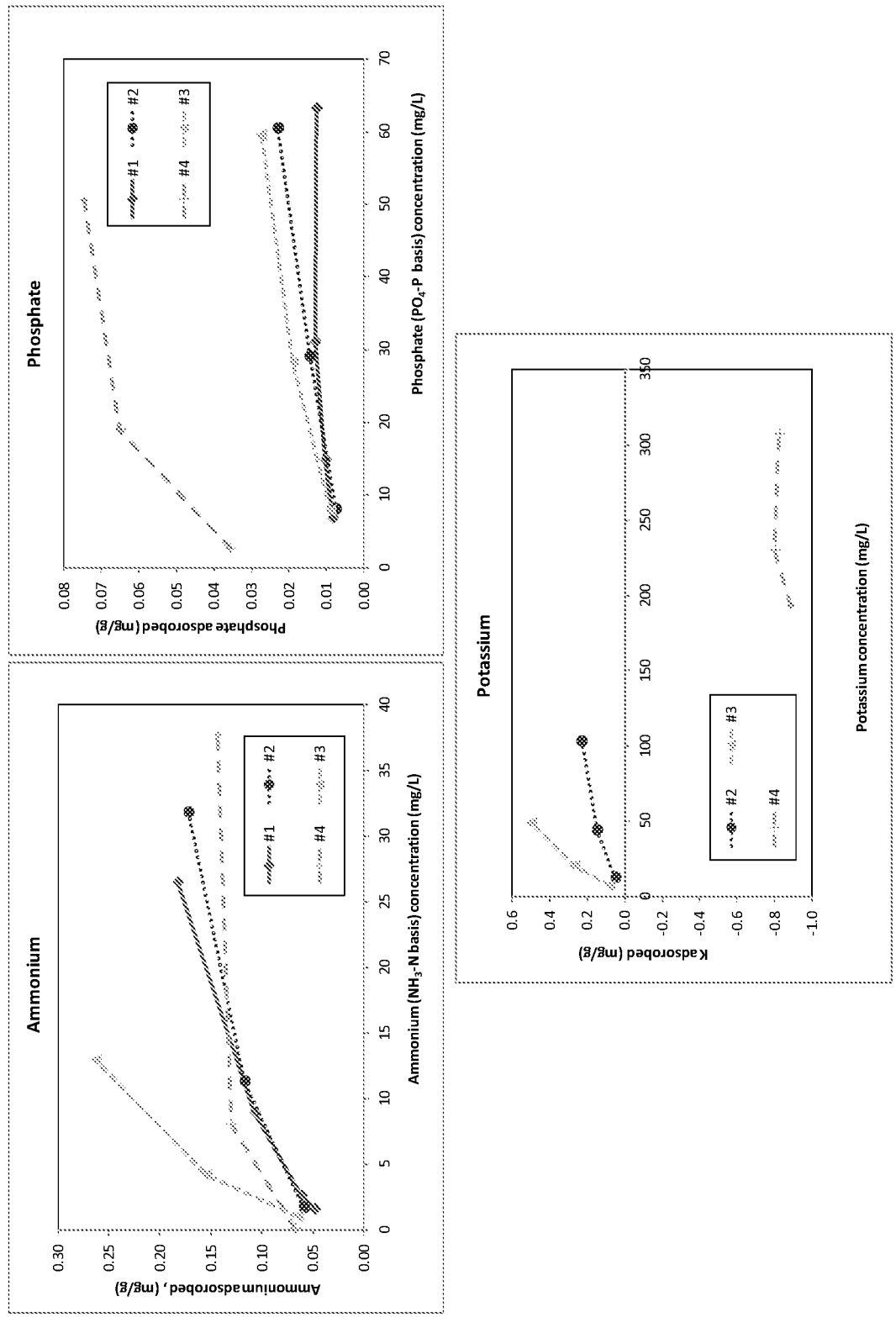
FIG. 9 illustrates the Ammonium (on a $NH_3$—N basis), phosphate ($PO_4$—P basis) and potassium adsorption isotherms for Coals #1, #2, #3 and #4 (as a function of equilibrium nutrient concentration).

FIG. 9 presents the ammonium adsorption isotherms which demonstrate that while ammonium adsorption is comparable for coal types Coal #1, 2 and 4, Coal #3 has a significantly higher adsorption capacity which cannot be attributed to differences in the petrology of the coal presented in Table 1.

TABLE 1

Maceral composition and vitrinite reflectance for the coal samples used in this work.

| SAMPLE NO | $R_{V,MAX}$ (%) | VITRI-NITE (%) | LIPTI-NITE (%) | INERTI-NITE (%) | MIN-ERAL (%) | VITRI-NITE (%)* | LIPTI-NITE (%)* | INERTI-NITE (%)* |
|---|---|---|---|---|---|---|---|---|
| Coal#1 | 0.45 | 75.7 | 15.3 | 2.6 | 6.4 | 80.9 | 16.4 | 2.7 |
| Coal#2 | 0.48 | 47.4 | 22.2 | 21.6 | 8.8 | 52.0 | 24.3 | 23.7 |
| Coal#3 | 0.42 | 53.9 | 22.3 | 14.0 | 9.8 | 59.7 | 24.7 | 15.6 |
| Coal#4 | 0.83 | 65.2 | 1.6 | 27.6 | 5.6 | 69.1 | 1.7 | 29.2 |
| Coal#5 | 0.63 | 28.1 | 3.6 | 64.4 | 3.9 | 29.2 | 3.8 | 67.0 |

*mineral free

FIG. 9 also presents the phosphate adsorption isotherms and highlights the comparatively high adsorption capacity of Coal #4 for phosphate. The results highlight that the adsorption capacity for the nutrient ammonium is consistently higher than that for phosphate nutrient for all coal types tested. Coal appears to have a higher adsorption affinity for ammonia than for phosphate.

The adsorption isotherms for potassium is also presented in FIG. 9, and shows that while Coal #2 and #3 adsorbed potassium, Coal #4 desorbed potassium meaning that this coal must have contain water soluble potassium at the start of the experiment. Potassium measurement was not available for the Coal #1 sample and so adsorption for this sample cannot be presented.

These results demonstrate the potential impact different types or indeed formation pockets of coal may have with respect to the presence of biostimulant natively present in the formation or added as part of a biostimulation dosing plan.

Biostimulation Experiments at Reservoir Pressure and Temperature

Methodology

Two experimental approaches were used to test biostimulation under reservoir conditions: (i) core flooding experiments on coal core samples, and (ii) a batch rig arrangement.

The core floods involved continuous flow of nutrient amended formation water through intact coal core over a 10 week period. The batch rig experiments also used coal core at reservoir pressure and temperature but the nutrient inflow was pulsed rather than continuous. While core flooding could only be performed on one sample at a time, the batch rig experiments used a simpler experimental arrangement that allowed 5 simultaneous cores to be tested.

The core flooding rig used in this project is presented in FIG. 35. Teledyne ISCO 260D syringe pumps were used to control pressure and inflow and outflow water rates as well as the confining pressure. A mass controlled phase separator provided separation of outflow gas and water. Upstream and downstream sample ports provided a means of obtaining regular water and/or gas samples. The nutrient amended formation water was contained in a Swagelok vessel upstream of the sample with a helium filled ISCO pump used to drive water from the vessel through the core sample. The rig was housed in a temperature controlled cabinet to maintain temperature at reservoir conditions.

The batch rig used five pressure vessels housed in a temperature controlled water bath. Nutrient amended formation water was contained in a Swagelok vessel upstream of each core sample with a pressure regulator controlled helium headspace to provide drive pressure for water flow during the experiments. Flow occurred in a pulsed fashion rather than the continuous flow used with the core flooding experiments. During each flow pulse, a downstream needle valve was opened and outflow fluid collected. In between flow pulses the core sample was shut-in at test pressure. The batch rig provided a simple arrangement that allowed five experiments to be conducted in parallel. The confining pressure was also controlled via a pressure regulator. Both rigs used triaxial pressure vessels with a membrane to isolate the core from the confining fluid which was at an elevated pressure to the pore pressure.

The experiments involved the following stages:
(i) core sample preparation—the sample was prepared by having the ends trimmed using a diamond wire saw. Depending on the core integrity, the sample was either coated in epoxy or a viton rubber membrane was installed to separate the sample pore system from the triaxial pressure vessel confining fluid.
(ii) vacuuming and purging—using helium of the core sample to reduce and/or characterise the residual gas content of the core sample. During this phase the outflow gas was regularly sampled and analysed using gas chromatograph.
(iii) either core flood, or pulsed flow for the batch experiments using nutrient amended formation water were carried out.

Core Flood Experiments

During the core flood the inflow and outflow water was periodically sampled and the nutrient concentration analysed using the procedure describe above. Prior to nutrient analysis, the sampled water was allowed to degas into a confined helium filled headspace that was at atmospheric pressure. The headspace gas was then sampled and analysed using GC/MS. With this procedure the concentration of gas dissolved in the outflow water could be measured to provide an indication of gas generation during the flood. This core flood period lasted for 10 weeks. The pore pressure during these experiments was 5 MPa and temperature was 40° C.

The sample was purged of water using helium while still at test pressure and the gas composition of the helium outflow analysed using gas chromatograph. As the core sample was degassed prior to the core flood and the pore pressure was high, any generated gas was adsorbed during the core flood. Thus, the following procedure was used to determine the quantity of gas generated. The inflow side of the sample was shut-in and the pore pressure of the sample allowed to decrease by flowing into the outflow syringe pump which was maintained at atmospheric pressure. In the final stage the sample was briefly vacuumed and then shut-in with desorbed gas collected in a Swaglok pressure vessel. These two volumes were added together to estimate the total volume gas generated.

Coal seam formation water used in these experiments obtained from a producing coal seam gas well. A sample of this water was obtained under anoxic conditions to preserve anaerobic organisms with $Na_2S$ and cysteine added to scavenge oxygen and resazurin as an oxygen indicator. A larger bulk sample was also obtained under aerobic conditions. This larger volume was used to provide the water for the experiment; it was filter sterilised and then inoculated with the anoxic sample. Formation water samples from two wells within the same producing area were used in this project; Fluid #1 and Fluid #2.

Batch Rig Experiments

The batch rig experiments used Coal #4 core and the sample masses and nutrient concentrations for the inflow fluid are presented in Table 2.

TABLE 2

Batch experiments using Coal#4 coal core sample.

| CELL | CORE SAMPLE mass (g) | INFLOW FLUID | RESIDUAL $ch_4$ partial pressure (atm) |
|---|---|---|---|
| 1 | 132.9 | Fluid#1, $NH_3$—N 14 mg/L, $PO_4$—P 52 mg/L | 0 |
| 2 | 142.2 | Fluid#1, $NH_3$—N 14 mg/L, $PO_4$—P 52 mg/L | 0 |
| 3 | 128.3 | Fluid#1, $NH_3$—N 18 mg/L, $PO_4$—P 52 mg/L | 0 |
| 4 | 131.8 | Fluid#1, $NH_3$—N 19 mg/L, $PO_4$—P 52 mg/L | 0 |
| 5 | 153.9 | Fluid#1, $NH_3$—N 19 mg/L, $PO_4$—P 52 mg/L, $Na_3$ 1 g/L | 0.031 |

Fluid #1 inoculum was used with two sets of repeat experiments using the same inflow nutrient concentrations. Cell 5 was used to measure nutrient adsorption and to prevent microbial activity the inflow fluid contained 1 g/L sodium azide as a biocide.

An initial helium flood was conducted on the samples to determine residual methane content within the core. After a period of flooding to purge the sample of methane, the cells were shut-in and the methane concentration in the free gas of the coal porosity allowed to equilibrate with the adsorbed gas within the coal. The gas composition was then measured and the partial pressure determined. For Cells 1 to 4 the methane concentration was below the detection limit of the gas chromatograph but Cell 5 had a relatively small residual methane pressure of 0.031 atmospheres.

Water Flow and Gas Results

For the batch experiments approximately 5 ml of inflow fluid was flowed through each cell a week. This flow occurred over 5 injections per week with each injection having a duration of approximately ten minutes with the cells shut-in between the injections. Over the course of one week this was equivalent to an average flow rate of approximately 0.0005 ml/min.

Samples of the inflow and outflow liquid were analysed weekly. The headspace gas composition of the outflow liquid, expressed as $CH_4$ and $CO_2$ partial pressures within the core sample, are presented in FIG. 11. Gas partial pressure within Cell 5 (with no microbial activity) is several orders of magnitude lower than the other 4 cells, reflecting the gas generation occurring in the cells using microbially active water.

The gas content for core samples was determined at the end of the batch experiment by progressively lowering the pore pressure to atmospheric pressure and collecting desorbed gas from each core into measuring cylinders. To recover the gas below atmospheric pressure, the cylinder was attached which was vacuumed and then opened to the core sample. The pressure response of this cylinder due to gas desorption was used to calculate gas volumes and gas composition analysed using gas chromatograph. This vacuum technique was repeated until there was no further gas desorption.

From the results presented in FIG. 12, the four cells containing microbial consortia with nutrient amendment had significant gas generation. Even though there was negligible $CO_2$ measured in the headspace analyses of the water samples during the experiment, it comprised up to 30% of the gas content. It is possible that during the experiment the high adsorption capacity of $CO_2$ onto coal meant that it was effectively being removed from the water before outflow.

Nutrient Measurements and Analyses

The concentration of ammonium (on $NH_3$—N basis) and phosphate ($PO_4$—P basis) over the course of the batch experiment are presented in FIG. 13 to FIG. 17. This concentration data can be combined with the water flow observations (presented in FIG. 10) to calculate the nutrient mass inflow and outflow and thus the uptake can be estimated from the difference between these. FIG. 8 presents the consumption rate for ammonia and phosphate and FIG. 20, shows the cumulative consumption. FIG. 20 presents the consumption rate and cumulative consumption of potassium during the experiment. These results show that potassium is leaching from the core samples during the experiment and are consistent with the isotherms for this coal which also show an increase in concentration. These observations commence at day 40 in the experiment when potassium measurement became available.

The cells using microbially active water have significantly higher ammonium uptake than Cell 5 which had nutrients but a biocide to prevent microbial activity and where nutrient uptake was due to adsorption. The ammonium measurements with microbial activity are relatively close together even though there were differences in the quantities of gas generated between these cells. The quantity adsorbed represents approximately 50% of the nutrient uptake.

Total phosphate uptake was significantly higher than the ammonium consumption, for both the microbially active experiments and the adsorption experiment. This is in contrast with the adsorption isotherms presented in FIG. 9 where the ammonium adsorption was approximately twice that observed for phosphate with Coal #4. This difference in adsorption behaviour between the equilibrium adsorption with the isotherms and the core floods could be the result of different adsorption times for these two nutrients for Coal #4.

Core Flooding Experiments

This section presents the results from two core flood experiments as described in Table 4.

TABLE 3

Summary of the nutrient concentrations and inoculums used for the core flood experiments.

| Cell | Equivalent Gas Content (m³/tonne) | |
|---|---|---|
|  | CH$_4$ | CO$_2$ |
| 1 | 0.48 | 0.11 |
| 2 | 0.30 | 0.12 |
| 3 | 0.33 | 0.07 |
| 4 | 0.52 | 0.15 |
| 5 | 0.00 | 0.01 |

Coal #5 Core Flooding Experiment

After installation in the triaxial pressure vessel the core sample was vacuumed and then brought up to test pressure and temperature and a helium purge commenced in order to remove or reduce the residual methane from the core sample. The outflow helium was regularly sampled and analysed using gas chromatograph for CH$_4$ and CO$_2$ composition. It was found that CH$_4$ and CO$_2$ were below the detection limit, indicating there was no or very low levels of residual methane in the sample.

A nutrient flood of approximately 10 weeks duration was performed at a pressure of 5 MPa and temperature of 45° C. Finally, a helium flood was performed to drive nutrient solution and free gas from the core, before the pore pressure was decreased to desorb gas and determine the gas content.

Water Flow and Gas Results

The nutrient flood was undertaken for a period of 10 weeks; during which approximately 370 mL of nutrient amended formation water flowed through the core (FIG. 21). The average flow rate of water during the core flood was 4.4 mL/day. Throughout the nutrient flood, weekly samples were taken of the upstream and downstream water in order to characterise nutrient concentrations.

The headspace gas was then analysed to determine the gases dissolved within the outflow water, as an indicator of gas generation during the nutrient flood. When this core flood was conducted the measurement methodology was still under development and as a result there is some variability in the measurements due to sampling and procedural differences. The results are presented in FIG. 23 and have low levels of CO$_2$ but significant methane partial pressures, in a similar fashion to the dissolved gas analyses presented in FIG. 11 for the batch experiment.

FIG. 23 presents the gas volume (as a gas content) recovered during the degassing of the coal sample after the core flood. During the helium purge some adsorbed methane had diffused into the helium but most of the gas was recovered by lowering the pore pressure, with the methane outflow significantly increasing when the pressure dropped below 0.5 MPa suggesting this was close to the methane desorption pressure. Total amount of CH$_4$ corresponded to a gas content of 0.97 m³/tonne. An additional 0.081 m³/tonne was recovered by the vacuuming step (step 4 described in Section 0) so the total gas generated during the experiment was 1.06 m³/tonne. CO$_2$ levels were very low and comprised 0.026 m³/tonne.

Nutrient Analysis

The concentrations of ammonium and phosphate measured from the fluid samples are presented in FIG. 24. These concentrations were combined with the water flow observations to calculate the nutrient mass balance during the core flood and thus the nutrient consumption. FIG. 25 presents the nutrient uptake rate and cumulative nutrient uptake over time. While ammonium and phosphate uptake are very close for this experiment the relative impact on the nutrient concentrations are significantly different; a large proportion of the ammonium is consumed during flow through the core, whereas a much smaller proportion of the phosphate is consumed.

Coal #4 Core Flooding Experiment

The Coal #4 nutrient flooding experiment was undertaken for a period of 10 weeks at a pore pressure of 5 MPa, effective stress of 0.5 MPa and temperature of 40° C. The inflow fluid consisted of the Fluid #1 inoculum and a nutrient concentration of 50 mg/L NH$_4$ and 400 mg/L PO$_4$.

An initial vacuum and helium flood performed on the sample indicated that there was no residual CH$_4$ or CO$_2$ present.

Water Flow and Gas Results

FIG. 26 presents the water flow rate during the nutrient flood; over the 10 week core flood 205 mL of nutrient amended water flowed through the sample. As this flood used a slightly different experimental setup to the previous core floods, the flow through the core was controlled to a constant rate, set to a value of 0.002 mL/min. The perturbations from this rate in FIG. 26 were due to water sampling.

Throughout the flood weekly samples of the inflow and outflow water were taken to measure nutrient concentrations. FIG. 27 presents the partial pressures of dissolved gas within the water samples calculated from the sample headspace. CH$_4$ partial pressure increased over the course of the nutrient flood, indicating the presence of microbial activity and gas generation however the these were considerably lower than seen in the Coal #5 experiment.

At the conclusion of the water flood, the gas content was determined by first desorbing gas into the outflow pump, and finally by attaching a vacuum cylinder which was cycled a number of times to collect and analyse any remaining adsorbed gas.

The total amount of methane generated during the experiment corresponded to a gas content of 0.35 m³/tonne (see FIG. 28). The CO$_2$ generated was equivalent to 0.087 m³/tonne. Despite considerably lower methane partial pressures, the gas contents were comparable to those observed from the Coal #4 batch experiment (see Table 3):

TABLE 4

Gas contents at the end of Coal#4 batch experiment.

| | Sample dimensions | | | Inflow nutrient concentration | | |
|---|---|---|---|---|---|---|
| Sample name | Length (mm) | Diameter (mm) | Mass (g) | NH$_3$—N mg/L | PO$_4$—P mg/L | inoculum |
| Coal#5 | 64 | 78 | 348 | 26 | 70 | Fluid#2 |
| Coal#4 | 61 | 74 | 260 | 27 | 40 | Fluid#1 |

Nutrient Analysis

The concentrations of ammonium (as NH$_3$—N) and phosphate (as PO$_4$—P) over the course of the core flood are presented below in FIG. 29. The cumulative and the rate of ammonium and phosphate consumption are presented in FIG. 30. Phosphate has a higher rate of consumption than ammonium for this coal, but for both nutrients the consumption rate has a downward trend by the end of the experiment.

The higher phosphate than ammonium consumption that was observed is consistent with the Coal #4 batch experiment. The total uptake is higher than the quantity measured during the Cell 5 adsorption experiment where the adsorbed quantities were 0.0015 mg/g $NH_3$—N and 0.0039 mg/g $PO_4$—P over a period of less than 80 days. The instrument for making potassium measurements was not available at the time of this core flooding experiment and as a result this nutrient was not characterised.

Summary of Gas Generation and Nutrient Consumption

FIG. 31 presents the gas generated during the experiments described above with respect to the total nutrient consumption. There are significant differences in the observed gas generation between the experiments in which the inflow fluid was inoculated with Fluid #1 and the core flooding experiment with Coal #5 which used Fluid #2. For the Coal #5 experiment the amount of methane generated was considerably higher and the proportion of $CO_2$ much lower than the experiments which used Fluid #1 and Coal #4. It is not possible to determine from these experiments whether these differences are the result of the properties of the coal or the inoculums used since no experiments could be performed where the coals and inoculums were swapped over.

The results from Coal #4 with Fluid #1 core flooding and batch experiments are generally consistent with the quantity of methane generated over the 10 week experiments ranging from 0.3 to 0.5 m$^3$/tonne and 0.07 to 0.15 m$^3$/tonne $CO_2$. There is a general trend of decreasing gas generation with increased nutrient consumption which suggests that lower nutrient concentrations leading to lower consumption could improve gas generation. However $CO_2$ was also higher for these lower nutrient consumption experiments.

Results Discussion

The laboratory experiments demonstrate that biostimulation by nutrient amendment of coal seam formation water could lead to gas generation on flow through intact coal core at reservoir pressure and temperature. The gas rates observed and nutrients consumed are directly relevant to planning the field application of this biostimulation procedure.

The coals and formation waters used in the experiments came from different wells within the same producing field however the quantity of gas generated and $CO_2$ composition varied significantly. For the best results, the amount of methane generated over the ten week experiment was significant and the level of $CO_2$ low; an important outcome for the feasibility of biostimulation as a practical strategy for coal seam gas producers.

Nutrients are a key aspect of biostimulation and their consumption relative to the quantity of methane generated will play a part in determining the ultimate economic benefits.

Critically, it has been found that nutrient consumption is the combined effect of adsorption and microbial consumption. It was found that while coal has a significant nutrient adsorption capacity, slow adsorption times (as demonstrated by the Coal #4 batch rig adsorption experiment) mean that the quantity adsorbed was significantly lower than the adsorption capacity. In the Coal #4 experiments (which had relatively low rates of gas generation) uptake due to adsorption was between 35 and 46% of the total ammonia uptake and 30-74% of the total phosphate uptake.

In addition, as was shown above, the pH determines the ionic form of the nutrients and this in turn influences the adsorption behaviour on coal in a similar fashion to that observed for soils. However, the ionic form also is important to biological activity, with un-ionised forms of nutrients inhibitory to biological activity.

Experiments with Low Adsorbing Nutrients

The objective of the following set of experiments was to investigate reducing nutrient adsorption by coal to increase nutrient availability and thereby lower the cost of methane recovery per unit volume gas generated. Lower nutrient absorption would reduce the nutrient consumption associated with MECSM and thus the quantity of water required for injection.

One potential low adsorbing nitrogenous nutrient investigates herein is urea, which is typically transformed to ammonia after application. Furthermore the potential of organic acids (acetic acid etc) to lower phosphate and ammonia adsorption in coal has been investigated.

Batch experiments were carried out using crushed coal. These involved core flooding experiments to test the identified treatments through core flooding (5× core floods). The experiments use formation waters with established gas generation potential Batch & Core Flood Experiments with Low Absorbing Nutrients Three batch experiments were completed Batch Experiment Methodology Sterile crushed coal in a sterile glass jars were amended with various the following nutrients fluids: nitrogen based nutrients: $NH_4Cl$; urea ($CO(NH_2)_2$) or phosphorus based nutrients: $K_2HPO_4$; or organic acids.

In each case, the concentration of $PO_4^{3-}$, $NH_4^+$ was measured. pH was also measured.

Batch & Core Flood Experiments with Low Absorbing Nutrients

Experiment 1

The purpose of this experiment was to establish experimental procedures; i.e. analysis of urea and organic acids, as well as to establish analysis procedures for nutrients (nitrogen as $NH_4^+$ and phosphorus as $PO_4^-$) measurements using ion chromatography. A further aim was to study adsorption of urea to coal, and compare it to existing nutrient adsorption.

Experiment 1

As reported in earlier, ammonium is highly adsorbed to coal. Additionally, although not as high as ammonium, phosphate ions are still significantly adsorbed to coal. Where urea was used, significant degradation or hydrolysis to form ammonia was observed. The reduction of urea concentration observed was as a result of combined degraded/hydrolysed urea plus any possible adsorption to coal.

Experiment 2

This experiment was a repeat of experiment 1 but investigated the addition of organic acids to the nutrient compositions: 10 mM (0.6 g/L) acetic acid or 1 mM (0.15 g/L) tartaric acid were added and the adsorption of nutrients on coal from location 1 and location 2 was compare compared.

Result

Erroneous mass balance: high liquid loss→Compare concentration profiles

Urea hydrolysis or degradation is still observed.

Adsorption of ammonium is more significant in location 2 coal compared to location 1 coal. However, adsorption of phosphate is more significant in location 1 coal compared to location 2 coal As shown in the Figures, inclusion of organic acids (10 mM acetic acid and 1 mM tartaric acid) appears to reduce to the amount of absorbed nutrient in the coal. Furthermore, the Acetic acid concentration decreases overtime (from ion chromatography—data not shown), and is possibly reacting or adsorbed to coal as well. (Tartaric acid co-elute with another compounds in the IC).

From the above, it is evident that treatment and/pre treatment with acid reduces undesirable nutrient adsorption in some coals.

Experiment 3

Ensure no liquid loss: correct mass balance.

This experiment involved the use of non-coal controls for validation. Higher concentration of organic acids: 100 mM (6 g/L) acetic acid and 5 mM (0.45 g/L) oxalic acid were used. Furthermore biocide (0.5% glutaraldehyde) was used to ensure no organism was present to consume the nutrients.

Compare the adsorption of nutrients of location 1 and location 2 coals

Results

Unexpectedly, location 1 coal has an associated "low" pH of 4.

During the experiment, urea degradation was observed. After 10 days, urea starts to hydrolyse and the $NH_4$ concentration increases. Notably, the total urea loss is the combination of urea degradation as well as any which may be adsorbed.

As shown in experiment 2, ammonium adsorption is much more significant in compared to location 1 (Bowen) coal, while phosphate adsorption is much greater in location 1 (Bowen) coal compared to location 2 (Surat) coal.

Treating location 2 coal with organic acids showed a significant reduction in the amount of ammonium adsorption. Here, coal was incubated with 100 mM of acetic acid for 2 weeks before nutrients were added. This treatment has showed significant reduction in ammonium adsorption. Treating with 5 mM oxalic acid did not appear to make any difference to this particular coal.

For location 2 coal, adding organic acids to lower phosphate adsorption seems does not make a significant difference. For location 1 coal, due to contamination, treatment with acids does not appear to improve the adsorption significantly.

Further experimental using a different location 1 coal at pH 6-7 are being considered.

Summary

Urea—hydrolysis to $NH_4$, about 10 days from the start of experiments

Location 2 Coal:

Highly adsorbed ammonium, not so much of phosphate.

Treatment with organic acids reduce the adsorbed ammonium

Location 1 Coal:

Adsorbed phosphate, but not so much of ammonium

Treatment with organic acids has little effect on the adsorbed phosphate (need to be verified, due to low "pH" contamination).

Next from here: Verification of organic acids results, use other organic acids, e.g. citric acids.

The invention claimed is:

1. A method of increasing methanogenesis efficiency of a solid carbonaceous feedstock in a subterranean formation, wherein the solid carbonaceous feedstock is coal and/or shale, the method comprising the steps of:
   (a) analyzing one or more components of the formation to determine nitrogen nutrient adsorption environmental characteristics of the subterranean formation in its native state;
   (b) detecting a presence of one or more methanogenic microbes within the formation;
   (c) measuring a level of methane gas production within the formation; and
   (d) adding an ion exchange component or a $C_1$-$C_{10}$ organic acid to the subterranean formation to block nitrogen nutrient adsorption sites associated with the solid carbonaceous feedstock.

2. A method according to claim 1, wherein the nitrogen nutrient adsorption sites are blocked for a period ranging from 1 day to 3 years.

3. The method of claim 1, wherein step (a) comprises:
   (i) establishing a baseline concentration of nitrogen nutrients;
   (ii) systematically altering one or more physical and/or chemical properties associated with the solid carbonaceous feedstock that promote nitrogen nutrient adsorption within the formation;
   (iii) identifying one or more nitrogen nutrient adsorption promoting environmental characteristics of the formation by determining which of the altered properties results in an increase or decrease in the baseline concentration of the nitrogen nutrients within the formation.

4. The method of claim 3, wherein determining an increase in a nitrogen nutrients concentration relative to the baseline concentration is indicative of nutrient desorption, occurring within the formation.

5. The method of claim 1, further comprising increasing methanogenesis efficiency.

6. The method of claim 1, wherein the nitrogen nutrient adsorption sites are blocked temporarily.

7. The method of claim 1, wherein the $C_1$-$C_{10}$ organic acid is selected from the group consisting of: formic acid, malic acid, benzoic acid, carbonic acid, butyric acid, propionic acid, lactic acid, oxalic acid, acetic acid, tartaric acid, citric acid, and combinations thereof.

8. The method of claim 1, further comprising the step of adding one or more nutrients or nutrient precursors having no adsorption affinity to the solid carbonaceous feedstock.

9. The method of claim 8, wherein the one or more nutrients comprise one or more urea and urea derivatives.

10. The method of claim 1, wherein the nitrogen nutrient adsorption environmental characteristics are measured by considering gas adsorption isotherms of one or more porous samples of the solid carbonaceous feedstock.

11. The method of claim 1, wherein the $C_1$-$C_{10}$ organic acid is provided in a concentration ranging from about 1 to about 150 mM.

* * * * *